(12) United States Patent
Orr

(10) Patent No.: US 8,038,640 B2
(45) Date of Patent: Oct. 18, 2011

(54) DIAPHRAGM PUMP AND RELATED SYSTEMS AND METHODS

(75) Inventor: Troy J. Orr, Draper, UT (US)

(73) Assignee: Purity Solutions LLC, Draper, UT (US)

( * ) Notice: Subject to any disclaimer, the term of this patent is extended or adjusted under 35 U.S.C. 154(b) by 777 days.

(21) Appl. No.: 11/945,200

(22) Filed: Nov. 26, 2007

(65) Prior Publication Data

US 2009/0137940 A1 May 28, 2009

(51) Int. Cl.
*A61M 37/00* (2006.01)

(52) U.S. Cl. ............................ 604/6.11; 417/477.2

(58) Field of Classification Search .............. 604/4.01, 604/5.04, 6.09, 6.1, 6.11, 65–67; 417/477.2, 417/395, 493
See application file for complete search history.

(56) References Cited

U.S. PATENT DOCUMENTS

| | | |
|---|---|---|
| 2,383,193 A | 8/1945 | Herbert |
| 2,658,526 A | 4/1948 | Porter |
| 2,529,028 A | 11/1950 | Landon |
| 2,755,134 A | 6/1955 | Hughes |
| 2,755,745 A | 7/1956 | Lewis |
| 2,871,795 A | 2/1959 | Smith |
| 3,741,687 A | 6/1973 | Nystroem |
| 4,047,844 A | 9/1977 | Robinson |
| 4,158,530 A | 6/1979 | Bernstein |
| 4,412,553 A | 11/1983 | Kopp et al. |
| 4,479,760 A | 10/1984 | Bilstad et al. |
| 4,479,761 A * | 10/1984 | Bilstad et al. ............. 417/395 |
| 4,490,621 A | 12/1984 | Watabe et al. |
| 4,583,920 A | 4/1986 | Lindner |
| 4,657,490 A | 4/1987 | Abbott |
| 4,690,621 A | 9/1987 | Swain |
| 4,858,883 A | 8/1989 | Webster |
| 4,974,754 A | 12/1990 | Wirz |
| 5,088,515 A * | 2/1992 | Kamen ............... 137/15.17 |
| 5,259,352 A | 11/1993 | Gerhardy et al. |
| 5,342,182 A | 8/1994 | Montoya et al. |
| 5,344,292 A | 9/1994 | Rabenau et al. |
| 5,413,626 A | 5/1995 | Bartsch |
| 5,431,626 A | 7/1995 | Bryant et al. |
| 5,573,385 A | 11/1996 | Chevallier |
| 5,588,816 A | 12/1996 | Abbott et al. |
| 5,593,290 A | 1/1997 | Greisch et al. |
| 5,669,764 A | 9/1997 | Behringer et al. |
| 5,718,567 A | 2/1998 | Rapp et al. |
| 5,902,096 A | 5/1999 | Behringer et al. |
| 5,934,885 A | 8/1999 | Farrell et al. |
| 5,938,634 A | 8/1999 | Packard |
| 6,079,959 A | 6/2000 | Kingsfore et al. |
| 6,106,246 A | 8/2000 | Steck et al. |
| 6,152,705 A | 11/2000 | Kennedy et al. |
| 6,168,394 B1 | 1/2001 | Forman et al. |

(Continued)

OTHER PUBLICATIONS

Notice of Allowance dated Jan. 4, 2010 in U.S. Appl. No. 11/484,061, now U.S. Patent No. 7,717,682.

(Continued)

*Primary Examiner* — Leslie Deak
(74) *Attorney, Agent, or Firm* — Stoel Rives LLP

(57) ABSTRACT

In some arrangements, a pump for moving a fluid has one or more pump chambers and one or more flow control valves with diaphragm actuation regions. Motive fluid can activate the diaphragm actuation regions, and a pattern of fluid flow can be controlled by varying the pressure levels of the motive fluid.

10 Claims, 25 Drawing Sheets

U.S. PATENT DOCUMENTS

| | | | |
|---|---|---|---|
| 6,178,996 | B1 | 1/2001 | Suzuki |
| 6,206,644 | B1 | 3/2001 | Pereira et al. |
| 6,227,824 | B1 | 5/2001 | Stehr |
| 6,229,753 | B1 | 5/2001 | Kono et al. |
| 6,286,566 | B1 | 9/2001 | Cline et al. |
| 6,367,669 | B1 | 4/2002 | Au et al. |
| 6,402,486 | B1 | 6/2002 | Steck et al. |
| 6,481,980 | B1 | 11/2002 | Vandlik et al. |
| 6,579,253 | B1 | 6/2003 | Burbank et al. |
| 6,604,908 | B1 | 8/2003 | Bryant et al. |
| 6,716,004 | B2 | 4/2004 | Vandlik et al. |
| 6,723,062 | B1 | 4/2004 | Westberg et al. |
| 6,752,599 | B2 | 6/2004 | Park |
| 6,759,007 | B1 | 7/2004 | Westberg et al. |
| 6,905,479 | B1 | 6/2005 | Bouchard et al. |
| 7,029,245 | B2 | 4/2006 | Maianti et al. |
| 7,273,465 | B2 * | 9/2007 | Ash .............................. 604/6.11 |
| 7,461,968 | B2 | 12/2008 | Demers et al. |
| 7,717,682 | B2 * | 5/2010 | Orr ................................ 417/395 |
| 2003/0194332 | A1 | 10/2003 | Jahn et al. |
| 2004/0136843 | A1 | 7/2004 | Jahn et al. |
| 2007/0077156 | A1 | 4/2007 | Orr |
| 2009/0137940 | A1 | 5/2009 | Orr |

OTHER PUBLICATIONS

Examiner-Initiated Interview Summary dated Nov. 12, 2009 in U.S. Appl. No. 11/484,061, now U.S. Patent No. 7,717,682.

Amendment and Response to Office Action dated Aug. 21, 2009 in U.S. Appl. No. 11/484,061, now U.S. Patent No. 7,717,682.

Replacement Drawing Sheets dated Aug. 21, 2009 in U.S. Appl. No. 11/484,061, now U.S. Patent No. 7,717,682.

Office Action dated May 8, 2009 in U.S. Appl. No. 11/484,061, now U.S. Patent No. 7,717,682.

Response to Requirement for Election/Restriction dated Apr. 6, 2009 in U.S. Appl. No. 11/484,061, now U.S. Patent No. 7,717,682.

Office Action dated Mar. 4, 2009 in U.S. Appl. No. 11/484,061, now U.S. Patent No. 7,717,682.

Decision on Petition Under 37 C.F.R.§1.182 dated Dec. 11, 2006 in U.S. Appl. No. 11/484,061, now U.S. Patent No. 7,717,682.

Petition to Accept Items in Response to Notice of Omitted Items in a Nonprovisional Application dated Aug. 9, 2006 in U.S. Appl. No. 11/484,061, now U.S. Patent No. 7,717,682.

Forty-four pages, U.S. Appl. No. 11/484,061 titled Double Diaphragm Pump and Related Methods, now U.S. Patent No. 7,717,682.

Sixteen drawing sheets in U.S. Appl. No. 11/484,061 titled Double Diaphragm Pump and Related Methods, now U.S. Patent No. 7,717,682.

Notice of Omitted Items in a Nonprovisional Application, dated Aug. 4, 2006, in U.S. Appl. No. 11/484,061, now U.S. Patent No. 7,717,682.

Response to Restriction Requirement dated Jul. 16, 2010 in U.S. Appl. No. 11/945,177.

Restriction Requirement dated Jun. 16, 2010 in U.S. Appl. No. 11/945,177.

* cited by examiner

DIAPHRAGM PUMP AND RELATED SYSTEMS AND METHODS

TECHNICAL FIELD

Certain embodiments described herein relate generally to the field of fluid transfer. More particularly, some embodiments described herein relate to fluid transfer having a relatively small amount or no amount of impurities introduced to the fluid being transferred and/or relatively little or no damage to the fluid being transferred.

BRIEF DESCRIPTION OF THE DRAWINGS

Understanding that drawings depict only typical embodiments of the invention and are not therefore to be considered to be limiting of its scope, the invention will be described and explained with additional specificity and detail through the use of the accompanying drawings. The drawings are listed below.

INDEX OF ELEMENTS IDENTIFIED IN THE DRAWINGS

Figure 1:
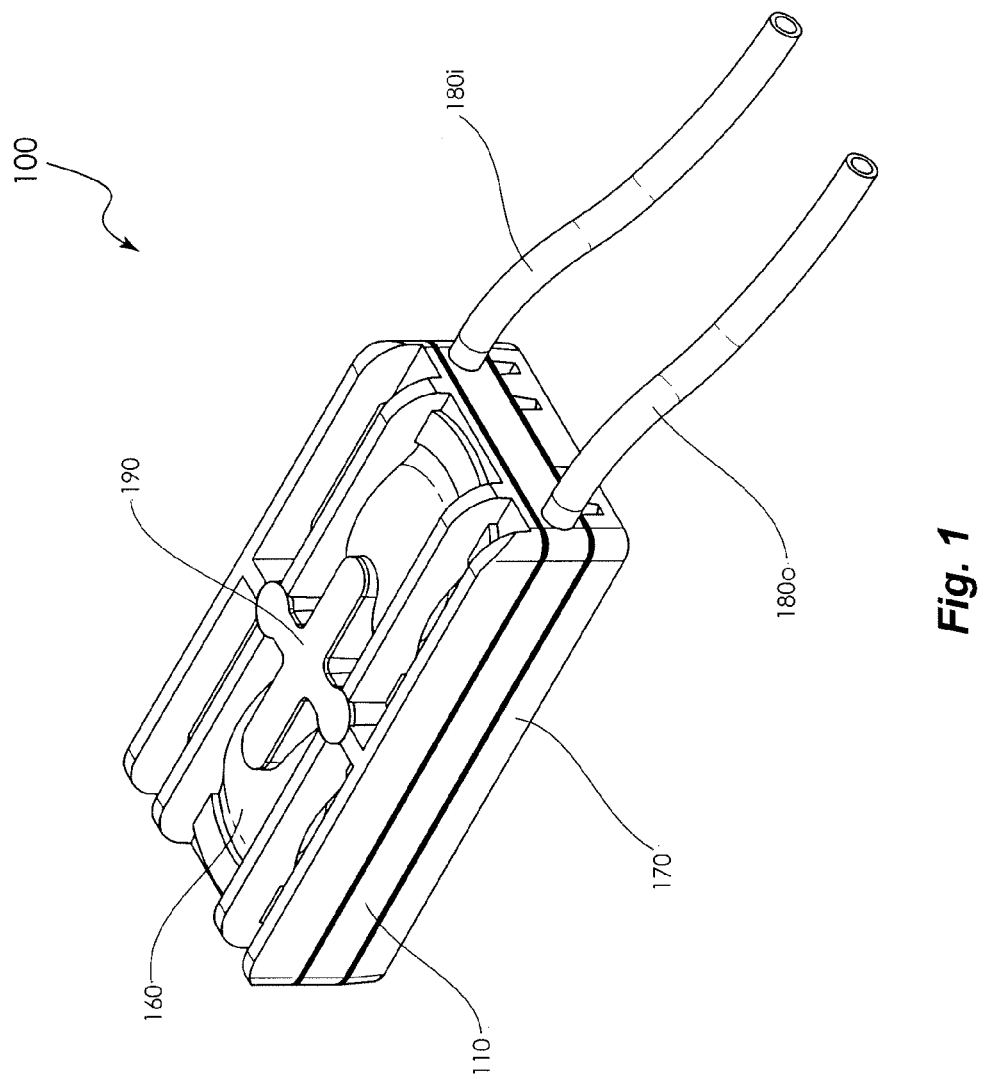
FIG. 1 is a perspective view of an embodiment of a double diaphragm blood pump.

Elements numbered in the drawings include:
100 double diaphragm pump
100a-h double diaphragm pumps
101i first inlet valve chamber
101o first outlet valve chamber
102i second inlet valve chamber
102o second outlet valve chamber
103a first pump chamber
103b second pump chamber
110 pump body
110' pump body with valve bypass channels
111i first inlet valve seat
111o first outlet valve seat
112i second inlet valve seat
112o second outlet valve seat
113a first chamber cavity
113b second chamber cavity
114a surface of first chamber cavity 113a
114b surface of second chamber cavity 113b
115a inclined region of first pump chamber 113a
115b inclined region of second pump chamber cavity 113b
116a rim of first pump chamber 113a
116b rim of second pump chamber cavity 113b
117a perimeter of first pump chamber cavity 113a 117*b* perimeter of second pump chamber cavity 113*b*
118*i* perimeter of first inlet valve seat 111*i*
118*o* perimeter of first outlet valve seat 111*o*
119*i* perimeter of second inlet valve seat 112*i*
119*o* perimeter of second outlet valve seat 112*o*
121*i* groove of first inlet valve seat 111*i*
121*o* groove of first outlet valve seat 111*o*
122*i* groove of second inlet valve seat 112*i*
122*o* groove of second outlet valve seat 112*o*
131*i* first inlet valve portal for fluid communication between inlet channel 138*i* and first inlet valve seat 111*i*
131*o* first outlet valve portal for fluid communication between first outlet valve seat 111*o* and outlet channel 138*o*
132*i* second inlet valve portal for fluid communication between inlet channel 138*i* and second inlet valve seat 112*i*
132*o* second outlet valve portal for fluid communication between second outlet valve seat 112*o* and outlet channel 138*o*
133*i* chamber channel for fluid communication between first chamber cavity 113*a* and first inlet valve seat 111*i*
133*o* chamber channel for fluid communication between first chamber cavity 113*a* and first outlet valve seat 111*o*
134*i* chamber channel for fluid communication between second chamber cavity 113*b* and second inlet valve seat 112*i*
134*o* chamber channel for fluid communication between second chamber cavity 113*b* and second outlet valve seat 112*o*
135*i* seat rim of first inlet valve seat 111*i*
135*o* seat rim of first outlet valve seat 111*o*
136*i* seat rim of second inlet valve seat 112*i*
136*o* seat rim of second outlet valve seat 112*o*
138*i* inlet channel
138*o* outlet channel
139*i* bypass channel between inlet channel 138*i* and first pump chamber 103*a*
139*o* bypass channel between first pump chamber 103*a* and outlet channel 138*o*
140*a*&*b* chamber diaphragms
141*a* first pump chamber diaphragm region of chamber diaphragms 140*a, b*
141*b* second pump chamber diaphragm region of chamber diaphragms 140*a, b*
142*a-f* holes in chamber diaphragm for assembly
150*a*&*b* valve diaphragms
151*i* first inlet valve region of valve diaphragms 150*a*&*b*
151*o* first outlet valve region of valve diaphragms 150*a*&*b*
152*i* second inlet valve region of valve diaphragms 150*a*&*b*
152*o* second outlet valve region of valve diaphragms 150*a*&*b*
160 chamber plate
161*a* first chamber actuation cavity
161*b* second chamber actuation cavity
162*a*&*b* air transfer bosses
163*a* passage between opening 164*a* and boss 162*a*
163*b* passage between opening 164*b* and boss 162*b*
164*a* opening between first chamber cavity 161*a* and passage 163*a*
164*b* opening between second chamber cavity 161*b* and passage 163*b*
165*a*&*b* cavity surface 166*a*&*b*
166*a*&*b* recess
166*c*&*d* inclined regions
167*a*&*b* rims
168*a*&*b* perimeters
169*a-d* assembly posts
170 valve plate
171*i* actuation cavity of first inlet valve 101*i*
171*o* actuation cavity of first outlet valve 101*o*
172*i* actuation cavity of second inlet valve 102*i*
172*o* actuation cavity of second outlet valve 102*o*
173*i* passage between actuation cavity 171*i* of first inlet valve 101*i* and boss 176*a*
173*o* passage between actuation cavity 171*o* of first outlet valve 101*o* and boss 176*b*
174*i* passage between actuation cavity 172*i* of second inlet valve 102*i* and boss 176*c*
174*o* passage between actuation cavity 172*o* of second outlet valve 102*o* and boss 176*d*
175 mounting hook
175*a* opening defined by mounting hook
176*a-d* air transfer bosses
177*i* groove for o-ring 192*a*
177*o* groove for o-ring 192*b*
178*i* groove for o-ring 192*c*
178*o* groove for o-ring 192*d*
179*a-f* assembly holes
180*i* inlet line
180*o* outlet line
190 manifold cover plate
192*a-d* valve o-rings
193*a*&*b* chamber o-rings
210 motive fluid valve
212 valve controller
220 pressure source
230 vacuum source
238 fluid source or blood uptake
289 fluid return, receiver, or destination
300 forming fixture
310 first plate
311*a*&*b* chamber region recess
312*a*&*b* o-ring groove
313*a*&*b* openings between forming recess 311*a, b* and vacuum port 318
314*a*&*b* surface of recess
318 vacuum port or passage
320 second plate
321*a*&*b* heating windows or portals
330 heater
331 heater surface
400 manifold mounting assembly
402*a*&*b* manifold covers
403*a*&*b* mounting latches
405 catch
407 motive fluid transfer boss
410 manifold base
411 motive fluid transfer boss
412 motive fluid transfer boss
413 motive fluid transfer boss
414 motive fluid transfer boss
415 motive fluid transfer boss
416 motive fluid transfer boss
417 transfer passage of manifold between air transfer bosses 412, 413, 414 and portal B
418 transfer passage of manifold between air transfer bosses 411, 415, 416 and portal A
421 flow restriction between air transfer boss 412 and transfer passage 418
422 flow restriction between air transfer boss 415 and transfer passage 417
431*a-f* o-rings 432a&b screws
433a&b washers
434a-d screws
435a&b brackets
436a-d fasteners
450 pump assembly
451 pump control system
452 processor
453 user control interface
454 enclosure
700 cardiopulmonary by-pass system
701 oxygenator
702 arterial tubing segment
703 arterial cannula
704 venous return catheter
705 venous tubing segment
706 reservoir
709 cardioplegia cannula
711 medical fluid bag
712 vent catheter
713 suction device
750 heart-assist system
753 cannula or attachment to vascular system on venous side
754 cannula or attachment to vascular system on arterial side
800 extracorporeal circuit
802 tubing segment on blood uptake from patient vascular system
803 drip chamber
804a&b pressure transducers
805 tubing segment
807 tubing segment
808 heparin pump
810 dialyzer
811 tubing segment
812 drip chamber
814 tubing segment on blood return to patient vascular system
820 dialyzing liquid system
825 air detector
1100 pump
1101i first inlet valve
1101o first outlet valve
1113a first pump chamber
1110 pump body
1133i chamber channel between first inlet valve and first pump chamber
1133o chamber channel between first pump chamber and first outlet valve
1135i rim of first inlet valve
1135o rim of first outlet valve
1138i inlet channel
1138o outlet channel
1140 one or more diaphragms
1141a diaphragm actuation region of first pump chamber
1151i diaphragm actuation region of first inlet valve
1151o diaphragm actuation region of first outlet valve
1160 chamber plate
1162a motive fluid transfer boss
1163a motive fluid passage
1173i motive fluid passage
1173o motive fluid passage
1176a motive fluid transfer boss
1176b motive fluid transfer boss
1180i inlet line
1180o outlet line A first supply port connection between air valve 210 and manifold plate 400
B second supply port connection between air valve 210 and manifold plate 400
P patient

DETAILED DESCRIPTION OF PREFERRED EMBODIMENTS

Figure 6A:
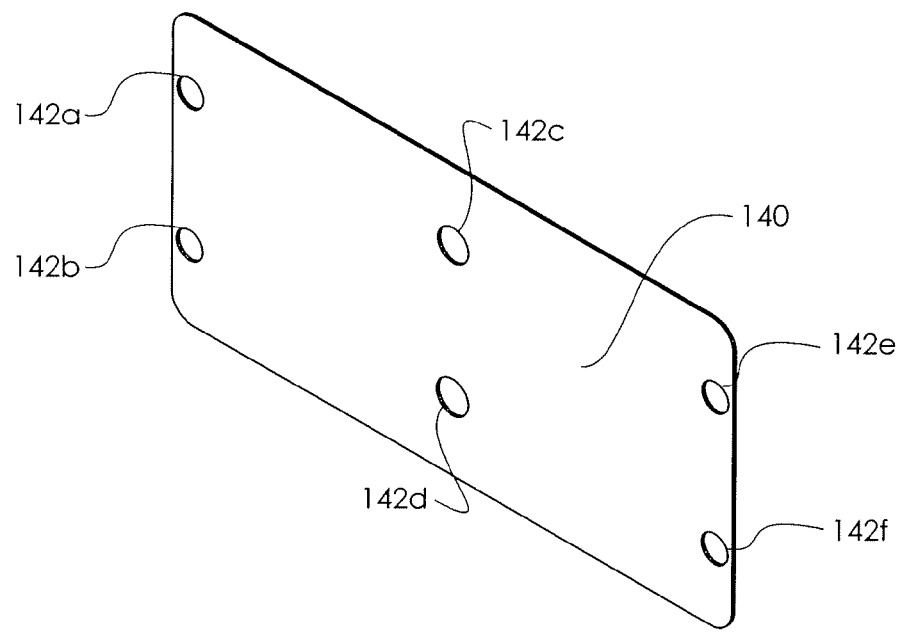
FIG. 6A is a perspective view of an embodiment of diaphragm media before regions have been formed.
Figure 16:
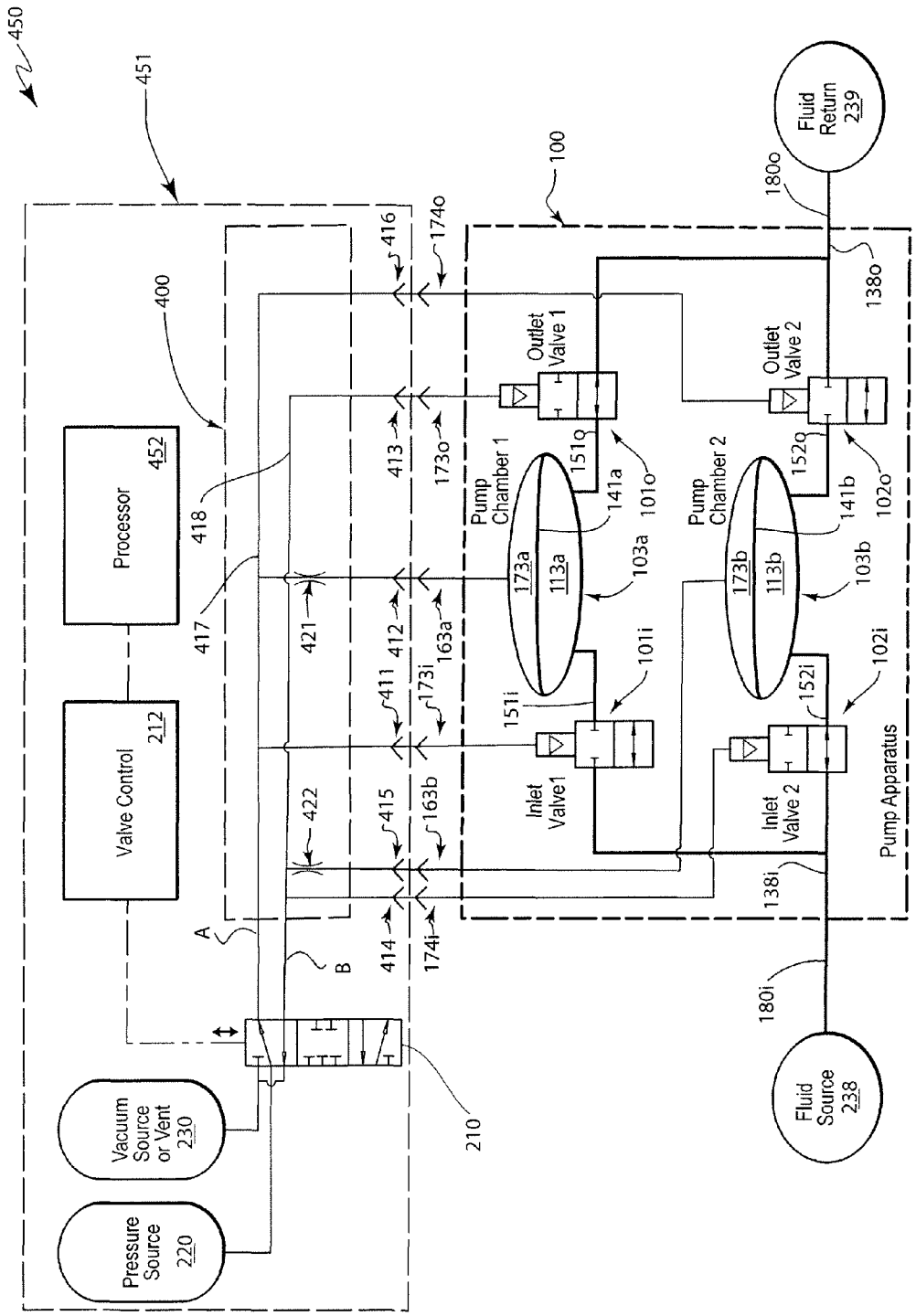
FIG. 16 is a schematic view of an embodiment of a double diaphragm pump as used in a method and system for transferring fluid.
Figure 17:
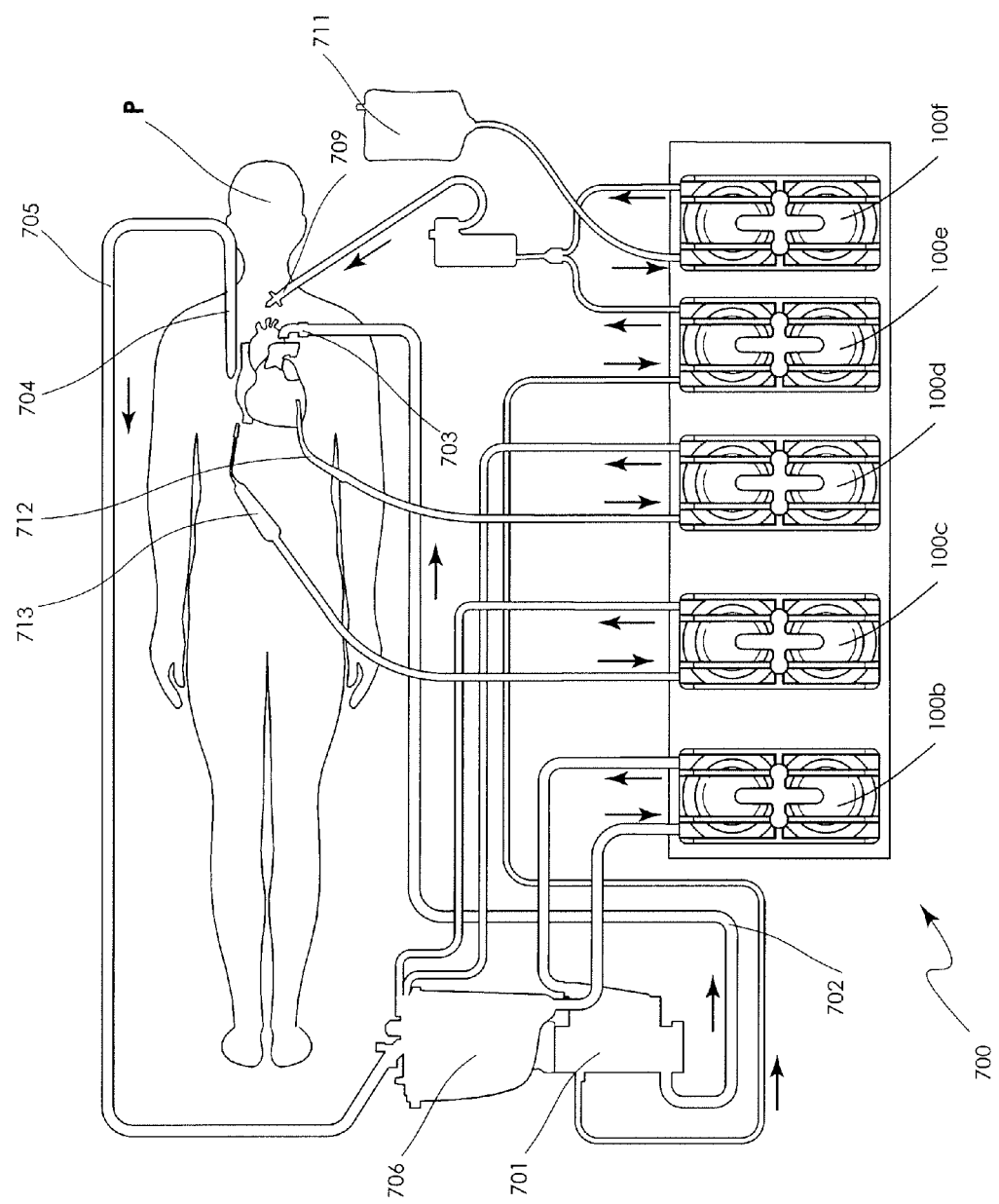
FIG. 17 is a schematic view of an embodiment of a cardiopulmonary by-pass system that includes multiple double diaphragm pumps.
Figure 18:
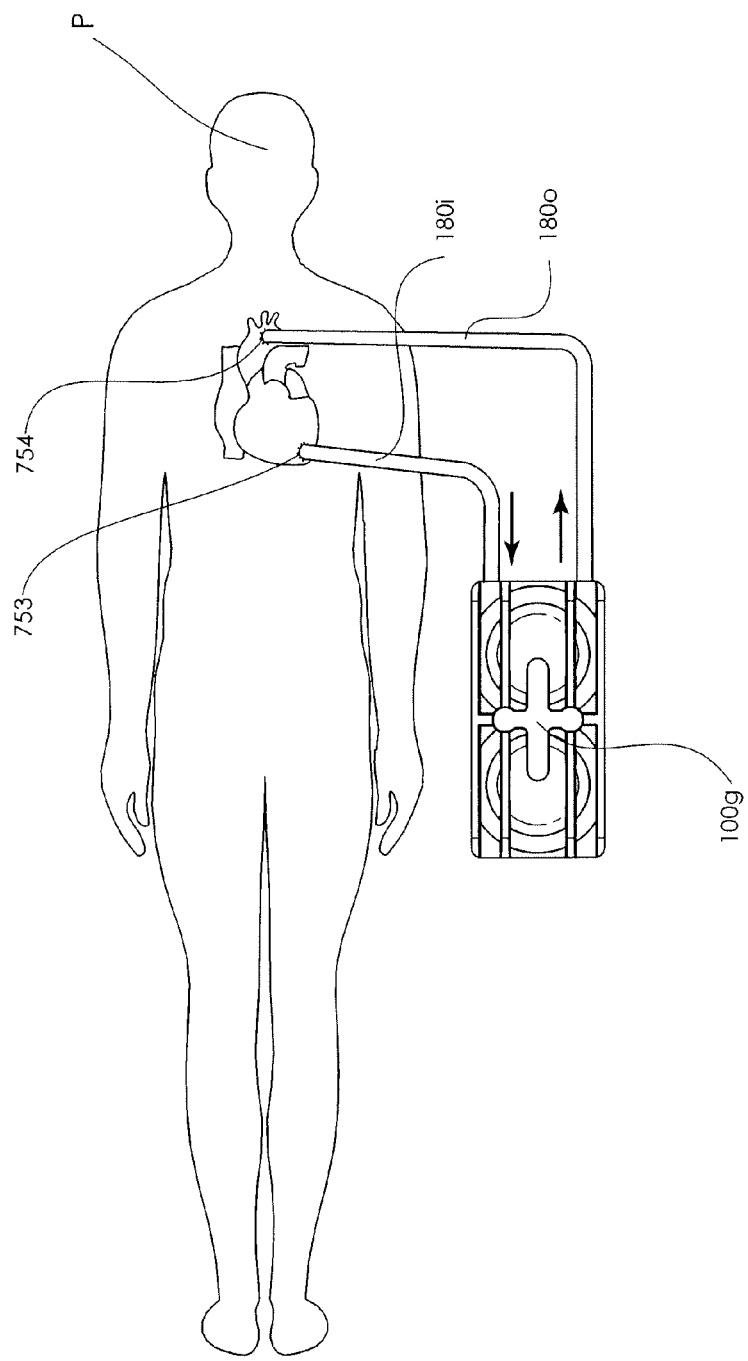
FIG. 18 is a schematic view of an embodiment of a heart-assist system using an embodiment of the double diaphragm pump.
Figure 19:
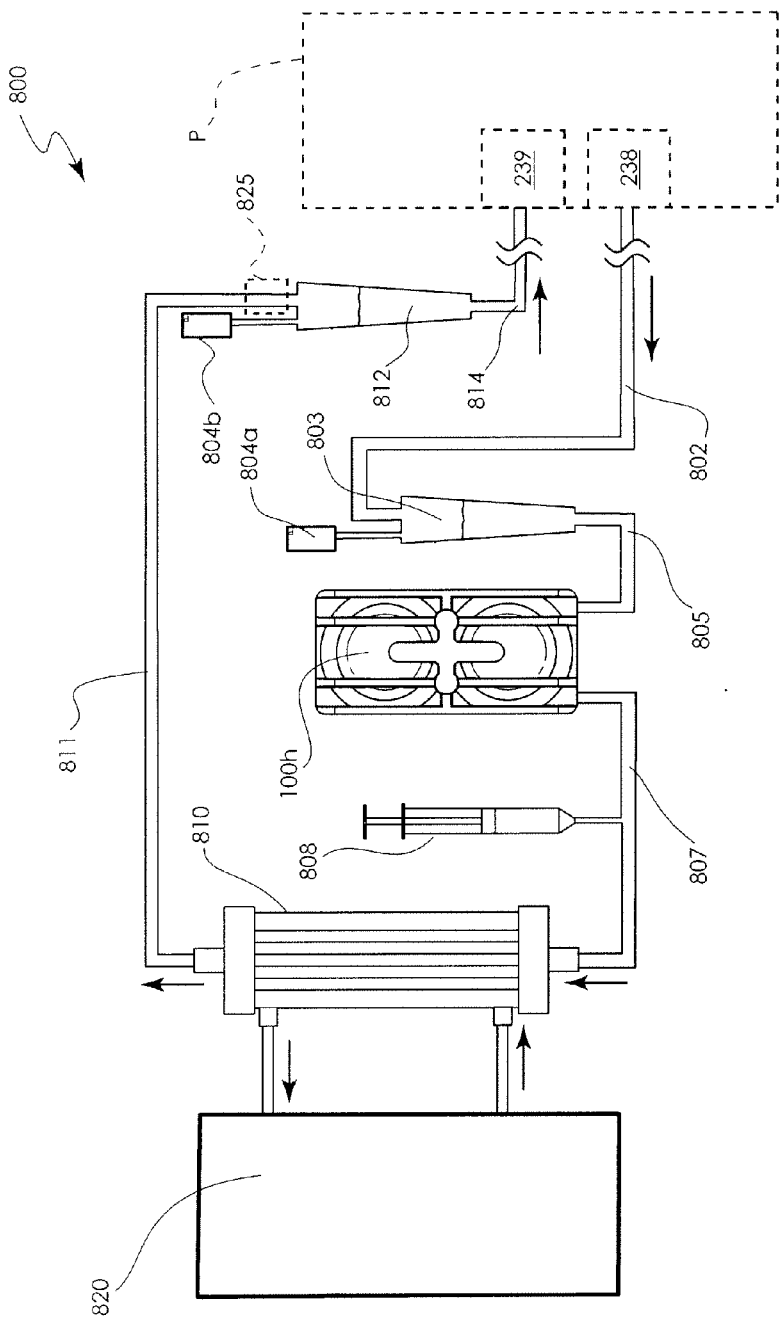
FIG. 19 is a schematic view of an embodiment of a hemodialysis system using an embodiment of the double diaphragm pump to effect flow through the system.

This disclosure relates to a pump apparatus and related methods and systems. Various views of an illustrative embodiment of a pump are provided in FIGS. 1-6B and 9A-11. FIGS. 7-8B relate to an embodiment of a forming fixture used to shape regions of a chamber diaphragm which can be used in a pump. An embodiment of pumping system utilizing a double diaphragm pump is shown in FIGS. 12-15. FIG. 16 provides a schematic view of an embodiment of a system utilizing a double diaphragm pump. The schematic views provided in FIGS. 17-19 illustrate various applications of embodiments of double diaphragm pumps in medical applications in which blood is pumped.

It is noted that similar or duplicate features are referred to with a unique alphanumeric designation. Certain features common to various embodiments may be designated with a primed numeral in some figures. In either case, duplicate elements will not be described in further detail to the extent their performance is similar to the embodiments previously described. For example, the chamber diaphragms illustrated in FIG. 2 will be referred to as 140a and 140b, and various diaphragm blood pumps are referred to in FIG. 17 as 100b, 100c, 100d, etc. A pump body in one embodiment is referred to in FIG. 9C as 110 and a pump body in another embodiment is referred to in FIG. 10 as 110'.

Certain diaphragm pumps can have application as a single use disposable medical blood pump. For example, a pump can be used to move blood through an extracorporeal circuit. An advantage of pumping blood with certain pumps as described herein is that, in various embodiments, a relatively small amount, a minimal amount, a negligible amount, or even no amount of synthetic pump material particles is released into the flow of blood that is caused by rubbing, sliding, or straining of materials typically used in other types of pump mechanisms to energize fluid flow. Synthetic particulates generated by certain pumps that move fluids to and from a patient have the potential to create adverse health effects including embolisms or microembolisms in the vascular system. Further, the toxicity of materials introduced or generated by such pumps can be delivered to the patient and can be left residing in the vascular system of the patient.

Certain embodiments of a pneumatically actuated diaphragm pump can be advantageous because of the inherent control that may be achieved for delivering fluids within physiologically acceptable pressure ranges. For example, if a blockage occurs in the process fluid lines connected to an embodiment of a pump, some embodiments of the pump may only generate pressure in the process fluid at a level that is at or near those of the motive fluid pressures that are driving the pump. In the case of pumping blood, such a pump can reduce or eliminate excessive pressures or high vacuums in the fluid lines that can potentially damage blood or cause air embolisms by out-gassing the blood under high suction levels.

Some embodiments of pumping systems that may be used in single-use disposable medical applications can advantageously be comprised of a removable and/or separable disposable pumping component and a reusable pump control system. The disposable pumping component can be packaged and pre-sterilized for use in a medical application related to an individual patient. In some embodiments, the disposable pumping component can be coupled in operative association with the reusable pump control system for a single patient during a medical application, and then removed and disposed.

In some embodiments, the reusable pump control system can be isolated from the flow of biological fluids and may selectively control and operate a plurality of disposable pumping components-one or more for each of a multiple number of patients or applications, in some instances-without being sterilized between uses. The removable/disposable pumping component may include pump chambers, inlet and outlet valves, inlet and outlet lines, and other components which are in contact with the blood or biological fluid. In some embodiments, the removable/disposable pumping component comprises a double diaphragm pump. As discussed below, in some embodiments, the double diaphragm pump can be configured and designed with a plurality of pump chambers, flow paths, valves, etc. that are specifically designed for a particular application. For example, some embodiments of double diaphragm pumps can be configured for use in such medical applications as cardiopulmonary bypass, surgical perfusion support, heart assist, and hemodialysis, as further described below.

Various embodiments of double diaphragm pumps also enable fluids to be transferred in a wide variety of other fields. For example, such pumps can be used in the transfer of high purity process fluids. Some embodiments of double diaphragm pumps can be advantageous in transferring high purity process fluids, as the pump avoids, minimizes, or otherwise reduces the introduction or generation of contaminants or particulate matter that can be transferred downstream by reducing or eliminating rubbing and sliding components within the pump. Downstream transfer of contaminants or particulate matter may effect the desired outcome of using the high purity process fluid. Also for shear sensitive fluids, some pumps can be operated to gently move fluid from a source to a destination.

Figure 2:
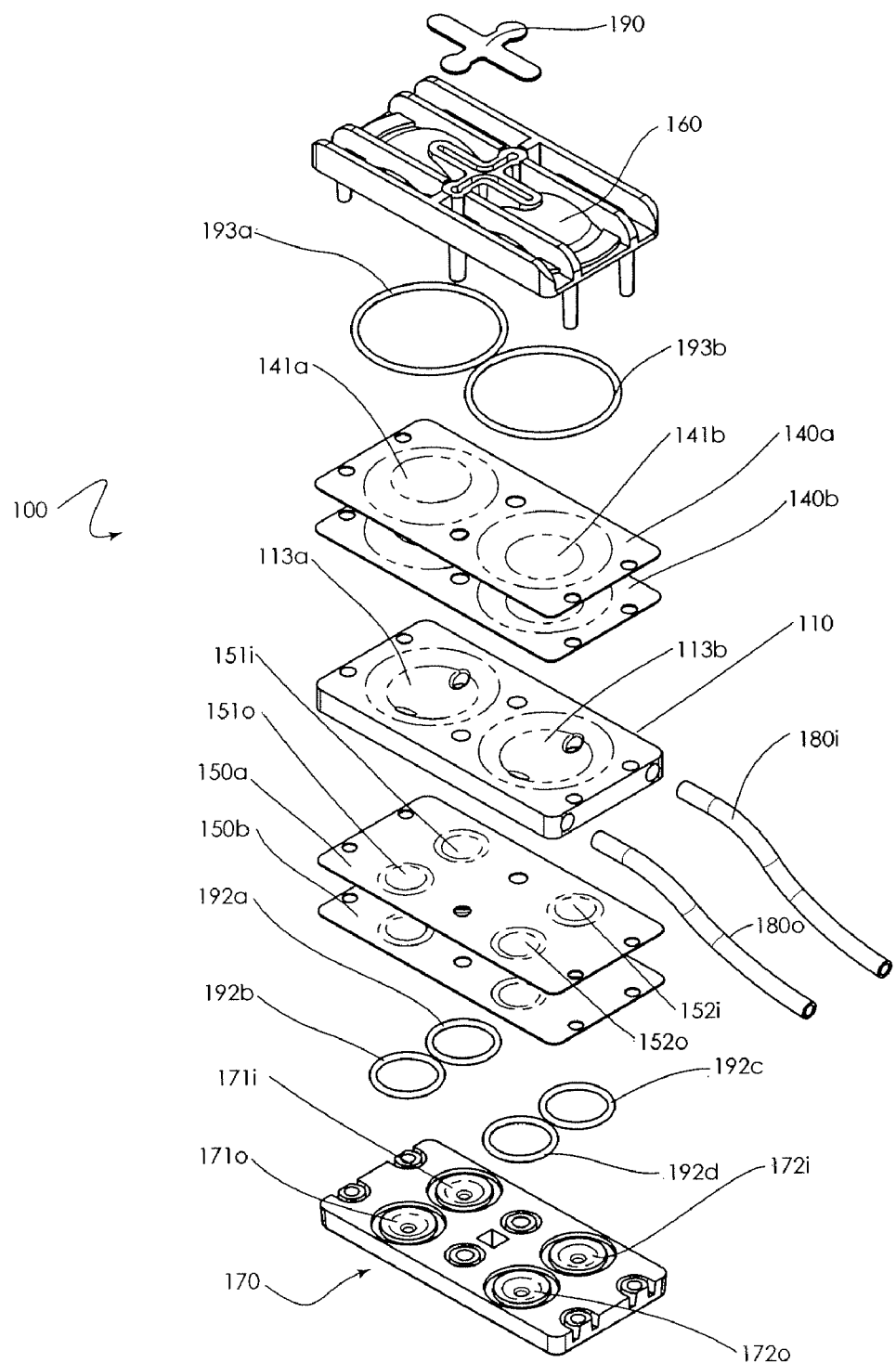
FIG. 2 is an exploded perspective view of the double diaphragm blood pump of FIG. 1.

FIG. 1 provides a perspective view of an embodiment of a double diaphragm pump at 100. The pump 100 can comprise a plurality of housing members or housing components, which in some embodiments may be substantially rigid, as discussed below. In some embodiments, the housing members comprise a pump body 110, a chamber plate 160 and a valve plate 170. In some embodiments, the pump 100 further comprises a plurality of diaphragms. For example, in some embodiments, the pump 100 comprises one or more chamber diaphragms 140a, 140b, which can be located between chamber plate 160 and pump body 110, and further comprises one or more valve diaphragms 150a, 150b, which can be located between valve plate 170 and pump body 110. The chamber diaphragms 140a, b and valve diaphragms 150a, b are not identified in FIG. 1 but are shown in FIGS. 2, 9B, and 9C. While these diaphragms may not necessarily extend to the perimeter of pump body 110, chamber plate 160, or valve plate 170, in some embodiments, the media can extend to the perimeter or beyond so that the media protrudes beyond an outer edge of the pump body 110. As further discussed below, in some embodiments, manifold cover plate 190 seals or closes motive fluid passages defined by chamber plate 160.

Figure 4:
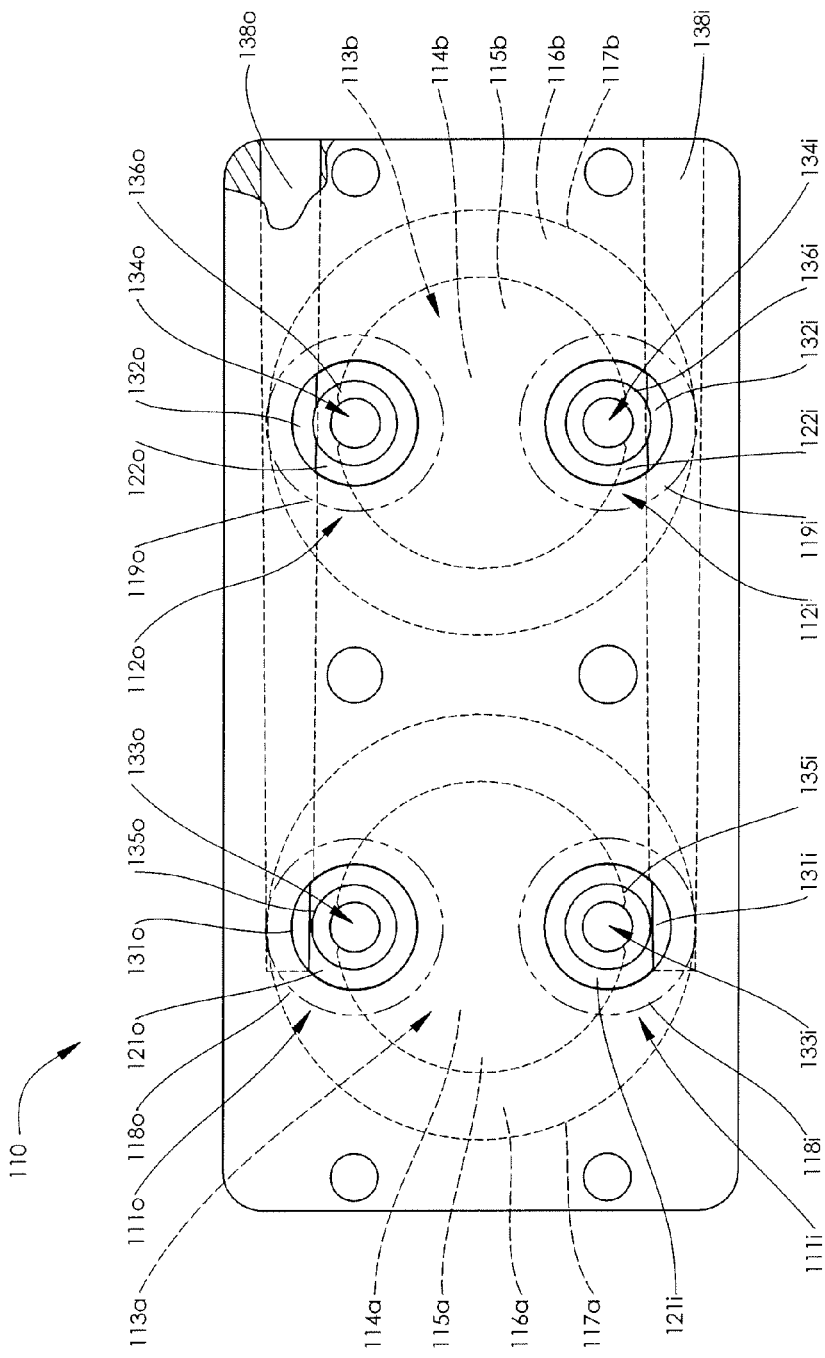
FIG. 4 is a plan view of one side of an embodiment of a pump body with a portion of the interior of the pump body shown in phantom and a portion of an opposite side of the pump body shown in phantom.

FIG. 1 and FIG. 4 show features related to the inlet and outlet lines for the passage of process fluid through the pump body 110. In particular, inlet line 180i is connected with inlet channel 138i and outlet line 180o is connected with outlet channel 138o, as shown. Inlet channel 138i and outlet channel 138o are shown in more detail in FIG. 4, FIGS. 9B-10 and FIG. 16. In the embodiment illustrated in FIGS. 1 and 4, representative connections between inlet line 180i and inlet channel 138i and between outlet line 180o and outlet channel 138o are shown. Similar connections can be made to other external fluid lines or devices. The connection between these components can include solvent bonding, adhesives, mechanical fittings (including barbed nipple tube fittings), or other methods well known in the art.

Some of the components which comprise the valves and the pump chambers are shown in FIG. 2, however, the valves and the pump chambers are not identified in FIG. 2, as this figure represents an exploded perspective view of a double diaphragm pump 100. As illustrated in FIGS. 9B-9C and FIG. 10, certain embodiments of the double diaphragm pump 100 can comprise a first inlet valve 101i, first outlet valve 101o, second inlet valve 102i, second outlet valve 102o, first pump chamber 103a, and second pump chamber 103b. FIG. 2 also shows a plurality of valve seals or o-rings 192a-d and chamber seals or o-rings 193a, b, which can be used in some embodiments to assist in sealing valves and pump chambers. For example, in some embodiments, the valve plate 170 comprises grooves 177i, 177o, 178i, and 178o (see FIG. 3) for receiving o-rings 192a-d. Similarly, chamber plate 160 can comprise grooves for receiving o-rings 193a, b.

Other means of sealing the valves and chambers can also be used, including adhesives, heat bonding, and welding. In certain embodiments, the diaphragms 140a, b and 150a, b and pump body 110 can be fabricated with similar materials that will bond together when heated. In some embodiments, fluorinated ethylene propylene (FEP) materials can be used for both of the diaphragms 140a, b, 150a, b and the pump body 110, and heat can be used to bond the diaphragms to the body. Other heat sealable materials that can be used for both of the diaphragms 140a, b, 150a, b and the pump body 110 include polyvinylchloride (PVC), polyurethane (PU), and polypropylene (PP). In some embodiments, an adhesive, such as Scotch Weld Acrylic DP-8005 adhesive manufactured by 3M—Industrial Business, Industrial Adhesives and Tapes Division, St. Paul, Minn., is used to attach the chamber plate 160 assembly posts 169a-d and air bosses 162a, b (see, e.g., FIG. 5) to the valve plate 170 assembly holes 179a-f (see, e.g., FIG. 3). Components of a double diaphragm pump 100, such as the components shown in FIG. 2 can be assembled together in any other suitable manner, such as via mechanical fasteners (for example nuts and bolts, clamps, screws, etc.); adhesives; welding; bonding; or other mechanisms. These mechanisms are all examples of means for maintaining the plates and body together and sealing chambers created between the plates and body.

FIG. 2 provides the best view of the chamber diaphragms 140a, b and valve diaphragms 150a, b. In the illustrated embodiment, each diaphragm 140a, b and 150a, b has a specific region corresponding with a particular chamber. In some embodiments, the regions are preformed or pre-shaped prior to assembly of the pump 100. In some embodiments, a single diaphragm is used between pump body 110 and chamber plate 160 and/or a single diaphragm is used between pump body 110 and valve plate 170. In other embodiments, two or more diaphragms are utilized between one or more sets of neighboring components, which can provide a pump 100 with one or more redundant layers for safety purposes. For example, in the unlikely event that one of the diaphragms were to fail due to a rare manufacturing defect, interaction with a sharp object in the air or fluid flow, cyclic fatigue cracking, or other cause of failure, the pump could safely operate using a redundant diaphragm. In some embodiments, each chamber or valve uses a separate diaphragm or diaphragms that are not integrated into a multi-chamber diaphragm. Additionally, the separate diaphragms can also include preformed or pre-shaped actuation regions. In some embodiments, the actuation regions are configured to move between a natural shape and an inversion of the natural shape without significant stretching, as further discussed below. The actuation regions can be configured to flex, in some embodiments. Methods for forming diaphragms with pre-shaped regions are discussed below with reference to FIGS. 6A, 6B, 7, 8A, and 8B.

In certain embodiments, the preformed actuation regions of chamber diaphragm 140a include first pump chamber region 141a and second pump chamber region 141b. The preformed actuation regions of valve diaphragm 150a include first inlet valve region 151i, first outlet valve region 151o, second inlet valve region 152i, and second outlet valve region 152o. Each media 140a, b and 150a, b can also have holes 142a-f (see FIG. 6A) for manufacturing and assembly, as further discussed below.

With reference to FIGS. 2, 9B, and 9C, first pump chamber 103a is divided by first pump chamber region 141a into first pump chamber cavity 113a and first actuation cavity 161a. Similarly, second pump chamber 103b is divided by second pump chamber region 141b into second pump chamber cavity 113b and second actuation cavity 161b. Each of the valves 101i, 101o, 102i, and 102o is also divided by its respective diaphragm regions. In particular, each of valves 101i, 101o, 102i and 102o comprises an actuation cavity and a valve seat. The valve seats include first inlet valve seat 111i, first outlet valve seat 111o, second inlet valve seat 112i, and second outlet valve seat 112o. The actuation cavities include actuation cavity 171i of first inlet valve 101i, actuation cavity 171o of first outlet valve 101o, actuation cavity 172i of second inlet valve 102i and actuation cavity 172o of second outlet valve 102o. Together, a given valve seat/actuation cavity pair can define a valve chamber through which a diaphragm region can move. For example, with reference to FIG. 9B, the first outlet valve region 151o can move within a valve chamber that is comprised of the first outlet valve seat 111o and the actuation cavity 171o.

The flow paths of the process fluid in some embodiments of the double diaphragm pump 100 are described below with reference to FIG. 4 and FIG. 16. The flow path is also described with reference to FIGS. 9A-10. Before providing a comprehensive overview of the flow path, the components of double diaphragm pump 100 are described below with occasional reference to the flow path. However, it should be understood that a process fluid is pumped into and out of first pump chamber 103a and second pump chamber 103b so that the process fluid enters and exits pump body 110. It should also be understood that the different regions of the diaphragm media are moved by alternating applications of pressure and vacuum to the pump chambers and valves to pump the process fluid into and out of pump chambers 103a and 103b and allow or prevent flow through valves 101i, 101o, 102i, and 102o. The pressure and vacuum can be provided by one or more fluids (also referred to as motive fluids) at differing pressure levels. In many embodiments, the motive fluids used with a pump 100 comprise air. Accordingly, reference throughout this disclosure may be made to "air" when describing the movement of motive fluid or when describing components associated with and/or that contact motive fluid during operation of a pump 100. Such references are not intended to be limiting, but rather, are made only to facilitate the discussion herein. For any such reference, other suitable fluids are also possible, such as, for example one or more liquids and/or gases.

In certain embodiments, different regions of the chamber diaphragms 140a and 140b and valve diaphragms 150a and 150b can be moved by applying pressure of the motive fluid which is greater than the pressure of the process fluid at the process fluid destination, receiver, or return 239 (see FIG. 16) and alternating with application of pressure of the motive fluid which is less than the pressure of the process fluid at the process fluid source 238 (see FIG. 16).

The amount of pressure or vacuum applied can vary significantly depending on the intended use of the pump 100. For example, in some embodiments, the double diaphragm pump 100 delivers a fluid at a pressure in a range of between about 0 mmHg (millimeters of mercury) and about 1500 mmHg, between about 50 mmHg and about 500 mmHg, between about 50 mmHg and about 700 mmHg, or between about 80 mmHg and about 500 mmHg. Similarly, in some embodiments, the double diaphragm pump 100 may receive fluid from a source or generate suction in a range of between about −500 mmHg and about 0 mmHg, between about −250 mmHg and about 0 mmHg, between about −120 mmHg and about 0 mmHg, or at an amount that is less than the fluid pressure at the process fluid source 238.

In some embodiments of the double diaphragm pump 100 that are configured to be used as a blood pump, blood is received into the pump and delivered from the pump in a range between about −250 mmHg and about 500 mmHg. While blood pressure in a patient vasculature system is typically in a range of 0 mmHg to 200 mmHg, depending on the location of blood in the system and condition of the patient, the blood pump 100 may operate at higher pressures and with vacuum assisted suction to overcome pressure losses in the extracorporeal circuit. These pressure losses can occur as blood flows through cannulae, connection lines, blood treatment devices, filters, reservoirs, and connectors. The blood pump may be operated to cause the blood to be drawn from and return to the patient vascular system at safe levels. These safe levels of blood pressure at the fluid source 238 may be above 0 mmHg and the blood pressure at the fluid return 239 may be below 150 mmHg. The blood may also be drawn into the pump without a vacuum source supplied to the pump (e.g., by application of about 0 mmHg relative pressure via a vacuum source or vent 230). Gravity feed into the pump may also be used to assist in filling the pump chambers. For example, in some embodiments, the process fluid source 238 is at an elevated pressure and at an elevated location from the pump and the resultant blood pressure at the pump causes the pump valves and chambers to vent the motive fluid and actuate the diaphragms when the pressure source 220 is removed (e.g., about 20 mmHg relative to atmosphere and located 24 inches higher in elevation). A motive fluid at a pressure higher than the elevated pressure of the blood entering the pump and also higher than the pressure at the fluid return 239 can be used to operate the pump and expel the process fluid from the pump 100 to deliver blood through an external circuit to the process fluid return 239 at acceptable physiological pressures (e.g., in some cases at about an average pressure of 80 mmHg).

Figure 3:
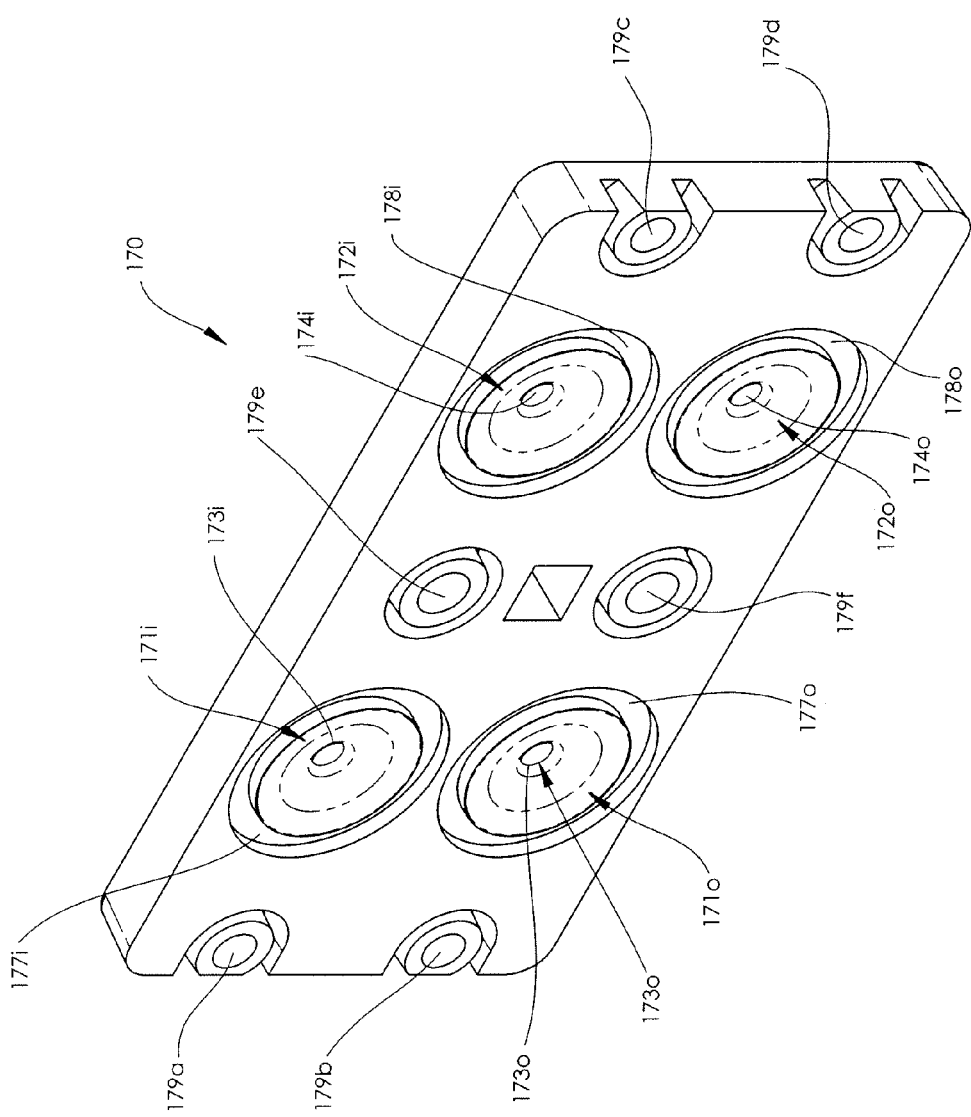
FIG. 3 is a perspective view of an inner side of an embodiment of a valve plate.

FIG. 3 and FIGS. 9B-9C show actuation cavity 171i of first inlet valve 102i, actuation cavity 171o of first outlet valve 102o, actuation cavity 172i of second inlet valve 102i, and actuation cavity 172o of second outlet valve 102o. Passages 173i, 173o, 174i, and 174o provide fluid communication to the actuation cavities through the air transfer bosses 176a-d. The air transfer bosses 176a-d may also be referred to as connections, connectors, posts, protrusions, interfaces, passageways. These terms can also be used to describe other bosses described herein.

Figure 5:
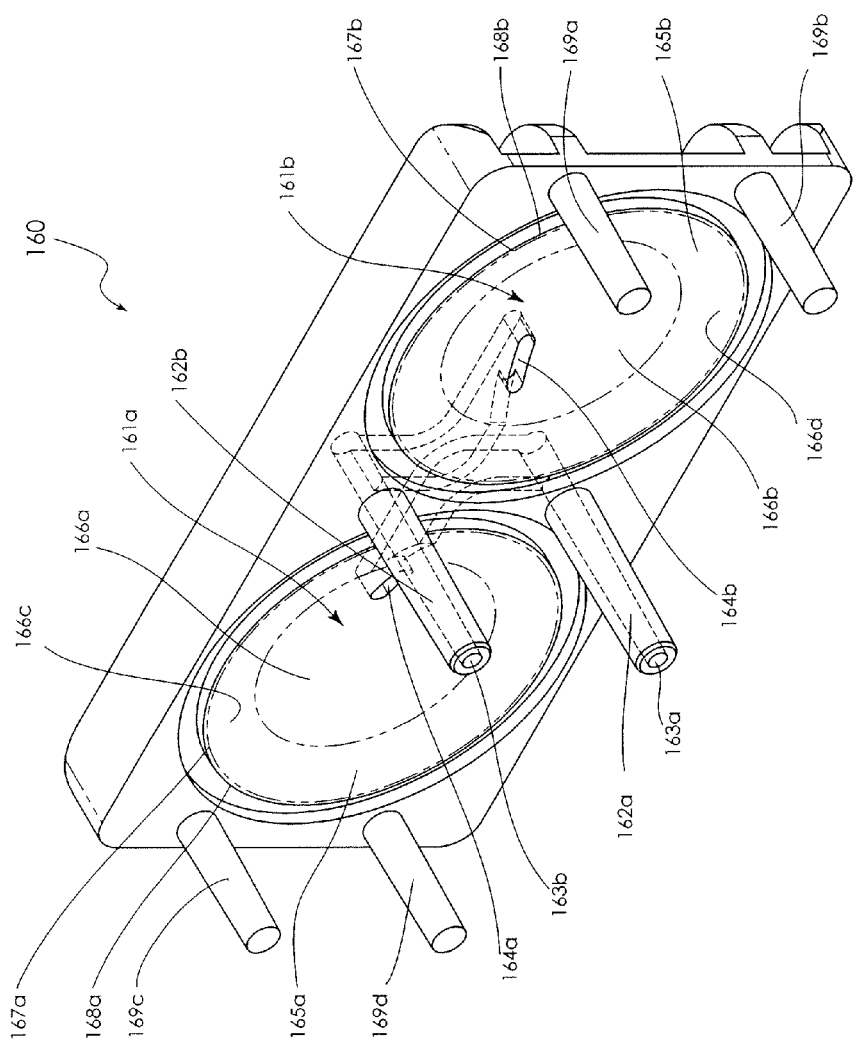
FIG. 5 is a perspective view of the inner side of an embodiment of a chamber plate with interior features thereof shown in phantom.

FIG. 5 shows the chamber plate 160, which can include first chamber actuation cavity 161a and second chamber actuation cavity 161b. The chamber plate 160 can include passages 163a and 163b. As shown, for example, in FIG. 1, the manifold plate 190 can be sealed over passages 163a and 163b. With reference again to FIG. 5, passage 163a provides fluid communication to actuation cavity 161a via opening 164a, and passage 163b provides fluid communication to actuation cavity 161b via opening 164b.

In certain embodiments, actuation cavities 161a, b are defined by cavity surfaces 165a, b that extend to outer perimeters 168a, b, respectively. The cavity surfaces 165a, b can include recesses 166a, b, respectively. An edge of each recess 166a, b is shown with dashed lines in the embodiment illustrated in FIG. 5. In some embodiments, one or more of the recesses 166a, b are substantially rounded, and may be concavely rounded. The cavity surfaces 165a, b can include inclined regions 166c, d that extend from the recesses 166a, b and outer rims 167a, b of the actuation cavities 161a, b, respectively. In some embodiments, the inclined regions 166c, d are also rounded, and may be convexly rounded. In some embodiments, rounded recesses 166a, b and rounded inclined regions 166c, d can limit the mechanical strain and increase cyclic life induced by limiting the minimum radius of bending curvature of the integrated diaphragm media 140a, b in the diaphragm actuation region 141a, b between the constrained edge of the diaphragm actuation region and a slope inflection point of the diaphragm actuation region as the diaphragm actuation region 141a, b transitions between end-of-stoke positions.

FIG. 4 shows a plan view of a first face or a first side of pump body 110, and illustrates first inlet valve seat 111i, first outlet valve seat 111o, second inlet valve seat 112i and second outlet valve seat 112o. First pump chamber cavity 113a and second pump chamber cavity 113b, which are located on the opposite face or side of pump body 110, are shown in phantom. Each valve seat has a groove 121i, 121o, 122i, 122o around a corresponding rim 135i, 135o, 136i, 136o. A valve portal 131i, 131o, 132i, 132o provides fluid communication between each valve seat and its corresponding line. For example, inlet channel 138i, which is shown in phantom, is in fluid communication with first inlet valve portal 131i and second inlet valve portal 132i. Similarly, outlet channel 138o, which is also partially shown in phantom and partially shown in the broken section view, is in fluid communication with first outlet valve portal 131o and second outlet valve portal 132o.

Chamber passages or channels 133i and 133o provide fluid communication respectively between first inlet valve seat 111i and first pump chamber cavity 113a and between first outlet valve seat 111o and first pump chamber cavity 113a. Similarly fluid communication between second inlet valve seat 112i and second pump chamber cavity 113b and between second outlet valve seat 112o and second pump chamber cavity 113b is achieved, respectively, via chamber channels 134i and 134o. This configuration permits first inlet valve seat 111i and second inlet valve seat 112i to be in fluid communication with inlet channel 138i and to alternatively receive process fluid. Similarly, first outlet valve seat 111o and second outlet valve seat 112o are in fluid communication with outlet channel 138o and alternatively deliver process fluid.

FIG. 4 also shows other features of the pump chamber cavities 113a and 113b. Surfaces of each pump chamber cavity, which can be recessed surfaces, are identified respectively at 114a and 114b with an inclined region for each identified at 115a and 115b, respectively. A rim 116a, b and a perimeter 117a, b are also identified for each of the pump chamber cavities 113a, b, respectively. The perimeters of the valve seats are also shown in FIG. 4. The perimeter of first inlet valve seat 111i and the first outlet valve seat 111o are respectively shown in phantom and identified as 118i and 118o. The perimeter of second inlet valve seat 112i and the second outlet valve seat 112o are respectively identified at 119i and 119o.

With continued reference to FIG. 4 and, additionally, with reference to FIGS. 9B and 9C, in certain embodiments, the pump chamber cavities 113a, b can define a smooth transition from a face of the pump body 110 to the recessed surfaces 114a, b. For example, in some embodiments, the perimeters 117a, b of the pump chamber cavities 113a, b are located at a substantially planar face of the pump body 110. The rims 116a, b can be substantially rounded, and can provide a smooth transition from the planar face at the perimeters 117a, b to the inclined regions 115a, b.

Similarly, the valve seats 111i, 111o, 112i, 112o can define a smooth transition from a face of the pump body 110 to a more recessed portion of the pump body 110. For example, the valve seat 111i can smoothly slope inward from the perimeter 118i, which can be at a substantially planar first face of the pump body 110, toward a more recessed portion of the valve seat 111i that is closer to an opposite face of the pump body 110.

In certain embodiments, smooth, tangent, or rounded transitions such as just described can limit the mechanical strain by limiting the minimum radius of bending curvature of the diaphragm actuation region between the constrained perimeter of the diaphragm and a slope inflection point in the diaphragm as the diaphragm actuation region transitions between end-of-stoke positions. Reduced mechanical strain can result in a longer lifespan of the chamber diaphragms 140a, b and valve diaphragms 150a, b, in certain embodiments. In some embodiments, the diaphragms are constrained to flex at the smooth or rounded transitions (e.g., to flex over the rounded lips 116a, b). In some embodiments, the amount of strain induced in a flexing diaphragm is inversely related to the radius of curvature in these regions; as a result, longer mechanical life of the diaphragms can be achieved with relatively gradually sloping transition regions. In other embodiments, relatively sharp transitions in these regions can cause the diaphragm to flex across a plastic-like hinge. A diaphragm actuation region could incur high cyclic strain in certain of such embodiments, and might rapidly fail due to cyclic fatigue.

The valve diaphragms 150a, 150b can have additional support as the diaphragms rest on seat rims 135i, 135o, 136i, and 136o in a closed valve position, which can be at a position near a preformed dome height of the valve diaphragm valve regions 151i, 151o, 152i, 152o. If the diaphragm material is too stretchable or if the diaphragm valve regions 151i, 151o, 152i, 152o are formed with excessive dome heights, high strain plastic-like hinges can form on the edges of the seat rims, and may cause high cyclic strain and short cyclic fatigue life. In some embodiments, the diaphragm valves desirably actuate from an open to a closed position at a differential pressure less than that provided by the pressure source 220 and at a differential pressure level less (e.g., less negative) than that provided by the vacuum source 230 (see FIG. 16). This can allow the valves to quickly open and close prior to the pump chamber causing a substantial amount of process fluid to flow back through the closing valves.

In some embodiments, chamber diaphragms 140a, b and valve diaphragms 150a, b have actuation regions, which are pre-shaped or formed prior to assembly of the pump 100, as further discussed below. The actuation regions can protrude from a plane defined by a relatively flat portion of a diaphragm 140a, b, in some embodiments. In further embodiments, the actuation regions naturally protrude and/or are naturally rounded in a convex manner when in a first state or resting state, and can be transitioned to a concave orientation when in a second state or displaced state. The second state can be stable or metastable, in some embodiments, and the actuation regions can define a variety of other shapes in the first and/or the second states. In some embodiments, the actuation regions can be readily transitioned between the first and second states, and the regions can deform, flex, or otherwise change shape by application of a relatively small amount of pressure, as compared with a substantially flat diaphragm without actuation regions which is stretched to conform to the same shape of the first or second state of an actuation region.

Figure 6B:
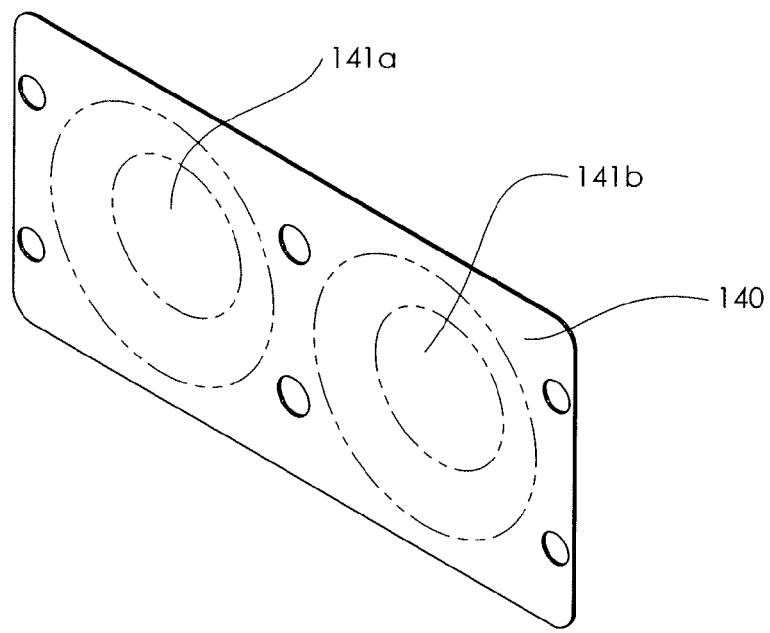
FIG. 6B is a perspective view of the diaphragm media of FIG. 6A after the regions have been formed.
Figure 7:
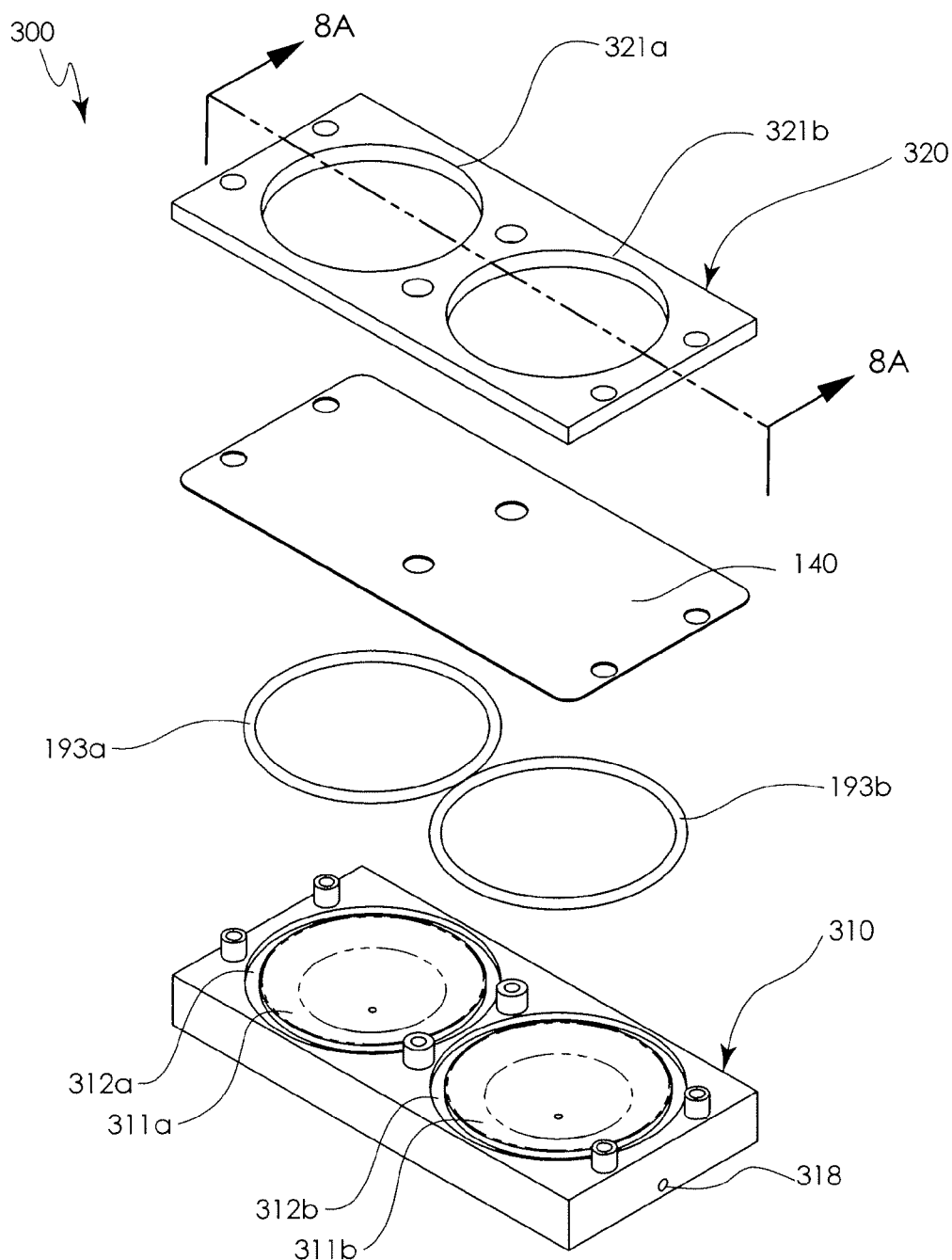
FIG. 7 is an exploded perspective view of an embodiment of a forming fixture used to form the regions in the diaphragm.

FIG. 6B depicts chamber diaphragm 140a after the formation of first pump chamber region 141a and second pump chamber region 141b. Preforming the chamber regions 141a, b of the chamber diaphragms 150a, b and the valve regions 151i, 151o, 152i, 152o of the valve diaphragms 140a, b can enable the valve regions to be seated and the chamber regions to move fluid into and out of the chambers based only on sufficient pressure (positive or negative) for movement of the regions, in some arrangements. Stated otherwise, after these regions of the diaphragm film material have been formed by, for example, heat forming or stretching, the regions can move in response to fluid pressure with low strain as each valve or chamber cycles like a fluid isolating membrane.

In some embodiments, the diaphragm regions are preformed in such a manner that the cord length of the valve regions and the chamber regions remains substantially constant while cycling. In other embodiments, the diaphragm regions stretch by a relatively small amount. One method to quantify diaphragm stretch is the change in cord length as the diaphragm flexes from end-of-stroke positions, where the cord length is the length of a cord if positioned on the surface of the diaphragm such that the cord extends from one point on the perimeter of the formed region and continues through the center point of the region to a second point on the perimeter of the formed region, with the first and second points being opposite from each other relative to the center point. For example, in various embodiments, the cord length can change by less than about 10%, less than about 5%, or less than about 3% during each pump cycle. The cord length can be sufficient to enable the diaphragm regions 150a, b and 151i, 151o, 152i, 152o to flex and pump the fluid in the pump chamber and to flex and controllably seal the fluid flow through the pump valves at the same or substantially the same pressures. By preforming the regions of the diaphragm media in some embodiments, the valve regions can be seated without application of additional pressure, as compared with the pressure used to move the region of the diaphragm within the pump chamber. By controlling the cord length of a diaphragm in certain embodiments, the mechanical cycle life of the diaphragm can be increased by minimizing material strain when flexing from one end-of-stroke condition to the other end-of-stroke condition, and the diaphragm can be capable of reaching the end-of-stroke condition without (or substantially without) the material of the diaphragm stretching. In certain embodiments, since pressure is applied for movement or is applied for movement and at most a nominal amount for stretching the preformed actuation regions, the amount of pressure needed to actuate the diaphragm region is low and the lifespan of the diaphragm media is extended due to the gentler cycling. In some embodiments, since material strain is reduced using thin film materials in the construction of the flexing chamber diaphragms 140a, b and valve diaphragms 150a, b, the material strain caused by in-plane stretching can be controlled by the support of the pump chamber and valve cavities at end-of-stroke conditions, and long mechanical life of the diaphragms can be achieved.

In certain embodiments, higher ratios of the maximum distance between opposing sides of a perimeter or perimeter width (e.g., the diameter of a circumference) of a diaphragm region 141a, b, 151i, 151o, 152i, 152o to a dome height of the region can promote long mechanical cyclic life of the diaphragms 140a, b, 150a, b without material fatigue failure. In some embodiments, the dome height of a region is defined as the maximum distance from a plane defined by a maximum perimeter of the region (e.g., a maximum circumference of the region) to any portion of the diaphragm material that comprises the region along a line normal to the plane. The term "dome height" is a broad term and is not limited to situations in which an actuation region 141a, b, 151i, 151o, 152i, 152o shaped substantially as a rounded dome. For example, a region having a substantially pyramidal configuration could also define a dome height.

In some embodiments, the diaphragm media is reshaped when traveling between end-of-stroke positions and the reshaping can cause the material to strain. With relatively low ratios between the perimeter width and the dome height of a region, the diaphragm material in some embodiments creates relatively sharp folds in order for the dome to move from one end-of-stroke condition to another which can cause relatively high material strain and a relatively short mechanical life for the diaphragm. With relatively high ratios between the perimeter width and the dome height of a region, the size of some embodiments of the double diaphragm pump 100 can be relatively large, which can increase material costs and other costs for manufacturing the pump 100.

In various embodiments, the ratio of the perimeter width to the dome height of the actuation regions 141a, b of the chamber diaphragms 140a, b is between 4:1 and about 30:1, between about 5:1 and about 20:1, or between about 6:1 and about 10:1. In some embodiments, the ratio is about 8:1. In certain of such embodiments, the actuation regions 141a, b have diameters of about 2.7 inches and dome heights of about 0.36 inches. For such embodiments, the actuation regions 141a, b can have a stroke volume of about 25 cubic centimeters (cc) when the dome moves from one end-of-stroke position to the other.

In various embodiments, the ratio of the diameter to the preformed dome height of the actuation cavities 171i, 171o, 172i, 172o of the valve diaphragms 150a, 150b is between about 4:1 and about 30:1, between about 5:1 and about 20:1, or between about 6:1 and about 10:1. In some embodiments, the ratio is about 8:1. In certain of such embodiments, the actuation cavities 171i, 171o, 172i, 172o have diameters of about 1.12 inches and dome heights of around 0.14 inches. For such embodiments, the actuation cavities 171i, 171o, 172i, 172o can have a valve actuation stroke volume of about 1.5 cubic centimeters (cc) when the dome moves from one end-of-stroke position to the other.

In certain embodiments, to actuate the chamber diaphragms 140a, b and valve diaphragms 150a, b from one end-of-stroke position to another, a certain pressure differential level between the fluid on one side of a diaphragm and the actuation chamber pressure on the other side of the diaphragm is provided to overcome the structural stiffness of the diaphragms. If the structural stiffness of the diaphragms is too high, the pressure used to actuate the regions 141a, b, 151i, 151o, 152i, 152o may exceed the desired operating pressure of the pump. However, some embodiments also benefit from the structural stiffness of the diaphragms not being too low. For example, in some embodiments, the diaphragms desirably have enough structural rigidity to not plastically deform under the operating pressures and also to bridge over regions of the diaphragms that are not supported at their end-of-stoke positions.

In various embodiments, the differential pressure used to actuate the chamber diaphragms 140a, 140b and valve diaphragms 150a, 150b is in a range of between about 5 mmHg and about 200 mmHg, between about 20 mmHg and about 100 mmHg, or between about 30 mmHg and about 60 mmHg. In some embodiments, a relatively small initial pressure differential is sufficient to actuate preformed regions 141a, b, from a first end-of-stroke position to a second end-of-stroke position. In some embodiments, a relatively small initial pressure differential is sufficient to actuate preformed regions 151i, 151o, 152i, 152o from an open valve position to a closed valve position.

Once a valve is in the closed position, the valve can remain in the closed position so long as the fluid pressure that acts on one side of the associated region to maintain the valve in the closed position exceeds the fluid pressure on the opposite side of the region by an amount greater than the amount of pressure required to actuate the valve. For example, in some embodiments, the region 151o can be actuated from the closed valve position illustrated in FIG. 9B to an open valve position when the pressure in the first chamber cavity 113a exceeds the pressure in the actuation cavity 171o by an amount greater than the pressure required to move the region 151o out of the closed orientation. In various embodiments, a valve can be maintained in the closed position when a differential pressure on opposite sides of a diaphragm actuation region is less than about 300 mmHg, less than about 200 mmHg, less than about 100 mmHg, less than about 50 mmHg, less than about 25 mmHg, less than about 10 mmHg, less than about 10 mmHg, or is about 0 mmHg. Similarly, in various embodiments, a valve can be maintained in the open position when a differential pressure on opposite sides of a diaphragm actuation region is less than about 300 mmHg, less than about 200 mmHg, less than about 100 mmHg, less than about 50 mmHg, less than about 25 mmHg, less than about 10 mmHg, less than about 10 mmHg, or is about 0 mmHg.

Some embodiments can include diaphragms 140a, b, 150a, b that comprise elastomeric material in a flat sheet configuration. Certain of such embodiments, however, can exhibit performance characteristics that are not present or are much less pronounced in some embodiments that include diaphragms 140a, b, 150a, b having actuation regions 141a, b, 151i, 151o, 152i, 152o. For example, in some embodiments having a flat sheet configuration, operation of the pump can cause repeated in-plane stretching of diaphragm material as displacement volumes are created, which can cause a diaphragm to fail as a result of low cycle, high strain material fatigue. In some embodiments, the pressure and suction levels needed to stretch the material by an amount sufficient to actuate the valves can exceed the available pressure level in the pressure source 220 and/or the available vacuum level in the vacuum source 230 (see FIG. 16). Therefore, such embodiments might employ higher levels of pressure and vacuum to actuate the valves 101i, 101o, 102i, 102o to prevent the fluid pressures created in the pumping chambers 103a, b from overcoming the valve actuation pressures.

Further, variation in fluid pressures can be created in the pumping chambers 103a, b during a pumping stroke. In certain embodiments that include a sheet-like diaphragm without preformed actuation regions 141a, b, 151i, 151o, 152i, 152o, the diaphragm stretches to fill and discharge fluid and uses a dynamically changing portion of the pressure supplied to the pump chamber 103a, b in the stretching process. The pressure within the pump chamber as the chamber fills with fluid is related to the difference between the pressure supplied by a pressure source and the changing amount of pressure used to actuate and stretch the flat sheet diaphragm in its travel through a stroke. When the pump chamber discharges from a filled state, energy stored in the stretched diaphragm releases and increases the pressure supplied to the pump actuation chamber, which may result in pressure spikes in the outlet line 180o. In some embodiments, such pressure spikes can be undesirable. Similarly, when the pump chamber is filled from a discharged state, the energy stored in the stretched diaphragm releases and increases the suction supplied to the pump chamber 103a, b, which may result in suction spikes in the inlet line 180i. In some embodiments, such suction spikes can be undesirable. Some embodiments that include actuation regions 141a, b 151i, 151o, 152i, 152o thus can provide inlet line 180i and/or outlet line 180o pressures that have fewer spikes or fluctuations as a result of the actuation regions 141a, b, 151i, 151o, 152i, 152o transitioning between first and second states.

In certain embodiments, each of the diaphragms 140a, 140b, 150a, 150b is formed from a film having a substantially uniform thickness. The thickness of a diaphragm may be selected based on a variety of factors, such as the material or materials of which the diaphragm is composed, the size of the valve or chamber in which the diaphragm moves, etc. A diaphragm can be configured to separate a motive fluid from the process fluid during all stages of a stroke cycle and can be supported intermittently by surface features of the pump cavities (such as, for example, the seat rims 135i, 135o, 136i, 136o of the inlet and outlet valves 101i, 101o, 102i, 102o and/or the recesses 114a, b, 166a, b of the pump chambers 103a, b) when at an end of a stroke cycle. Accordingly, in some embodiments, the diaphragm media thickness is sufficiently thick to provide a substantially impermeable barrier between the process fluid and the motive fluid and to provide sufficient stiffness to resist substantial deformation when pressed against the surface features of the pump cavities. In some embodiments, the diaphragm thickness is also sufficiently flexible or pliable to transition between open and closed valve positions or between filled and discharged chamber positions with application of relatively small pressure differentials. In some embodiments, a thin diaphragm can have a lower level of mechanical strain when cycled between open and closed valve positions or between filled and discharged chamber positions than can a thicker diaphragm of otherwise like construction. The lower cyclic strain of a thin diaphragm can increase the lifespan of the diaphragm before mechanical failure of the material. In various embodiments, the diaphragm media has a thickness in a range between about 0.001 inches and about 0.060 inches, between about 0.002 inches and about 0.040 inches, between about 0.005 inches and about 0.020 inches, or between about 0.005 and about 0.010 inches.

In certain embodiments, higher ratios of minimum radius of bending curvature of the profile of the flexing portion of a preformed diaphragm to the diaphragm thickness may increase diaphragm cyclic life as the diaphragm transitions from one end-of-stroke position to another. In various embodiments, this ratio is in a range between about 5:1 and about 100:1, between about 10:1 and about 50:1, or between about 20:1 and about 30:1. In one embodiment, the diaphragm has a minimum radius of bending curvature of 0.25 inches and a diaphragm thickness of about 0.010 inches with a resulting ratio of 25:1.

FIG. 6A depicts an embodiment of a chamber diaphragm 140 before the regions 141a, 141b have been preformed or pre-stretched. In the illustrated embodiment, the diaphragm has been cut from a sheet of film. The diaphragm initially has a substantially uniform thickness and is then shaped to yield preformed or pre-stretched regions. FIG. 6B depicts chamber diaphragm 140 as it appears after being formed in forming fixture 300 as shown in FIGS. 7-8B. Other methods of forming actuation regions 141a, 141b in the diaphragm 140 are also possible, and the example described with respect to FIGS. 7-8B is merely provided by way of illustration.

FIGS. 7-8B depict the use of heat and vacuum to shape the regions 141a, b of a diaphragm 140. Many combinations of pressure, vacuum, and heat could also be used separately or together to form the regions in the diaphragms. For example, if only pressure is used, the residual stresses in the diaphragm shapes can cause the diaphragm form to change as the diaphragms are repeatedly cycled. In other embodiments, pressure is used to form the diaphragm regions and then the diaphragms are annealed by heating. For example, in some embodiments, the chamber diaphragms 140a, b are made of FEP film material that has a thickness of about 0.007 inches and a formed region perimeter of about 2.7 inches is overformed to a dome height of about 0.72 inches under pressure, then heated to approximately 60° C. for about 2 hours for a resulting dome height of about 0.36 inches. In a second example of pressure forming, in some embodiments, the chamber diaphragms 140a, b are made of PTFE film material that has a thickness of about 0.010 inches and a formed region diameter of 2.7 inches is overformed to a dome height of about 0.58 inches under pressure, then heated to approximately 60° C. for about 2 hours for a resulting dome height of about 0.36 inches. In various embodiments, the preformed diaphragm regions have a thickness in a range from about 0.001 inches to about 0.060 inches, from about 0.002 inches to about 0.040 inches, from about 0.005 inches to about 0.020 inches, or from about 0.005 to about 0.010 inches.

FIG. 7 depicts first plate 310 and second plate 320 of forming fixture 300 in an exploded view. Because forming fixture 300 is shown being used to produce a chamber diaphragm 140 (such as either of the diaphragms 140a or 140b), the o-rings depicted include o-rings 193a, 193b. First plate 310 can include chamber region recesses 311a, b that are circumscribed by o-ring grooves 312a, b. Plate 320 has portals 321a, b to allow heat to reach areas of the diaphragm that are being formed.

Figure 8A:
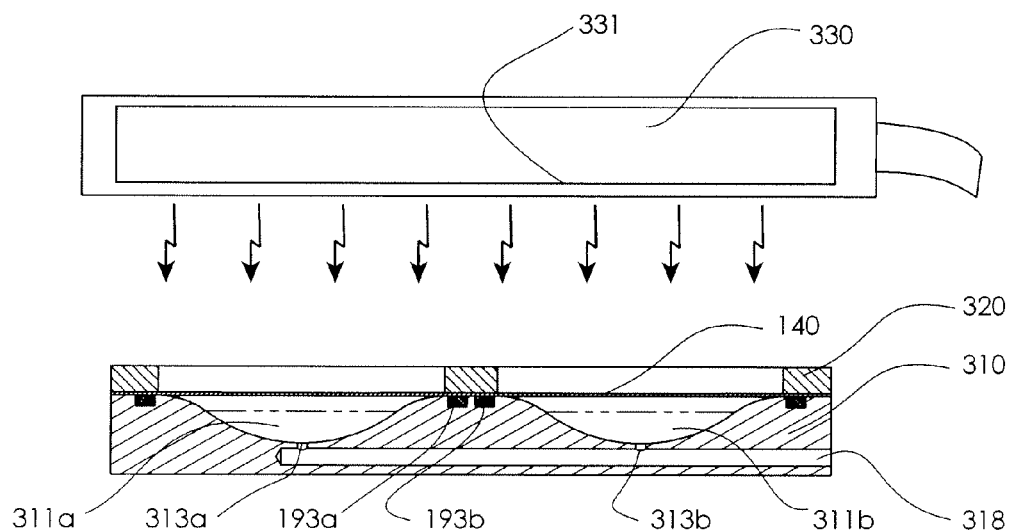
FIG. 8A is a cross-sectional view of a forming fixture after a diaphragm media has been loaded to form the regions in the chamber diaphragm.
Figure 8B:
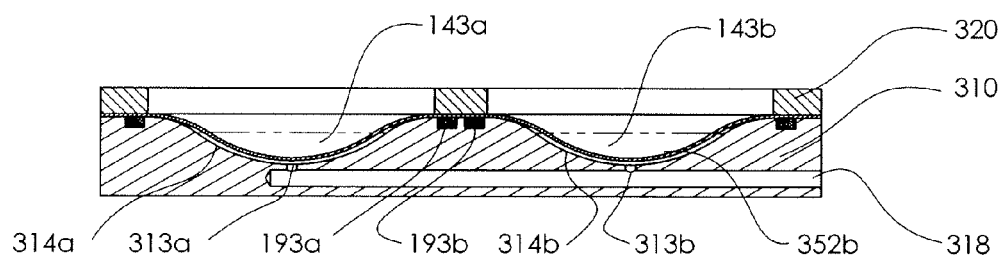
FIG. 8B is a cross-sectional view such as the view in FIG. 8A showing the forming fixture after the regions in the diaphragm media have been formed.

FIG. 8A shows a cross-sectional view of fixture 300 with a diaphragm media 140 between first plate 310 and second plate 320. The fixture 300 can be clamped together with mechanical fasteners or other assembly mechanisms to hold the diaphragm in position and seal the chambers created between the diaphragm and the chamber region recesses 311a, b. A vacuum is placed in fluid communication with these chambers via passage 318, which can include openings 313a, b into the chamber region recesses 311a, b, respectively.

A heater 330 (such as, for example, an infrared heater) is positioned to heat the regions of the diaphragm that are to be pre-shaped. In some embodiments, the diaphragm is substantially planar upon initial positioning between the first plate 310 and the second plate 310. The diaphragm film material can sag to a substantially non-planar configuration as it is heated and is exposed to a pressure differential, and the diaphragm material can conform to the surfaces 314a, b (see FIG. 8B) of the chamber region recesses 311a, b to form first pump chamber region 141a and second pump chamber region 141b. In some embodiments, the first plate 310 acts as a heat sink when regions of the diaphragm sag and come in contact therewith, and can prevent the diaphragm material from reaching a material transition temperature. Thus, in some embodiments, regions are fully formed after contact is made between the sagging portion of the diaphragm media and the first plate 310. FIG. 8B shows the fully formed chamber diaphragm 140 with the infrared heater removed.

In some embodiments, the chamber diaphragms 140a, b are made of FEP film material with a thickness of about 0.007 inches and assembled in a forming fixture 300 that is at a temperature of about 20° C. to about 40° C. In certain of such embodiments, a vacuum of about −10 psi is applied to passage 318 and an infrared heater 330 with a heater surface 331 operating at a temperature of 315° C. is positioned substantially parallel to and about 1.5 inches away from the surface of the flat diaphragm for about 1 minute. The heater is then removed. In certain embodiments, without being limited by theory, a diaphragm 140 formed via thermoforming techniques retains its shape as it is repeatedly cycled in the pump because internal stresses in the diaphragm material are relieved during the heat forming process.

While FIGS. 7-8B depict the forming of chamber diaphragm 140a and 140b, a forming fixture configured uniquely to form the valve diaphragm regions and similar to forming fixture 300 can be used to form valve regions 151i, 151o, 152i, and 152o in valve diaphragms 150a and 150b.

Figure 9A:
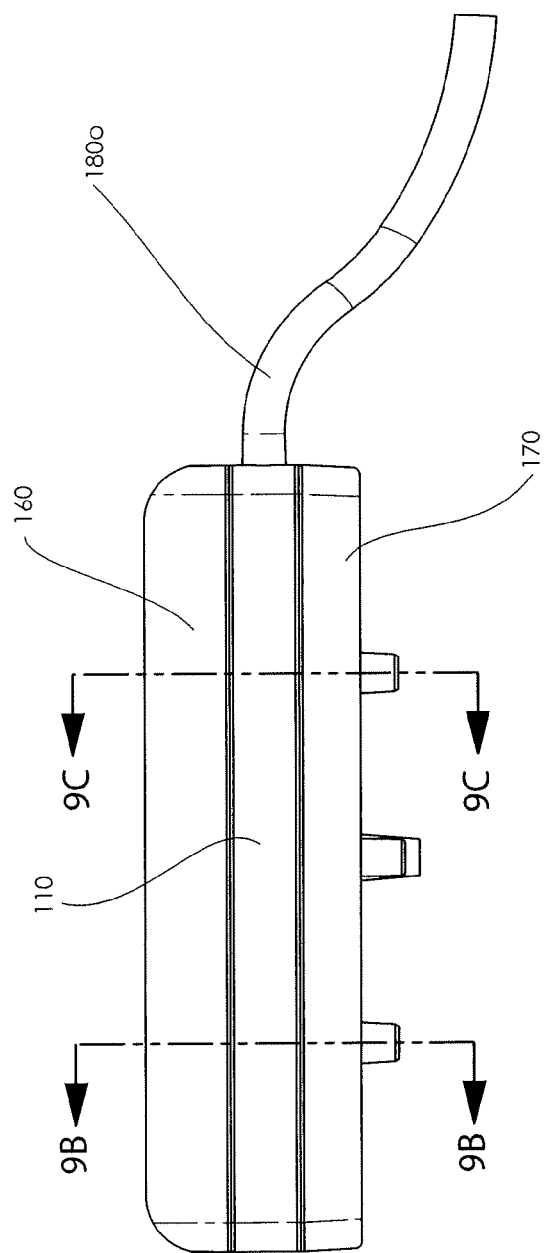
FIG. 9A is a side view of the double diaphragm pump of FIG. 1 which shows cutting lines 9B-9B and 9C-9C.
Figure 9B:
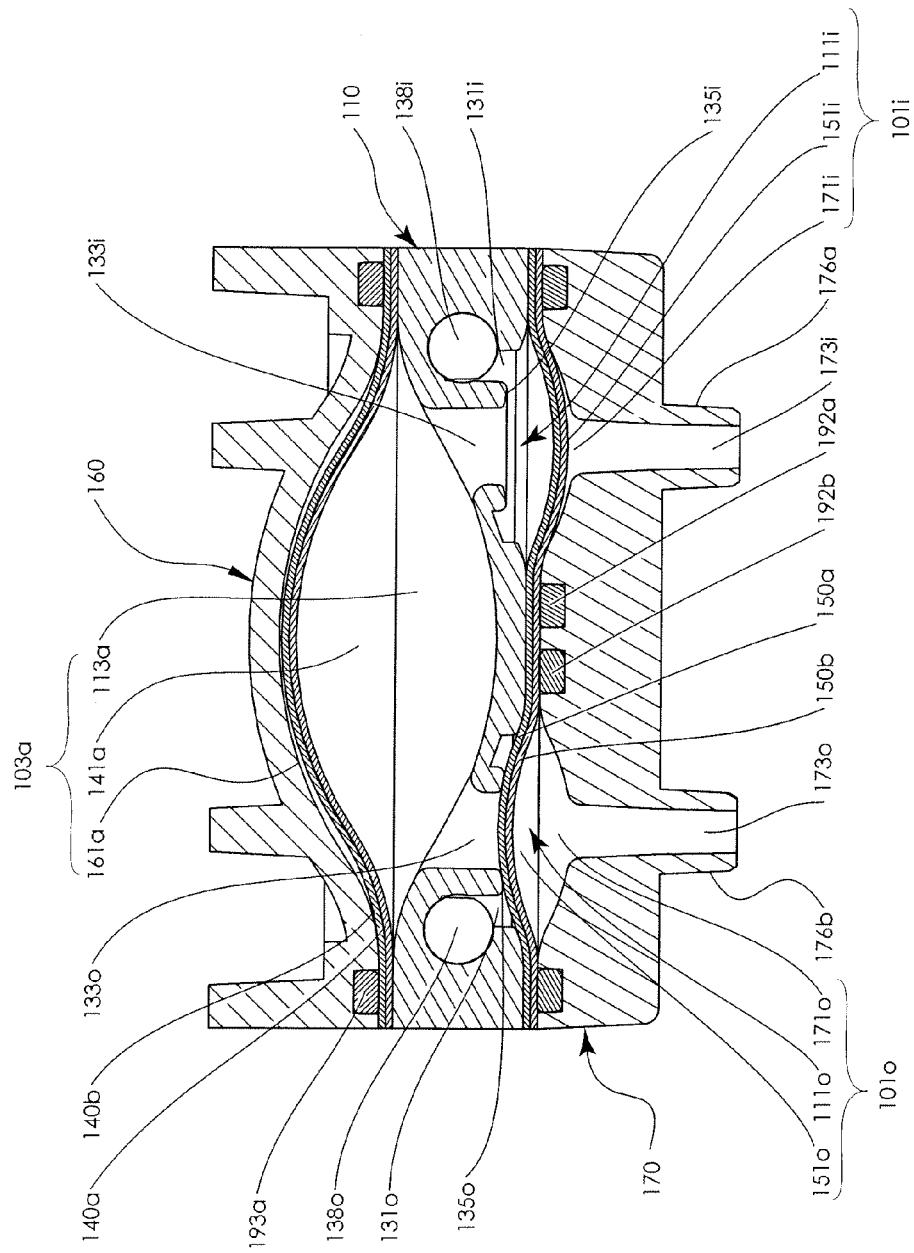
FIG. 9B is a cross-sectional view of the double diaphragm pump of FIG. 1 taken along cutting line 9B-9B in FIG. 9A.
Figure 9C:
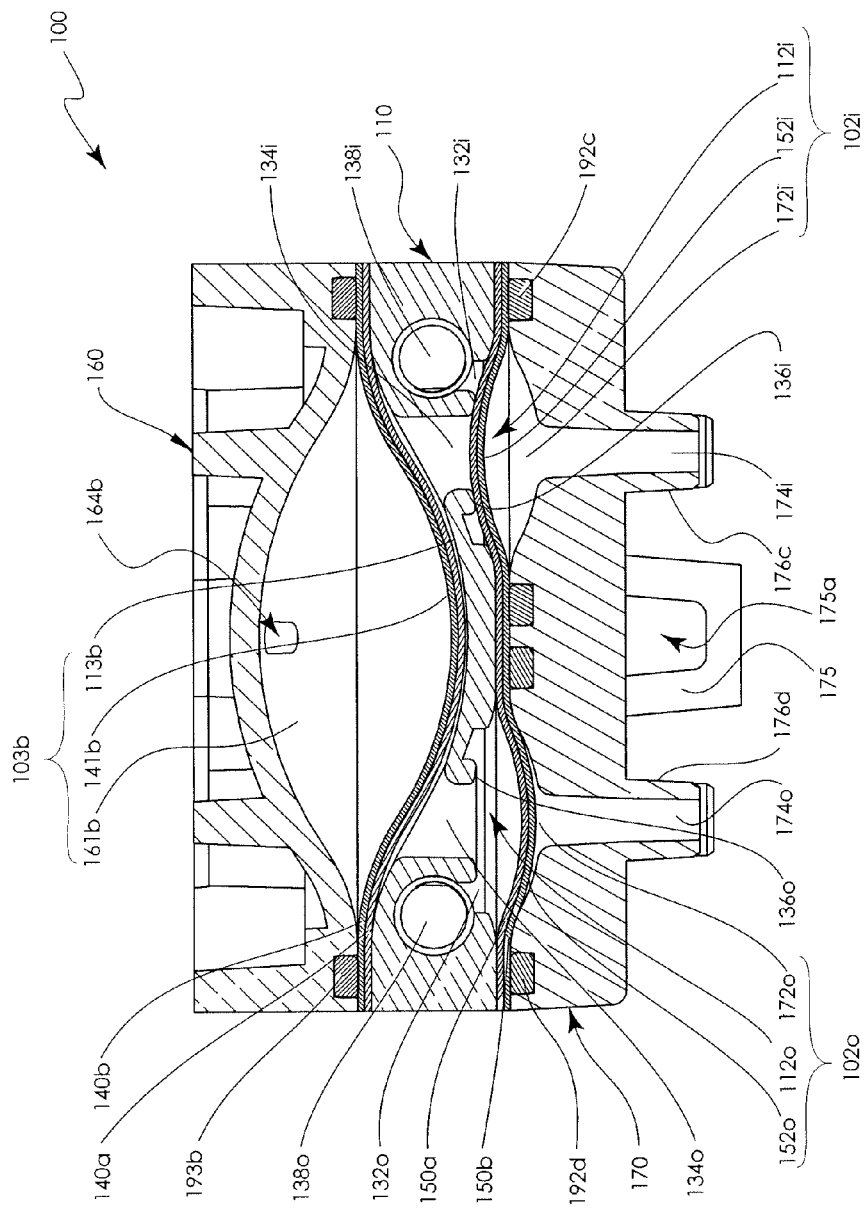
FIG. 9C is a cross-sectional view of the double diaphragm pump of FIG. 1 taken along cutting line 9C-9C in FIG. 9A.
Figure 10:
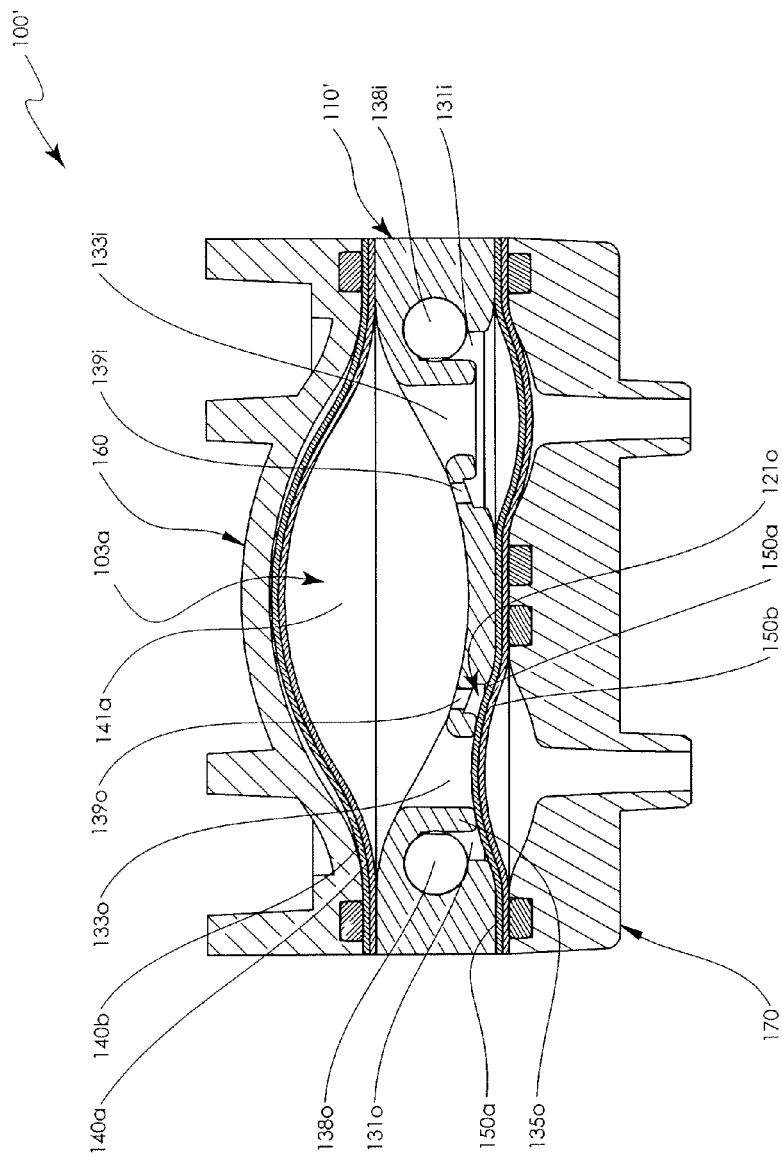
FIG. 10 is a cross-sectional view of another embodiment of the double diaphragm pump of FIG. 1 taken along cutting line 9B-9B in FIG. 9A showing valve bypass passages.

FIGS. 9B and 9C are transverse cross-sectional views taken along the cutting lines shown in FIG. 9A to show the operation of an embodiment of first inlet valve chamber 101i, first outlet valve chamber 101o, second inlet valve chamber 102i, second outlet valve chamber 102o, first pump chamber 103a, and second pump chamber 103b. FIGS. 9B and 9C also show the operation of first chamber diaphragm region 141a and second chamber diaphragm region 141b of chamber diaphragms 140a, b.

FIG. 9B shows first inlet valve chamber 101i, first outlet valve chamber 101o, and first pump chamber 103a at the end of a fluid draw stroke. In FIG. 9B, the first chamber diaphragm region 141a of chamber diaphragms 140a, b is shown at an end-of-stroke position, where pressure has been applied through passage 173o to first outlet valve chamber 101o and vacuum is supplied through passage 173i to first inlet valve chamber 101i and also through passage 163a, as identified in FIG. 5, to first pump chamber 103a. Pressure in first outlet valve chamber 101o causes outlet valve region 151o of valve diaphragms 150a 150b to move (e.g., flex) and rest on or in close proximity to first outlet valve seat rim 135o, which in some instances can result in a substantially fluid-tight seal. The seal thus formed can substantially prevent fluid communication between first pump chamber 103a and outlet channel 138o via chamber channel 131o.

In some embodiments, suction in first outlet valve chamber 101o causes first inlet valve region 151i of valve diaphragms 150a, 150b to move (e.g., flex) away from first inlet valve seat rim 135i, thereby permitting fluid communication between inlet channel 138i and first pump chamber 103a via chamber channel 131i. Suction provided via passage 163a (see FIG. 5) can simultaneously move first pump chamber region 141a of chamber diaphragms 140a, b away from the pump body 110. In some embodiments, the suction can continue to move chamber region 141a after fluid communication between inlet channel 138i and first pump chamber 103a has been established, and can draw process fluid into the first pump chamber 103a. Process fluid can proceed through inlet line 180i (see, e.g., FIG. 1), through inlet channel 138i, through valve portal 131i, into first inlet valve chamber 101i, through chamber channel 133i, and into first pump chamber 103a.

FIG. 9C shows the second inlet valve chamber 102i, second outlet valve chamber 102o and second pump chamber 103b at the end of a fluid expel stroke. The second chamber diaphragm region 141*b* of chamber diaphragms 140*a*, 140*b* is shown at an end-of-stroke position where pressure has been applied through passage 174*i* to second inlet valve chamber 101*i* and through passage 164*b* (see also FIG. 5) to second pump chamber 103*b*, and a vacuum has been supplied through passage 174*o* to second outlet valve chamber 102*o*. In such an arrangement, pressure in second inlet valve chamber 102*i* prevents fluid communication between inlet channel 138*i* and second pump chamber 103*b* via chamber channel 134*i* and valve portal 132*i* by flexing second inlet valve region 152*i* of chamber diaphragms 150*a*, 150*b* to rest on or in close proximity to second inlet valve seat rim 136*i*. Simultaneously, suction applied to second outlet valve chamber 102*o* flexes first outlet valve region 152*o* of chamber diaphragms 150*a*, 150*b* away from second outlet valve seat rim 136*o* and allows fluid communication between second pump chamber 103*b* and outlet channel 138*o* via chamber channel 134*o* and valve portal 132*o*. Simultaneously, pressure provided to chamber 103*b* continues to push against second pump chamber region 141*b* of chamber diaphragms 140*a*, 140*b* and expels process fluid through chamber channel 134*o* into second outlet valve chamber 102*0* and then through valve portal 132*o* into outlet channel 138*o*, which is in fluid communication with outlet line 180*o*.

In some embodiments, the inlet valves 101*i*, 102*i* actively control ingress of process fluid into the first and second pump chambers 103*a*, *b*, and the outlet valves 101*o*, 102*i* actively control egress of process fluid from the first and second pump chambers 103*a*, *b*, respectively. As used herein, the term "actively control" means that the valves 101*i*, 101*o*, 102*i*, 102*o* can be actuated without dependency on the direction of the flow of process fluid through the pump 100. For example, the actuation medium that controls the transitioning and positioning of the valves 101*i*, 101*o*, 102*i*, 102*o* can do so independent of the reversal of flow of process fluid through the valve.

In some embodiments a preformed diaphragm region (e.g., 141*b*, 152*i*, 152*o*) defines its natural preformed shape when in an end-of-stroke position. For example, the preformed region 152*o* shown in FIG. 9C can be in its natural state in the illustrated end-of-stroke position. When in another end-of-stroke position, the preformed region can define an inversion of the natural preformed shape. For example, in some embodiments, the preformed region 152*o* is in its natural preformed shape when in the end-of-stroke position shown in FIG. 9C, and can move to inversion of its natural preformed shape when moved to another end-of-stroke position at or near the seat rim 136*0* (such as the position of preformed region 151*o* shown in FIG. 9B). Alternatively, the preformed region 152*o* can be in its natural preformed shape when in an end-of-stroke position at or near the seat rim 136*o* and can transition to an inversion of the preformed shape at an opposite end-of-stroke position.

In some embodiments, it can be desirable for a preformed diaphragm region to be in its natural preformed shape when at an end-of-stroke position, as this can reduce strain on the diaphragm region in certain arrangements. In other embodiments, the diaphragm region can pass through its preformed shape before reaching an end-of-stroke position, which may, in some instances, cause the region to stretch in order to reach the end-of-stroke position. In still other embodiments, the diaphragm region may be prevented from achieving its natural preformed shape when operating within a pump chamber or valve chamber.

In some embodiments, it can be advantageous to switch from an expel stroke to a draw stroke before a diaphragm reaches an end-of-stroke condition, such as the position shown in FIG. 9C. Similarly, in some embodiments, it can be advantageous to switch from a draw stroke to an expel stroke before a diaphragm travels to an end-of-stroke condition such as that shown in FIG. 9B. In some embodiments, when the pump chambers are alternately and repeatedly switched between a draw stroke and an expel stroke prior to the chamber diaphragms 140*a*, 140*b* reaching an end-of-stroke position during the draw stroke, fluid flow through the inlet line 180*i* can be substantially constant. In other embodiments in which expel strokes allow the chamber diaphragms 140*a*, 140*b* to reach an end-of-stroke position, the pause in displacement of fluid during the duration of time at the end-of-stroke can cause a pulsatile output flow in the outlet line 180*o*. In some applications it can be advantageous to balance the pump 100 to control the pump chambers to switch from a draw stroke to an expel stroke prior to the chamber diaphragms reaching either end-of-stroke position.

FIG. 10 shows another embodiment of a double diaphragm pump 100' shown in cross-section with a view such as that shown in FIG. 9B. In certain embodiments, the pump 100' is configured to stall if air is drawn into the pump 100' along with the process fluid. In some embodiments, it can be advantageous in blood pumping applications to cause the pump to stall if a significant air volume is drawn into the inlet channel 138*i*. Such air intake could be due, in some rare instances, to negative suction in the inlet line that entrains air through a leak in a fitting or, in other rare instances, at the connection to a patient or by inadvertent error by the practitioners. The pump body 110' can include bypass channels 139*i*, 139*o* that allow continuous or uninterrupted fluid communication between the inlet channel 138*i* and the first pumping chamber 103*a* and between the first pumping chamber 103*a* and the outlet channel 138*o*, respectively. For example, in the illustrated embodiment, although the diaphragm 150*a* forms a seal with seat rim 135*o*, fluid communication is still possible between the first pumping chamber 103*a* and the outlet channel 138*o* because the bypass channel 139*o* provides a fluid path from the pumping chamber 103*a* to the groove 121*o*, which is in fluid communication with the outlet channel 138*o* (compare FIG. 4). The pump body 110' can include similar bypass channels that provide continuous or uninterrupted fluid communication between the inlet channel 138*i* and the second pumping chamber 103*b* and between the second pumping chamber 103*b* and the outlet channel 138*o*.

The bypass channels 139*i*, 139*o* can have flow areas that are much smaller than those defined by the valve portals 131*i*, 131*o* and chamber channels 133*i*, 133*o*. A volume of air can flow through an opening at a faster rate than a like volume of liquid. Accordingly, in the event of a significant volume of air being introduced into inlet channel 138*i* along with process fluid, the double diaphragm pump 100 will cause liquid to flow less efficiently through the pump, and air will fill the pump chambers 103*a*, 103*b* through the bypass channels 139*i*, 139*o* and then return back through the bypass channels and may prevent continually expelling air into the outlet channel 138*o* and then into the outlet line 180*o*.

For example, in some embodiments, a mixture of process fluid and air may enter the first chamber 103*a* from the inlet channel 138*i* during a fluid draw stroke. As the diaphragms 140*a*, *b* move toward the pump body 110' to decrease the volume of the chamber 103*a* during an expel stroke, air within the chamber 103*a* may preferentially exit the chamber 103*a* via the bypass channel 139*i* and return to inlet channel 138*i*. This air, and possibly additional air received via the inlet channel 138*i*, may gather or collect in the chamber 103*a* and may cycle back and forth through the bypass channels 139*i*, 139*o* over the course of repeated intake and expel strokes.

Eventually, sufficient air may gather in the chamber 103a to cause the pump 100' to operate less efficiently or to stall. For example, as an increasing volume of air passes through the bybass channel 139o to gather in a chamber 103a, the amount of blood that can be drawn into the chamber 103a and subsequently expelled from the chamber 103a can decrease due to the presence of the air.

With reference again to FIG. 9C, in certain embodiments, the pump 100 comprises a mounting hook 175. In some embodiments, the mounting hook 175 extends from the valve plate 170 in a direction substantially orthogonal to a plane defined by a base surface of the valve plate 170. The mounting hook 175 can define an opening 175a. In some embodiments, the hook 175 extends in substantially the same direction as the bosses 176a-d. The hook 175 and bosses 176a-d are further discussed below.

In some embodiments, the double diaphragm pump 100 is constructed with the inlet and outlet valve chambers 101i, 101o, 102i, 102o and the pump chambers 103a, b located on the same side of the pump body 110. The pump chambers 103a, b can also be located on opposite sides of the pump body 110 while the inlet and outlet valves 101i, 102i, 101o, 102o can be located on the opposite side of the pump body 110 from their associated pump chamber 103a, b. The pump body 110 can be constructed with more than two pump cavities 103a, b, more than two inlet valves 101i, 102i, and more than two outlet valves 112i, 112o to cooperatively work in pumping a single fluid. Also, multiple double diaphragm pumps 100 can be constructed on a single pump body 110. The diaphragms 140a, b, 150a, b can also have more valve regions 151i, 151o, 152i, 152o and pump chamber regions 141a, 141b than those shown in the depicted embodiments.

Components of the double diaphragm pump 100, or portions thereof, that are exposed to a process fluid (such as, for example, blood) can be constructed of any suitable material that is compatible with the process fluid. For example, in some embodiments, the pump 100 comprises any suitable blood-compatible material, whether currently known in the art or yet to be devised. Examples of such candidate materials can include plastic materials, such as polycarbonate (PC), polyvinyl chloride (PVC), polypropylene (PP), polyethylene (PE), polytetrafluoroethylene (PTFE), polyperfluoroalkoxyethylene (PFA), fluorinated ethylene propylene (FEP), and polyurethane (PU). In some embodiments, metal materials can be used, such as stainless steel 316L and/or titanium. In some embodiments, the body 110 is constructed of PC. The body 110 can be substantially rigid and relatively inflexible, in some arrangements.

In certain embodiments, the chamber diaphragms 140a, 140b and valve diaphragms 150a, 150b may be formed from a polymer or an elastomer. In some embodiments, polymers that have high endurance to cyclic flexing may be used, such as, for example, a fluoropolymer, such as polytetrafluoroethylene (PTFE), polyperfluoroalkoxyethylene (PFA), or fluorinated ethylene propylene (FEP). Other non-elastomer film materials may be used, such as PE, PVC, PP. In some embodiments, an elastomeric material such as silicone or polyurethane can be used for the diaphragms 140a, b, 150a, b. In certain of such embodiments, it is preferable that supporting structures be configured so as to prevent plastic hinges (e.g., relatively sharp bends in material where the diaphragm is forced by pressure into contact with features in the actuation cavities) that may cause cyclic failure.

In some embodiments, components of the pump 100 that do not contact a process fluid can be constructed of any of a variety of materials without consideration of possible incompatibilities among the materials and the process fluid. For example, in some embodiments, materials used for the chamber plate 160 and valve plate 170 can be any suitable plastic or metal material. In many embodiments, the chamber plate 160 and the valve plate 170 are substantially rigid and can be relatively inflexible.

The inlet line 180i and outlet line 180o can be made from any suitable material, and can be compatible with the process fluid. In some embodiments, the lines 180i, 180o comprise a blood compatible PVC material containing softening plasticizers, such as Tygon® S-95-E tubing available from Saint Gobain Performance Plastics, Akron, Ohio.

Figure 11:
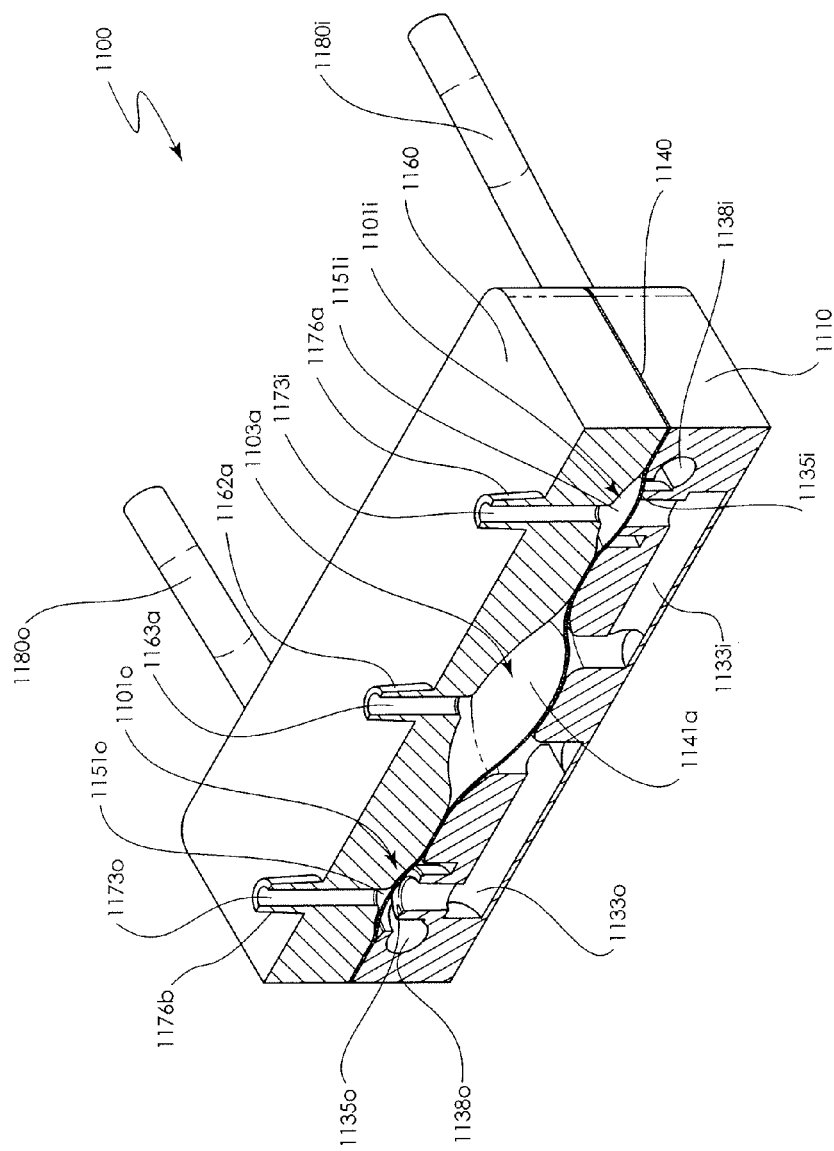
FIG. 11 is a cross-sectional perspective view of another embodiment of a diaphragm pump.

FIG. 11 illustrates an embodiment of a pump 1100. The pump 1100 can include features such as those described above with respect to the illustrated embodiments of the pumps 100 and 100'. Accordingly, features of the pump 1100 are identified with reference numerals incremented by 1000 relative to reference numerals used to identify like features of the pumps 100, 100'.

In certain embodiments, the pump 1100 can be in fluid communication with an inlet line 1180i and an outlet line 1180o. The pump 1100 can comprise a pump body 1110, which can define an inlet channel 1138i in fluid communication with the inlet line 1180i and an outlet channel 1138o in fluid communication with the outlet line 1180o. The pump 1100 can further comprise a chamber plate 1160, which can cooperate with the pump body 1110 to at least partially define a first pump chamber 1103a, a first inlet valve 1101i, and a first outlet valve 1101o. In some embodiments, one or more diaphragms 1140 are included between the pump body 1110 and the chamber plate 1160. The one or more diaphragms 1140 can include one or more diaphragm actuations regions 1141a, 1151i, 1151o configured to move within the first pump chamber 1103a, the first inlet valve 1101i, and the first outlet valve 1101o, respectively.

In some embodiments, the pump body 1110, the chamber plate 1160, and the one or more diaphragms 1140 further define a second pump chamber, a second inlet valve, and a second outlet valve (not shown) such as the illustrated first pump chamber 1103a, first inlet valve 1101i, and first outlet valve 1101o, respectively. The inlet channel 1138i can extend between the first inlet valve 1101i and the second inlet valve, and the outlet channel 1138o can extend between the first outlet valve 1101o and the second outlet valve.

In some embodiments, the first inlet valve 1101i includes a seat rim 1135i and the second inlet valve 1101o includes a seat rim 1135o. The pump body 111o can define a chamber channel 1133i that provides fluid communication between the seat rim 1135i of the first inlet valve 1101i and the first pump chamber 1103a and can define another chamber channel 1133o that provides fluid communication between the pump chamber 1103a and the seat rim 1135o of the first outlet valve 1101o. In some embodiments, the diaphragm actuation region 1151i is configured to selectively permit fluid communication between the inlet channel 1138i and the chamber channel 1133i. Similarly, the diaphragm actuation region 1151o can be configured to selectively permit fluid communication between the chamber channel 1133o and the outlet channel 1138o.

In some embodiments, the chamber plate 1160 defines a motive fluid passage 1173i in fluid communication with the first inlet valve 1101i, a motive fluid passage 1173o in fluid communication with the first outlet valve 1101o, and a motive fluid passage 1163a in fluid communication with the first pump chamber 1103a. The motive fluid passages 1173i, 1173o, and 1163a can be at least partially defined by motive fluid transfer bosses 1176a, 1176b, and 1162a, respectively. In some embodiments, the bosses 1176a, 1176b, and 1162a are configured to be connected with a motive fluid control device. In some embodiments, motive fluid is provided to the valves 1101*i*, 1101*o* and the pump chamber 1103*a* to actuate the diaphragm actuation regions 1151*i*, 1151*o*, and 1141*a*, respectively. In some embodiments, such as that illustrated in FIG. 11, motive fluid at a first pressure can be provided to both the first inlet valve 1101*i* and the first pump chamber 1103*a*, and motive fluid at a second pressure can be provided to the first outlet valve 1101*o*.

Figure 12:
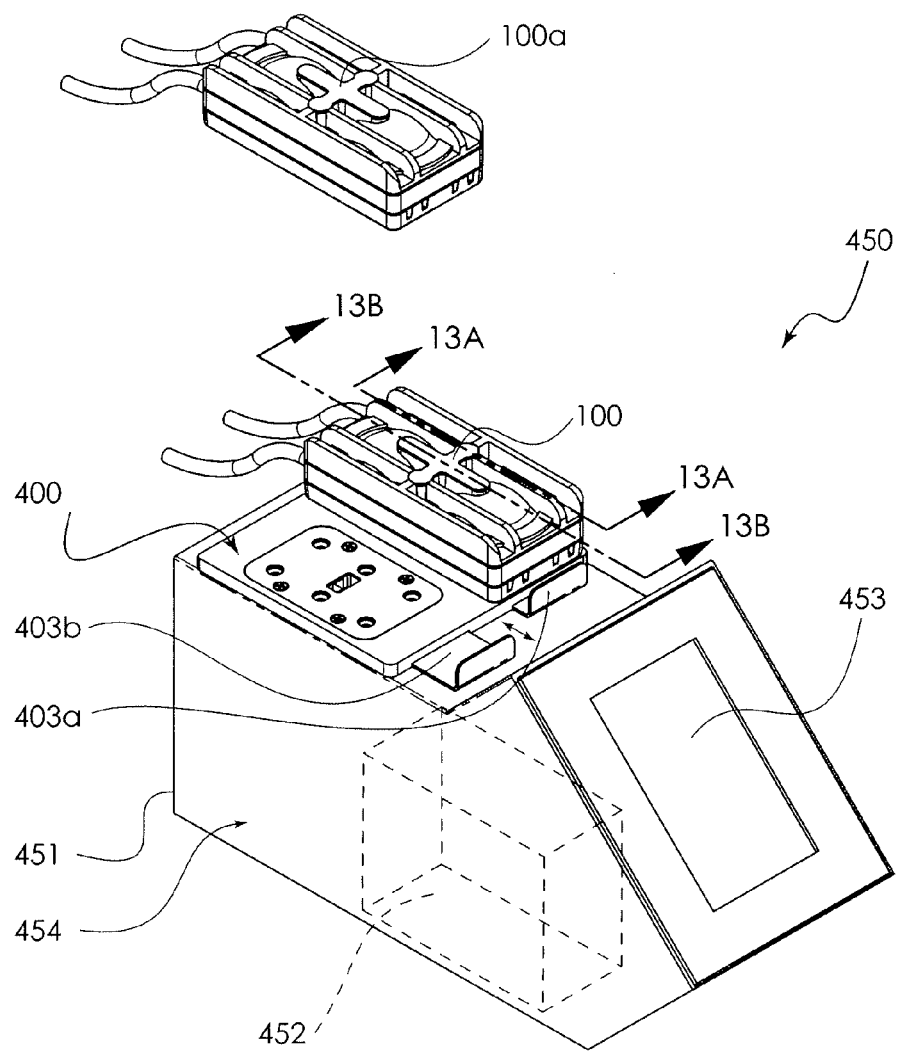
FIG. 12 is a partially exploded perspective view of two double diaphragm blood pumps configured for operative association with a reusable pump control system.
Figure 13A:
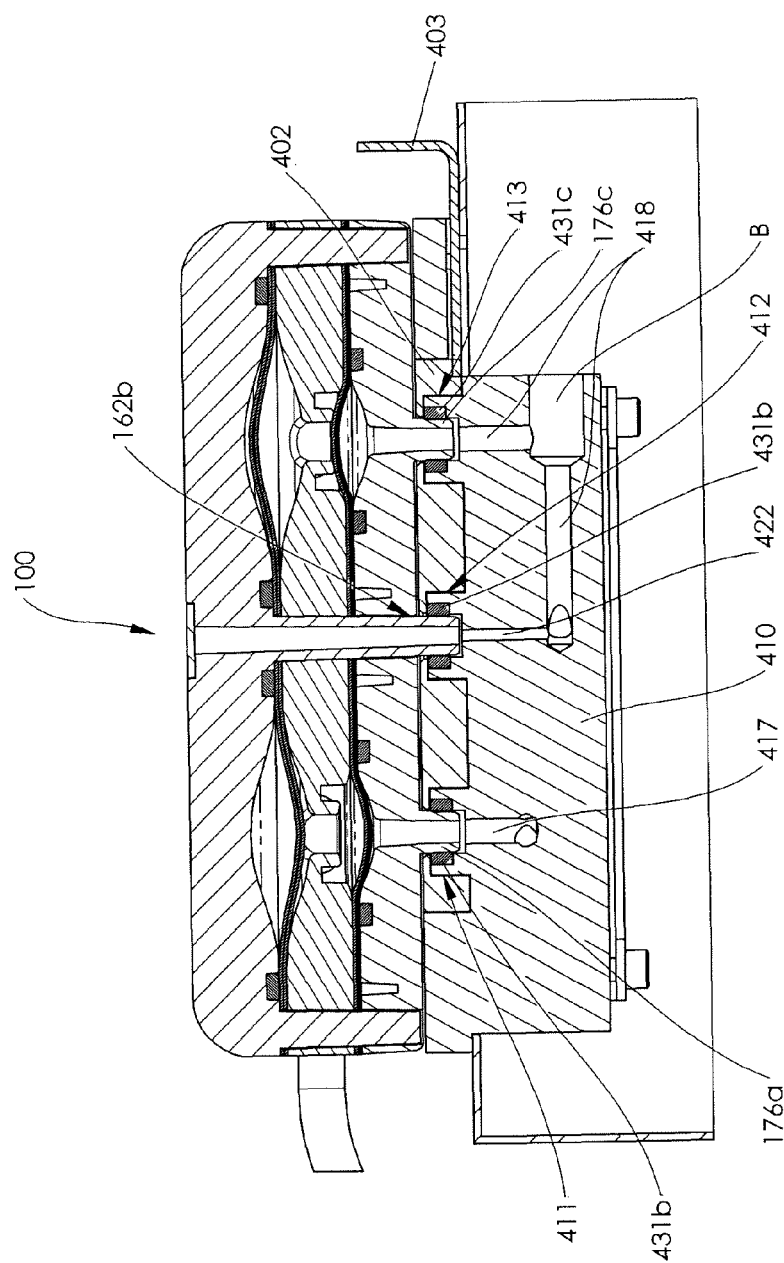
FIG. 13A is a partial cross-sectional view of a double diaphragm pump and manifold taken along cutting line 13A-13A in FIG. 12.
Figure 13B:
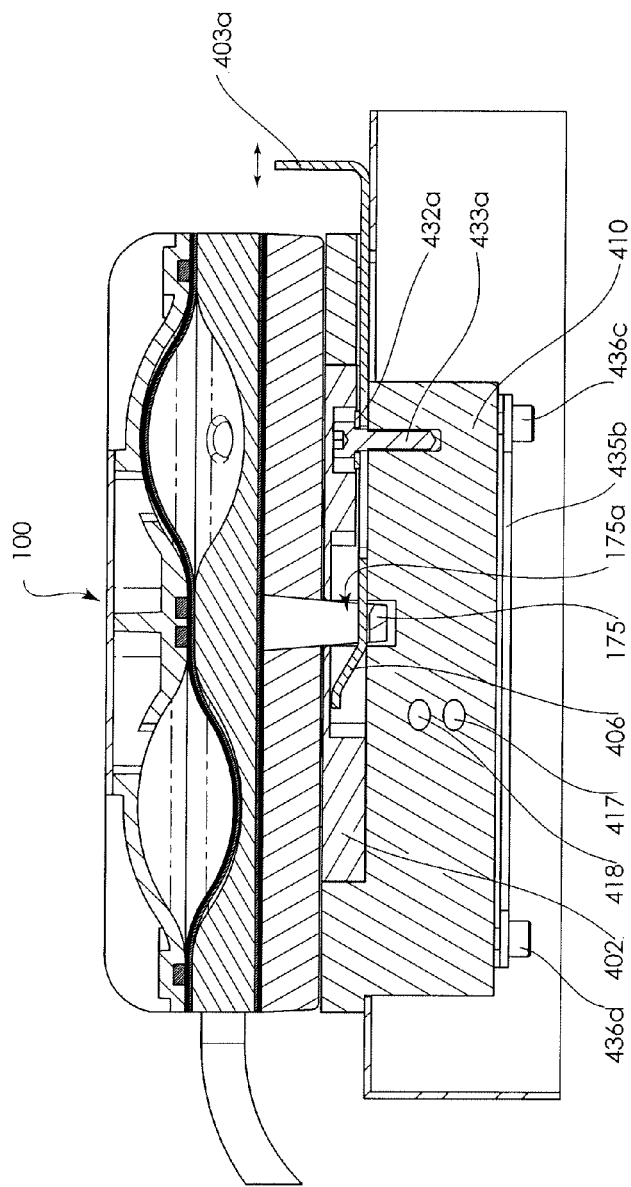
FIG. 13B is a partial cross-sectional view of a double diaphragm pump and manifold taken along cutting line 13B-13B in FIG. 12.

With reference to FIGS. 12-13B, in certain embodiments, a pump assembly 450 can include a reusable control base or pump control system 451 and one or more double diaphragm pumps 100, 100*a*. The control system 451 and one or more diaphragm pumps 100, 100*a* can be configured to selectively couple and decouple. In some embodiments, the one or more diaphragm pumps 100, 100*a* can be used with the control system 451 in a single procedure or a limited number of procedures, removed from the control system 451, and then discarded. Additional diaphragm pumps 100, 100*a* can replace the discarded diaphragm pumps 100, 100*a* in one or more additional procedures. Accordingly, in some embodiments, the control system 451 can be used in multiple procedures (whether of the same or different variety) with a plurality of disposable diaphragm pumps 100, 100*a*.

As further discussed below, in some embodiments, the control system 451 can control the manner in which the pumps 100, 100*a* operate. The control system 451 can operate a set of pumps 100, 100*a* in a variety of different modes, depending on the type of procedure involved. In some embodiments, the control system 451 is reconfigurable, such that the manner in which the control system 451 controls the pumps 100, 100*a* can be altered. The control system 451 can comprise a fluid logic system configured to direct motive fluids from different sources (e.g., motive fluids at different pressure levels) to different portions of each pump 100, 100*a*, and in further embodiments, can alternate which motive fluids sources are directed to the portions of the pumps 100, 100*a*.

In certain embodiments, the control system 451 comprises a processor 452, which can comprise any suitable logic processor or controller, and may comprise, for example, an onboard computer. In some embodiments, the processor 452 is configured to run executable computer code, and can include volatile and/or non-volatile memory. In further embodiments, the processor 452 can be configured to communicate with other devices, and may be part of a network.

In some embodiments, the control system 451 includes a user control interface 453. The interface 453 can be of any suitable variety, and can be configured to communicate information to and/or from the processor 452. For example, the interface 453 can include one or more display screens, touch screens, keyboards, mouse controllers, switches, indicators, and/or speakers. In some embodiments, instructions can be provided to the processor 452 via the interface 453. For example, in some embodiments, the processor 452 is capable of operating in a variety of different modes and the interface 453 can be used to select among the available modes. The interface 453 may also be used to program the processor 452 to operate in a new or different mode.

As further discussed below, in some embodiments, the control system 451 comprises one or more pneumatic regulators and/or vacuum generators, which can control the pressure level of a pressure source 220 and/or a vacuum source 230 (see FIG. 16); one or more motive fluid valves 210 (see FIG. 16), which can comprise one or more air valves, and/or other pneumatic control and conditioning devices; and/or other suitable control hardware. In some embodiments, the pressure source and vacuum source can be supplied to the control system by connections to external systems that are configured to supply pressurized gases or suction of gases. In some embodiments, such components and devices can be in communication with and/or controlled by the processor 452 (e.g. the setting of the pneumatic regulators that control the pressure level in a motive fluid source may be controlled by the processor).

With continued reference to FIG. 12, in certain embodiments, the control system 451 comprises an enclosure 454 and a manifold mounting assembly 400. In some embodiments, the enclosure 454 and the manifold mounting assembly 400 cooperate to form a cavity in which one or more components of the control system 451 (e.g., the processor 452, pressure source 220, and/or vacuum source 230) are contained. The manifold mounting assembly 400 can be configured to interface with one or more pumps 100, 100*a* and to selectively couple the pumps 100, 100*a* with the system 451. FIG. 12 shows an embodiment of a pump 100 in locked engagement with the manifold mounting assembly 400 and a second pump 100*a* disengaged from the manifold mounting assembly 400. The illustrated embodiment is particularly suited for use with one or two pumps 100, 100*a*. In some embodiments, the mounting assembly 400 can be used with more pumps than pumps 100, 100*a*.

Figure 14:
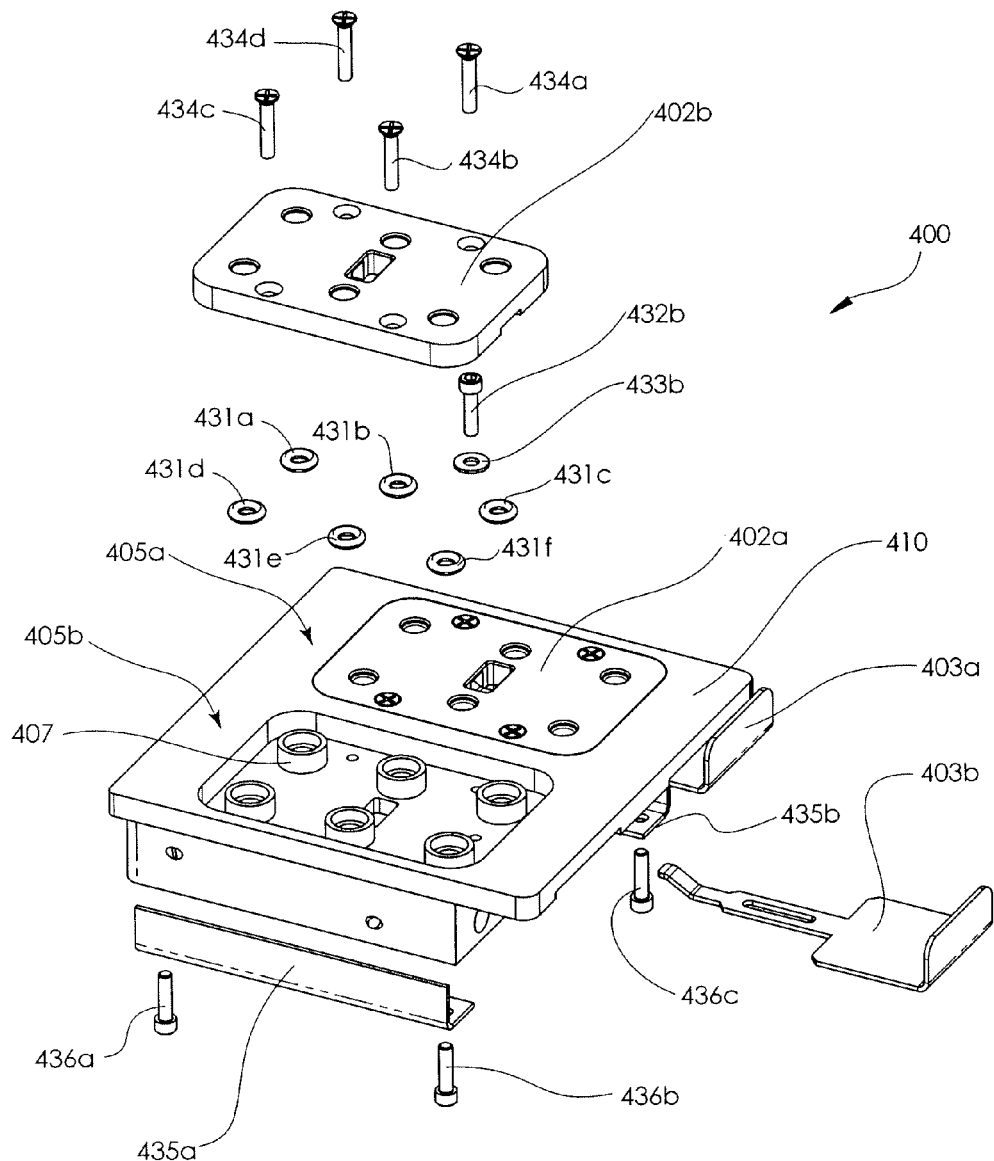
FIG. 14 is a partially exploded perspective view of an embodiment of a manifold mounting assembly.

FIG. 14 illustrates a partially exploded perspective view of an embodiment of the manifold mounting assembly 400. The illustrated embodiment includes two pump mounting areas 405*a, b*, each of which includes similar components and features. Accordingly, for convenience and not by way of limitation, the following discussion may refer to a feature of one of the pump mounting areas 405*a, b* without referring to a like feature of the other mounting area, or may refer to like features interchangeably. Other embodiments can include more than two pump mounting areas 405*a, b* and/or can include pump mounting areas that include dissimilar features.

In certain embodiments, each pump mounting area 405*a, b* of the manifold mounting assembly 400 comprises a manifold cover 402*a, b*. The manifold cover 402*b* can extend over and substantially shield a series of air transfer bosses 407 (see also FIG. 15). The cover 402*b* can define an opening associated with each air transfer boss 407 of the manifold mounting assembly 400 for receiving an air transfer boss 162*a, b* or 176*a-d* of a pump 100*a*. As further discussed below, the air transfer bosses 162*a, b*, 176*a-d* of the pump 100*a* can extend through the openings and into the air transfer bosses 407. The manifold cover 402*b* can further define an opening through which a mounting hook 175 can extend (see FIGS. 9C and 13B).

In certain embodiments, each air transfer boss 407 can receive a sealing element, such as an o-ring 431*a-e*, to facilitate or enable creation of a fluid-tight seal between the air transfer bosses 407 and the air bosses 162*a, b*, 176*a-d* of the pump 100*a*. Once the o-rings 431*a-e* are in place, the manifold cover 402*b* can be placed over the air transfer bosses 407 and secured to the manifold mounting assembly 400 via any suitable fastener, such as one or more screws 434*a-d*. In some embodiments, each o-ring 431*a-e* is retained between and is in fluid-tight contact with a ridge of an air transfer boss 407 and an underside of the manifold cover 402*b*.

In some embodiments, the manifold mounting assembly 400 comprises latches 403*a, b* that interact with the mounting hook 175 (see FIGS. 9C and 13B) of a pump 100 to selectively secure the pump 100 to the manifold mounting assembly 400. As depicted by double-headed arrows in FIGS. 12 and 13B, the latch 403*a* can move outward or inward relative to a pump 100. In some embodiments, the latch 403 is moved inward relative to the pump 100 and advanced through the mounting hook 175 to secure the pump 100 to the manifold mounting assembly 400, and is moved outward relative to the pump 100 and removed from the opening 175a defined by the hook 175 to permit removal of the pump 100 (see FIG. 13B).

In some embodiments, the latch 403a comprises a catch 406 (see FIG. 13B). The catch can provide leveraged force against the mounting hook 175 as it is slid forward to assist in energizing the radial o-ring seals 431a-f for creating sealed fluid interfaces between pump 100 and manifold mounting assembly 400.

In certain embodiments, a screw 432b and a washer 433b are used in conjunction with a manifold plate 410 to constrain the motion and positioning of latch 403b. For example, in the embodiment illustrated in FIG. 13B, the screw 432a extends through the washer 433a, through an opening in the latch 403b, and into the manifold plate 410. In other embodiments, one or more other mechanisms may be used to selectively attach a pump 100 to the manifold mounting assembly 400. For example, clips, bolts, screws, clamps, or other fasteners could be used.

With reference to FIGS. 13B and 14, in some embodiments, the manifold mounting assembly 400 includes one or more brackets 435a, b and fasteners 436a-d, which can be used to secure the manifold mounting assembly 400 to enclosure 454.

Figure 15:
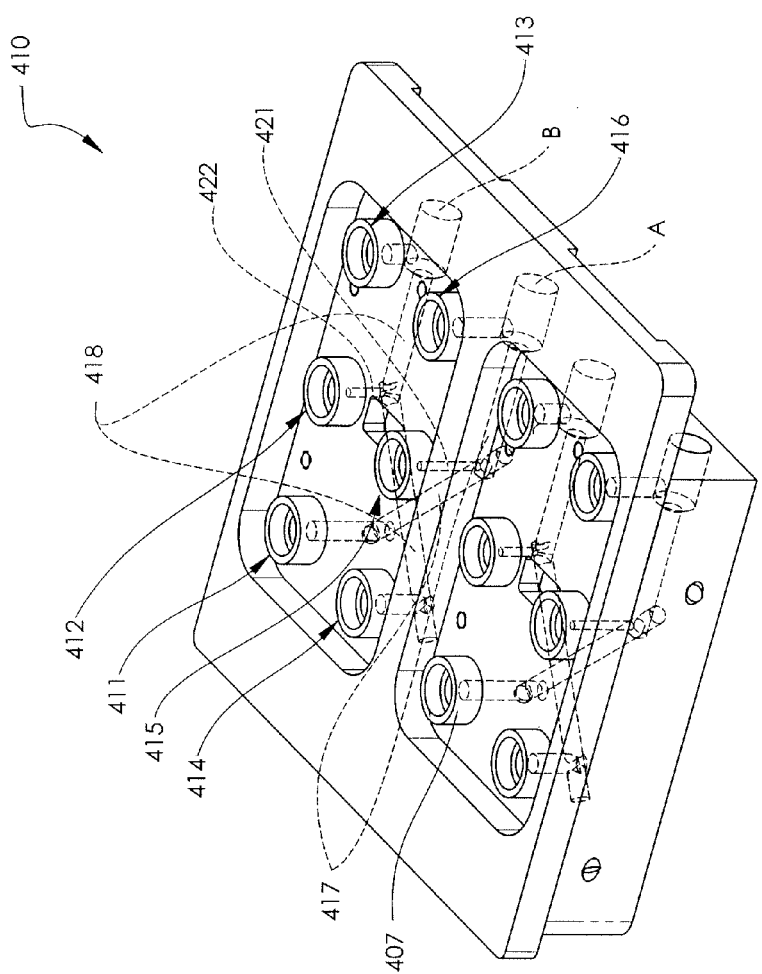
FIG. 15 is a perspective view of an embodiment of a manifold base with a portion of the interior features of the manifold base shown in phantom.

With reference to FIG. 15, in certain embodiments, the manifold mounting assembly 400 includes air passages 417, 418 (see also FIGS. 13A and 13B). In some embodiments, air passage 417 provides fluid communication between a first supply port A and air transfer bosses 411, 415, and 416 and air passage 418 provides fluid communication between a second supply port B and air transfer bosses 412, 413, and 414. As further discussed below, in some embodiments, the supply ports A, B are in fluid communication with a motive fluid control valve 210 (see FIG. 16), which can be configured to selectively permit one or more motive fluids to flow to or from the supply ports A, B.

In some embodiments, when the pump 100 is connected to the control system 451, the air transfer bosses 162a, b, 176a-d of the pump 100 are in fluid communication with the air transfer bosses 411-416 of the manifold mounting assembly 400. For example, in some embodiments, the air transfer bosses 412, 413, and 414 are connected with air transfer bosses 176c, 162b, and 176b of the double diaphragm pump 100 to provide for actuation of the second inlet valve 102i, second pump chamber 103b, and first outlet valve 101o. Similarly, the air transfer bosses 411, 415, and 416, are connected with air transfer bosses 176d, 162a, 176a of the air diaphragm pump 100 to provide for actuation of the first inlet valve 101i, first pump chamber 103a, and second outlet valve 102o.

In some embodiments, the air passages 417, 418 include restrictions 421, 422, respectively. For example, the air passages 417, 418 can include transfer passages to redirect the flow of motive fluid toward the air transfer bosses 411-416 (see FIGS. 13A and 15). In some embodiments the transfer passages associated with air transfer bosses 412 and 415 are smaller than those associated with air transfer bosses 411, 413, 414, and 416. Accordingly, in some embodiments, the restrictions 421, 422 comprise the smaller transfer passages, and can reduce the rate of change in motive fluid pressure in pump chambers 103a, b by restricting air flow through air transfer bosses 412 and 415 as compared with the rate of change in motive fluid pressure in valve chambers by not significantly restricting air flow to or from the bosses 411, 413, 414, and 416. This permits the inlet and outlet valves to open and close rapidly relative to the filling and discharging of the pump chambers. Further, in some embodiments, the volume of the valves 101i, 101o, 102i, 102o is also smaller than the volume of the pump chambers 103a, b, which can permit the valves to remain open or closed during a substantial portion of a given stroke cycle. In some embodiments, pressure sensors can be placed in fluid communication with the air transfer passages on the pump side of the restrictions 421, 422. The process fluid inlet pressure to the pump and outlet pressure from the pump can be monitored due to the motive fluid pressure at these locations and the process fluid pressure are closely related when the diaphragm regions 141a, b are not in an end-of-stroke position during the pump cycle.

In some embodiments, such as the embodiment illustrated in FIGS. 12-15, the control system 451 is capable of actuating the flow control valves 101i, 101o, 102i, 102o and the pump chambers 103a, b using a single level of pressure in one of the passages 417, 418 and a single level of suction in the other passage 417, 418 during a given stroke or portion of a stroke. Such a configuration can reduce the number of air valves, air regulators, and air control devices (such as those described below) used by the pump control system 451, which can, in some cases, reduce the manufacturing costs, reduce the complexity, decrease the potential probability of mechanical failure, and/or increase the ease of use and/or the reliability of the pump assembly 450.

FIG. 16 depicts a schematic illustration of another embodiment of the pump assembly 450, and includes like reference numerals to identify like features disclosed in other figures of the present disclosure. The pump assembly 450 can comprise a motive fluid logic system 460 configured to control a double diaphragm pump 100. In some embodiments, the motive fluid logic system 460 comprises the control system 451 (see FIG. 12). The logic system 460 can comprise a processor 452 such as described above. In some embodiments, the processor 452 is in communication (e.g., electrical, wireless, or other communication) with a valve controller 212 and can control the operation thereof. As discussed above, in some embodiments, the processor 452 is pre-programmed with one or more operational modes by which it controls the controller 212, and in further embodiments, the processor 452 can be reconfigurable.

In some embodiments, the valve controller 212 is configured to effect transition of a motive fluid valve 210 among a variety of operational states. In some embodiments, the valve controller 212 comprises an electrical actuator (or controller) or a pneumatic actuator (or controller), which can transition the valve 210 among the operational states.

In some embodiments, the valve 210 is configured to operate in two or more positions and may include a resting state, a first state, and a second state. In the illustrated embodiment, the resting, disconnected, closed, or shutoff state of the valve 210 corresponds with the middle rectangular section, the first operational state corresponds with the top rectangular section, and the second operational state corresponds with the bottom rectangular section. In some embodiments, the resting state of the valve 210 substantially prevents fluid communication between the pump 100 and the pressure source 220 and vacuum source 230. The valve 210 can be positioned in this state, for example, during installation and removal of the pump 100 or during a pump "off" condition or pump "shut down" condition.

In some embodiments, the valve 210 provides fluid communication between a pressure source 220 and the supply port A and between a vacuum source 230 and the supply port B when in the first state, and provides fluid communication between the pressure source 220 and the supply port B and between the vacuum source 230 and the supply port A when in the second state. As indicated by the double-headed arrow, in some embodiments, the valve 210 passes through the resting state when transitioning between the first and the second operational states. Other arrangements of the valve 210 are also possible. For example, the first and second operational states of the valve 210 can be positioned adjacent to each other such that the valve 210 does not pass through the resting state in transitioning between the first and second operational states. In other embodiments, multiple motive fluid valves 210 can be used.

The pressure source 220 can comprise any suitable source of motive fluid such as, for example, an air compressor, a pressurized canister, connection to a pressurized air line, etc. Similarly, the vacuum source 230 can comprise any suitable source of motive fluid (or, in some instances, a relative lack thereof), such as, for example, a connection to a rarefied air line or a vacuum generator or an air compressor configured to evacuate or partially evacuate a chamber. In some embodiments, the vacuum source 230 comprises a vent to atmosphere, and the pressure source 220 is pressurized to a level that exceeds that of atmospheric pressure. In some embodiments, the pressure source 220 and/or the vacuum source 230 can comprise one or more pneumatic regulators to help achieve a relatively constant pressure level. As an example, in some embodiments, the pressure source 220 can comprise a first motive fluid, such as compressed air at a first pressure level (e.g., about 300 mmHg (millimeters of mercury)), and the vacuum source 230 can comprise a second motive fluid, such as rarefied air at a second pressure level (e.g., about −200 mmHg vacuum pressure).

In certain embodiments, the pump 100 is in fluid communication with a process fluid source 238, which can comprise any fluid for which pumping is desired. For example, in some medical applications, the process fluid source 238 comprises blood circulating in the vasculature of a patient. Other fluids at a variety of pressures and/or at a variety of viscosity levels are also possible. The pump 100 can be in fluid communication with the process fluid source 238 via the inlet line 180i. The pump 100 can further be in fluid communication with a process fluid destination, discharge, receiver, or return 239 via the outlet line 180o. In some embodiments, the process fluid source 238 and the process fluid return 239 are at about the same pressure. In other embodiments, the process fluid source 238 is at a lower pressure than the process fluid return 239. Other arrangements and configurations are also possible.

FIG. 16 illustrates that the motive fluid of pressure source 220 and the vacuum source 230, respectively, are in selective fluid communication with pump 100 via the manifold mounting assembly 400. In certain embodiments, the vacuum source 220 (which may be a vent) can be at a pressure that is less than the process fluid source 238 pressure to allow intake of the process fluid into the pumping chambers, and the pressure source 230 can be at a pressure level that is greater than that of the process fluid return 239. The pressure levels or suction levels can be selectively controlled by pressure regulators (not shown in FIG. 16) or other devices to the desired levels for pumping the process fluid. In various embodiments, the pressure level of motive fluid provided by the pressure source 220 can be between about 0 mmHg and about 1000 mmHg, between about 50 mmHg and about 500 mmHg, or between about 100 mmHg and about 200 mmHg. In various embodiments, the pressure level of motive fluid provided by the vacuum source 230 can be between about −500 mmHg and about 0 mmHg, between about −250 mmHg, or between about −100 mmHg and about −50 mmHg.

In some embodiments, the control valve 210 is alternated between operational states to cyclically apply pressure and vacuum to supply ports A and B prior to the chamber diaphragms 140a, b reaching the end-of-stroke or pump chamber surfaces 114a, 114b and/or the chamber cavity surfaces 165a, b. In certain of such embodiments, the pressure and flow of the process liquid at the process fluid receiver 230 can be maintained at a substantially constant level.

In certain embodiments, as the pump 100 causes fluid to flow from the process fluid source 238 to the process fluid return 239, the flow can be restricted by the capacities of fluid carrying components that may be located between the process fluid source 238 and the inlet line 180i and/or between the outlet line 180o and the process fluid receiver 239. In some embodiments, the pressure levels of the pressure source 220 and/or the vacuum source 230 and/or the operational speed or cycling rate of the valve 210 can be adjusted to achieve a desired flow rate of the process fluid.

In certain embodiments, the pressure levels of the sources 220, 230 and/or the cycling rate (or rates) of the valve 210 can be selectively changed to cause the double diaphragm pump 100 to operate in one or more different desired operating modes. For example, in a first illustrative mode, the valve 210 can switch the first supply port A from being in fluid communication with the pressure source 220 to being in fluid communication with the vacuum source 230 and can substantially simultaneously switch the second supply port B from being in fluid communication with the vacuum source 230 to being in fluid communication with the pressure source 220. The change in supply sources 220, 230 can cause the chamber diaphragms 140a, b to switch stroke direction prior to one of the pump chambers 103a, b being completely filled and prior to the other pump chamber 103a, b being completely emptied. With the pump chambers 103a, b operating opposite from each other (e.g., one chamber 103a draws process fluid from the fluid source 238 while the other chamber 103b expels process fluid to the fluid return 239), the pump 100 can draw process fluid and expel process fluid at a substantially constant rate.

In another mode, the pump 100 can be controlled to provide a substantially constant draw pattern or fill rate and a pulsatile discharge pattern by adjusting the cyclic speed of the control valve 210, the vacuum level of the vacuum source 230, and/or the pressure level of the pressure source 220. For example, in some embodiments, one of the chamber diaphragm regions 141a, b can switch stroke direction prior to completely filling one of the chambers 103a, b with process fluid when the valve 210 transitions from an open state to a closed state, and can completely discharge the contents of the chamber 103a, b and contact one of the chamber cavity surfaces 114a, b for a period of time before the valve 210 transitions from the closed state back to the open state. Likewise, the other chamber diaphragm region 141a, b can reach the end-of-stroke condition when it completely discharges the contents of the other chamber 103a, b and can be in contact with the other chamber cavity surface 114a, b for a period of time prior to the valve 210 transitioning from a closed state to an open state, and can fail to reach the fill end-of-stroke condition of the chamber 103a, b with process fluid prior to the valve 210 transitioning from the open state back to the closed state.

Similarly, in yet another mode, the pump can operate in a pulsatile fill pattern and substantially constant discharge pattern. In certain of such embodiments, one of the chamber diaphragm regions 141a, b can permit one of the chambers 103a, b to completely fill with process fluid and can contact one of the cavity surfaces 165a, b for a period of time before the valve 210 transitions from a substantially full state to a partially emptied state, and can fail to completely discharge the contents of the chamber 103a, b before the valve 210 transitions from the partially emptied state back to the substantially full state. Likewise, the other chamber diaphragm region 141a, b can fail to completely discharge the contents of the other chamber 103a, b before the valve 210 transitions from a partially emptied state to a substantially full state, and can permit the other chamber 103a, b to completely fill with process fluid and can contact the other cavity surface 165a, b for a period of time before the valve 210 transitions from the substantially full state back to the partially emptied state.

Other embodiments of supplying motive fluid to the double diaphragm pump 100 are also possible. For example, in some embodiments, multiple air control valves 210 may be employed. In further embodiments, a common motive fluid supply to one or more of the valves 101i, 101o, 102i, 102o and/or a common motive fluid supply provided to the pump chambers 103a, 103b can instead be replaced with a separate supply of motive fluid to each valve 101, 102 and chamber 103. For example, certain embodiments of the two air transfer passages 417, 418 could be replaced with six separate passages (one for each air transfer boss 411-416).

In some embodiments, the valves 101i, 101o, 102i, 102o and chambers 103a, b can be sequenced electronically to provide operating modes such as those described above. In further embodiments, operating a pump in a flow forward mode and then in a flow reverse mode by changing the sequencing of actuating the valves 101i, 101o, 102i, 102o and chambers 103a, b can also be achieved. In some embodiments, individual control of the pump valves 101i, 101o, 102i, 102o and pump chambers 103a, b can also allow other pump operating modes that can create constant (or substantially constant) and pulsatile flow from the process fluid source 238 to the process fluid receiver 239 (or vice versa). In some embodiments, time delays between allowing fluid communication between motive fluid sources (e.g., sources 220, 230) and one or more of the chambers 103a, b and valves 101i, 101o, 102i, 102o using individual controls can be advantageous. For example, in some embodiments, it can be desirable to actuate one or more of the valves 101i, 101o, 102i, 102o prior to actuating the chambers 103a, b FIG. 17 is a schematic illustration of an embodiment of a cardiopulmonary by-pass system 700 that includes multiple double diaphragm blood pumps 100b-f. The system 700 can further include one or more reservoirs 706, blood oxygenators 701, fluid conduits, such as tubing segments 702, 705, catheters 704, 712, cannulae 703, 709, medical fluid sources 711, heat exchangers, and/or filtration units. Certain embodiments of the system 700 include components and sub-systems that are not shown in FIG. 17 for purposes of clarity. However, it will be understood that such components and sub-systems are conventional and readily available from numerous well-known sources. In some embodiments, the system 700 uses cannulae that are either inserted directly into the right atrium of the heart (as illustrated in FIG. 17), to the vena cava, or at another desired location of the patient P. Interconnections between devices or components of the system 700 can include, in some embodiments, segments of surgical tubing. For example, in some embodiments, conventional ⅜ or ¼ inch inner diameter surgical polyvinylchloride tubing is used.

In certain embodiments, one or more of the diaphragm blood pumps 100b-f may have separately selectable and controllable pressure levels. For example, in some embodiments, each blood pump 100b-f is connected to a separate pressure source 220 and/or a separate vacuum source 230. In further embodiments, one or more of the pumps 100b-f can include a valve 210 that cycles at a different rate. In some embodiments, one or more of the pumps 100b-f share a common pressure source 220 and/or vacuum source 230. In certain of such embodiments, pneumatic regulators can be placed in line from the main pressure source 220 and vacuum source 230 to create unique pressure and/or suction levels for each pump 100b-f.

In some embodiments, one or more of the diaphragm blood pumps 100b-f may have separate motive fluid control valves 210, and one or more controllers 212 associated with each control valve 210 may operate the pumps 100b-f at different rates, which may be dependant upon the function the pump serves within the cardiopulmonary by-pass system 700. In some embodiments, a single processor 452 controls the one or more valve controllers 212 and the cycle rates or cycle patterns of the one or more valves 210. In other embodiments, multiple processors may provide the pumps 100b-f with different pumping rates and/or modes.

In certain embodiments, the reservoir 706 is supplied with blood flow from the patient P from the venous return catheter 704 via the venous tubing segment 705 and from the interconnections with the diaphragm blood pumps 100c 100d, and may be interconnected with other components of the system 700. Blood can be pumped from the reservoir 706 using a double diaphragm blood pump 100b, through the blood oxygenator 701, and back to the patient P via arterial tubing segment 702 and arterial cannula 703.

In some embodiments, the double diaphragm pump 100b may be operated in a manner that provides pulsatile blood flow to the patient P through the arterial cannula 703. A time delay between the cyclically controlled discharge of the pump chambers 103a, b, such as described above, can cause the pump 100b to create a more physiological "heart-like" flow through the circuit. Many of the components in the system 700 can act to dampen the effect of pulsation created by the pump 100b before the blood is returned to the patient P. In some embodiments, the pump 100b can be controlled to offset these effects. For example, in some embodiments, a processor 452 includes programmed instructions and/or implements one or more algorithms to counteract pulsation dampening provided by the system 700. In some embodiments, the processor 452 can utilize information regarding the amount of dampening provided by the system to dynamically alter operation of the pump 100b and thereby provide a desired pulsatile pumping pattern. For example, in some embodiments, the system 700 includes one or more flow meters or pressure sensors (not shown) that provide information to the processor 452 regarding the pressure and/or the flow rate of blood within the tubing segment 702.

In certain embodiments, the pump 100b operates in a mode that creates a substantially constant flow into the venous return catheter 704 from the patient P and a pulsatile outlet flow out of the arterial cannula 703 and to the patient P. Dampening of the pump-created pulsations in the various reservoirs, tubing segments, and other devices in the circuit may occur. The dampening effects can be offset by controlling the vacuum source 220, pressure source 230, and pump cycle rate to cause the pump 100b to expel fluid at a faster rate than blood is drawn, which can create an end-of-stroke discharge condition during each pump stroke. In other embodiments, the pump 100b can exhibit substantially equivalent discharge and fill times, which can create a substantially constant flow into the venous return catheter 704 from the patient and a substantially constant flow out of the arterial cannula 703 and into the patient P. Pump-created process fluid pressure pulsations can be dampened by the various reservoirs, tubing segments, and other devices in the circuit causing a substantially uniform flow into and out of the extracorporeal circuit.

In certain embodiments, when the diaphragm blood pump 100b is used to effect blood flow both away from patient P, such as via the venous return catheter 704 and into the patient, such as via arterial cannula 703, flow rates through the pump can be in a range of, for example, between about 1.0 and about 7.0 liters per minute, between about 1.0 and about 5.0 liters per minute, between about 1.0 and about 3.0 liters per minute, no more than about 7.0 liters per minute, no more than about 6.0 liters per minute, no more than about 5.0 liters per minute, no more than about 4.0 liters per minute, no more than about 3.0 liters per minute, no less than about 1.0 liters per minute, no less than about 2.0 liters per minute, or no less than about 3.0 liters per minute, depending on the medical procedure involved.

With continued reference to FIG. 17, blood may be removed and recovered from a surgical field via one or more suction devices 713 that can be positioned or manipulated in the surgical field and interconnected to a diaphragm blood pump 100c. Examples of such a suction device that can be suitable for operation with the pump 100c are available, for example, from Medtronic DLP, Inc. of Grand Rapids, Mich.

Blood can also be recovered through the vent catheter 712, which may be placed inside a cavity of the heart or other cavity of a patient to withdraw blood and control the pressure or suction level inside the cavity. In such applications, it can be desirable to operate the pump 100d with near uniform suction by cyclically switching the filling and discharge of the pump chambers 103a, b before the diaphragms reach an end-of-stroke fill position. The recovered blood may be sequestered in a separate reservoir (not shown) and may be selectively returned to the reservoir 706. The recovered blood may also be processed through a system (not shown) configured to clean the blood before it is returned to the reservoir 706. In some embodiments, flow rates through the diaphragm blood pumps 100c, 100d used to effect blood flow from patient P via the suction device 713 and the vent catheter 712 to the reservoir 706 can be in the range of between about 0 and about 1.0 liters/minute, depending on the medical procedure being performed.

As shown in FIG. 17, in some embodiments, a medical fluid source 711 is coupled with a pump 100f. In some embodiments, the medical fluid source 711 comprises cardioplegia fluid, which can be mixed with blood and supplied to the patient P by operation of the diaphragm blood pumps 100e, f. In some embodiments, controlling the cardioplegia fluid mixture and delivery rate (e.g., before returning the mixture to the patient P) can be accomplished by controlling the discharge pressure of one or more of the pumps 100e, f. For example, in some embodiments the pressure level of one or more pressure sources 220 and/or vacuum sources 230 associated with one or more of the pumps 100e, f can be adjusted. In some embodiments, the process fluid discharged from one or more of the pumps 100e, f can be passed through one or more flow restrictors (not shown). In certain embodiments, the rate of flow can be nearly constant at a given pressure difference across the restrictors, even with small changes in fluid conditions, such as temperature and/or viscosity fluctuations.

In some embodiments, one or more flowmeters (not shown) can be included in the outlet fluid lines of one or more of the pumps 100e, f and can sense the flow rate of fluid discharged from the pumps 100e, f. The one or more flowmeters can provide feedback information regarding the flow rate to one or more processors 452 that control the pumps 100e, f.

In some embodiments, the pressure level in the pressure source 220 and/or the vacuum source 230 can be adjusted in response to the feedback information to cause the flow rate from the pumps 100e, f to increase or decrease to obtain a desired level of mixing and a desired delivery rate of mixed fluid to the patient P. In some embodiments, the cycle rate at which diaphragm actuation regions of a given pump 100e, f are actuated can be adjusted to provide increased or decreased fluid flow from that pump 100e, f. In certain embodiments, appropriately mixed and/or heated or cooled cardioplegia fluid can be delivered via a tubing segment and cardioplegia cannula 709 to the patient P.

In certain embodiments, the pumps 100b-f can provide desirable pressure levels for the system 700. In some embodiments, the pumps 100b-f may be safer than pumps conventionally used in some of the applications described above, such as roller pumps. For example, if a vascular access connection to the patient P is somehow degraded or a blockage occurs in the system 700 (e.g., via a kink in a portion of tubing), certain embodiments of the pumps 100b-f have limited capability to generate high pressure and/or high suction levels that may damage the blood in the system 700 and/or that might otherwise be hazardous to the patient P. For example, in some embodiments, the pressure sources 220, 230 can be at pressure levels that limit the amount of pressure and/or suction provided to extracorporeal blood within the system 700. In various embodiments, the pressure of extracorporeal blood within the system is within a of between about −250 mmHg and about 500 mmHg, between about −200 mmHg and about 400 mmHg, or between about −100 mmHg and about 300 mmHg. In some embodiments the pressure of extracorporeal blood within the system 700 is no less than about −250 mmHg, no less than about −200 mmHg, no less than about −150 mmHg, no less than about −100 mmHg, no greater than about 500 mmHg, no greater than about 400 mmHg, no greater than about 300 mmHg, or no greater than about 200 mmHg.

Further, some embodiments of the pumps 100b-f do not significantly raise the temperature of blood within the system 700 if a vascular access connection to the patient P is somehow degraded or a blockage occurs in the system 700. In various embodiments, the pumps 100b-f change (e.g., raise) the temperature of extracorporeal blood within the system 700 by no more than about 3° C., no more than about 4° C., no more than about 5° C., or no more than about 6° C.

FIG. 18 is a schematic illustration showing an embodiment of a heart-assist system 750 that comprises a double diaphragm pump 100g. The pump 100g can be attached to an inlet line 180i and an outlet line 180o. In the illustrated embodiment, the inlet line 180i provides fluid communication between the vasculature of the patient P and the pump 100g. In some embodiments, the inlet line 180i is attached to a lower pressure blood vessel, such as a vein or ventricle, via a cannula or an anastomosis attachment 753. Similarly, the outlet line 180o can be attached to a higher pressure blood vessel, such as an artery or aorta, via a cannula or anastomosis attachment 754. In some embodiments, each of the inlet lines 180i and outlet lines 180o comprises a tubing segment. The tubing sections may be percutaneous and can allow the pump 100g to run externally to the patient P.

In some embodiments, the heart-assist system 750 comprises additional components and devices that are known in the art (not shown). For example, in various embodiments, the heart-assist system 750 comprises one or more reservoirs, air bubble traps, filters, and/or other devices.

In various embodiments, the system 750 can provide flow rates to or from the patient P in the range of about 1.0 liters/ minute to about 8.0 liters/minute, depending on the amount of heart support needed. In certain embodiments, the pump 100g comprises pump chambers 103a, 103b that each have a volume of between about 15 cubic centimeters and about 50 cubic centimeters, between about 20 cubic centimeters and about 30 cubic centimeters, no more than about 25 cubic centimeters, or about 25 cubic centimeters. In some embodiments, the pump 100g is operated at a rate between about 10 and about 200 cycles per minute, between about 90 and about 130 cycles per minute, between about 100 and about 120 cycles per minute, no more than about 200 cycles per minute, no more than about 150 cycles per minute, no more than about 120 cycles per minute, no less than about 10 cycles per minute, no less than about 50 cycles per minute, no less than about 100 cycles per minute, or about 120 cycles per minute. In various embodiments, the pump 100g can deliver blood to the patient P at a rate between about 2 liters per minute and about 8 liters per minute, between about 3 liters per minute and about 7 liters per minute, or between about 4 liters per minute and about 6 liters per minute. In certain embodiments, the volume of the pump chambers 103a, 103b of a pump 100g and the number of cycles per minute at which the pump 100g operates can be adjusted to provide a desired flow rate. In further embodiments, relatively lower cycles per minute can lengthen the life expectancy of the pump 100g and/or can aid in providing pulsatile blood flow to a patient that mimics a heartbeat.

FIG. 19 schematically illustrates a hemodialysis system that includes an extracorporeal circuit 800. In certain embodiments, the circuit 800 includes a diaphragm pump 100h, a dialyzer 810, and a dialyzing liquid system 820. The circuit 800 can be in fluid communication with a patient P. Blood can be withdrawn from the patient P at a blood source 238 and can be returned to the patient P at a blood receiver 239. Blood can flow through the circuit 800 in the direction of the arrows. In the illustrated embodiment, blood flows from the patient P to a drip chamber 803 via tubing 802, from the drip chamber 803 to the pump 100h via tubing 805, and from the pump 100h to the dialyzer 810 via tubing 807. Blood flows from the dialyzer 810 to a drip chamber 812 via tubing 811, and from the drip chamber 811 to the patient P via tubing 814.

In some embodiments, uptake from the process fluid source 238 and discharge to the process fluid receiver 239 occurs via needles punctured into an artery to vein fistula or graft shunt, or alternatively, from a catheter positioned in a large central vein. In certain embodiments, for the portion of the circuit 800 between the patient P and the pump 100h, blood pressure can be measured and monitored by means of a pressure sensor, such as a piezo-resistive pressure transducer 804a that can be connected to the drip chamber 803, whereby a hydrophobic membrane filter (not shown) serves to prevent contamination of the blood. Similarly, venous reflux pressure in the portion of the circuit 800 between dialyzer 810 and the patient P can be measured by means of a pressure transducer 804b. Pressure sensors can be used at other portions of the circuit 800. For example, in some embodiments, pressure sensors can be used to monitor the pressure levels of blood entering and exiting the pump 100h. Pressure sensors can also be used to determine the pressure levels of motive fluid provided to the pump 100h.

In certain embodiments, the blood pump 100h effects the flow of blood in the extracorporeal circuit 800. In some embodiments, a heparin pump 808 provides for continuous feed of a desired heparin dose to prevent blood coagulation. The dialyzing liquid system 820 causes dialyzing liquid to flow through the dialyzer 810 and acts as a receiver of excess fluid and toxins removed from the blood that flows through the dialyzer. In some embodiments, the components of the extracorporeal blood circuit 800 are connected with each other via suitable safety devices known in the art or yet to be devised.

In some embodiments, an air detector 825 is included between the dialyzer 810 and the patient P. The air detector 825 can be configured to prevent infusion of blood foam or air, which may have entered the extracorporeal circuit 800, into the patient P. In some embodiments, the air detector 825 recognizes whether air bubbles or microfoam are present in the drip chamber 812 or elsewhere in the circuit 800. The air detector 825 can be in communication with a processor 452 (see, e.g., FIG. 16), which may switch off the blood pump 100f in response to information received from the detector 825.

In other embodiments, the pump 100h may similarly be deactivated in response to other information regarding the circuit 800. For example, the sensors 804a, b may detect an undesirable increase or decrease of the arterial or venous pressure above or below a threshold level. The information can be used to deactivate the pump 100h. Similarly, the pump 100h may be deactivated as a result of a blood leak. In some embodiments, the pump 100h may be operatively associated with a control system 451, which may include an interface 453. In some embodiments, the interface 453 can display or otherwise signal information received from sensors within the circuit 800.

In some embodiments, information regarding the pressure of blood in the circuit 800, such as information provided by one or more of the pressure transducers 804a, b, is used to adjust the pressure level of motive fluid delivered to the pump 100h. For example, in some embodiments, the pressure transducers 804a, b, are configured to communicate with a processor 452 (see, e.g., FIG. 12), such as by one or more electrical or wireless connections. The processor 452 can utilize the information thus received to selectively control the pressure levels of motive fluid delivered from motive fluid sources, such as the sources 220, 230, in a manner such as described above (e.g., via one or more pressure regulators) and/or to control cycle rates and stroke durations of the pump 100h. For example, in some embodiments, the pressure levels of the motive fluid from the pressure sources 220, 230 and the cycle rates at which fluid communication is alternately established between distinct sets of valves and pump chambers is adjusted such that substantially constant fluid flow is established from the patient P to the extracorporeal circuit 800 and/or from the extracorporeal circuit 800 to the patient P. In some embodiments, the pump 100h provides pulsatile flow to the dialyzer 810 and essentially constant flow from the patient P to the extracorporeal circuit 800.

In certain embodiments, the pump 100h can provide desirable pressure levels for the extracorporeal circuit 800. In some embodiments, the pump 100h may be safer than conventional dialysis pumps, such as roller pumps. For example, if the vascular access connection to the patient is somehow degraded or a blockage occurs in the extracorporeal circuit 800 (e.g., via a kink in a portion of tubing), certain embodiments of the pump 100h have limited capability to generate high pressure and/or high suction levels that may damage the blood in the circuit 800 and/or that might otherwise be hazardous to the patient P. Further, some embodiments of the pump 100h does not significantly raise the temperature of blood within the circuit under such conditions of connection degradation or blockage.

In some embodiments, the diaphragm blood pump 100f generates two overlapping substantially square wave inflow pressure profiles and outflow pressure profiles during the pumping cycle which can result in a substantially constant blood inflow pressure and/or a substantially constant blood outflow pressure. The inflow and outflow pressures can be set near or within safety limits to provide maximum process fluid flow without triggering pressure limit alarms. The pressure profile generated by conventional roller pumps used in hemodialysis procedures is somewhat sinusoidal and may only operate at the maximum pressure level for a short duration of the pumping cycle. Accordingly, in some embodiments, as compared with such conventional pumps, the pump 100*h* can achieve higher blood flows at the same peak pressure limits. Higher flow rates can reduce the duration of a given hemodialysis procedure. In some embodiments, the inflow rate and/or the outflow rate of the pump 100*h* can be controlled or balanced (e.g., via the processor 452) to be substantially continuous with little pulsation of pressures or flow, as compared to some roller pumps that cannot simultaneously control the inflow pressure, outflow pressure, and flowrate. In other embodiments, the pump 100*h* can be configured to operate in a manner similar to conventional roller pumps, if desired.

Non-limiting examples will now be discussed with reference to FIGS. 20, 21, 22A, and 22B. These examples provide illustrations of performance capabilities of some embodiments, and are not intended to limit the foregoing disclosure in any respect.

EXAMPLE 1

Figure 20:
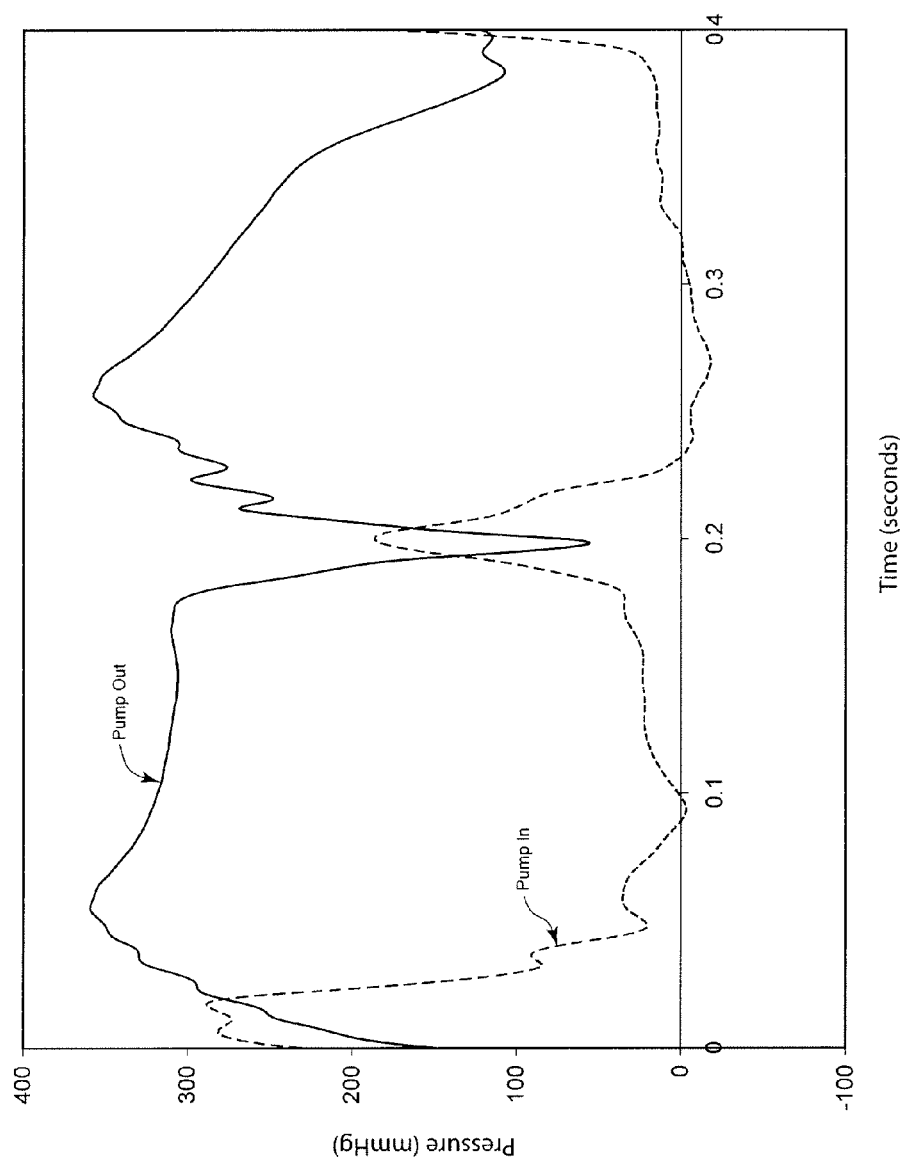
FIG. 20 is a chart showing an example of the pressure over time of blood entering and also of blood exiting an embodiment of a double diaphragm pump of the system depicted in FIG. 17 when configured for relatively constant flow operation.

FIG. 20 is a chart showing an example of pressure over time during a single pump cycle of an embodiment of a pump 100*b* used in a simulation of a cardiopulmonary bypass system such as the system 700 of FIG. 17. The chart depicts the pressure over time of blood entering the pump 100*b* (illustrated by the curve "Pump In") and also depicts the pressure over time of blood exiting the pump 100*b* (illustrated by the curve "Pump Out"). In the illustrated example, the pump 100*b* was operated in a mode for approximately uniform flow entering an extracorporeal circuit and approximately uniform flow exiting the circuit.

Various operational parameters of the pump 100*b* of the present example or of other embodiments of the pump 100*b* can be altered such that the inflow pressure for the extracorporeal circuit and the outflow pressure for the extracorporeal circuit are more uniform than that shown. For example, in some embodiments, the valley of the "Pump Out" line at the time coordinate of 0.2 seconds is relatively more shallow (e.g., has a minimum value of between about 200 and about 300 mmHg) and/or may be relatively more constricted (i.e., span over a shorter time period). Similarly, in some embodiments, the peak of the "Pump In" line at the time coordinate of 0.2 seconds is smaller (e.g., has a maximum valve of between about 0 and about 100 mmHg) and/or may be relatively more constricted.

In some embodiments, the inflow to the pump 100*b* and outflow from the pump 100*b* are approximately uniform. As used herein, the term "approximately uniform" when used to describe a flow rate is a broad term and signifies that over a single pump cycle, the maximum flow rate deviates from the average flow rate by no more than about 25% of the average flow rate during the pump cycle.

As discussed above, in some embodiments, flow and pressure pulsations created by a pump 100*b* can be dampened by the various reservoirs, tubing segments, and other devices in a circuit, and can result in more uniform flow rates and pressures. In certain embodiments, the uptake flow rate at a blood source 238 (e.g., a patient) and/or a delivery flow rate at a blood delivery destination 239 (e.g., a patient) can be essentially constant during a pump cycle. As used herein, the term "essentially constant" when used to describe a flow rate is a broad term and signifies that over a single pump cycle, the maximum flow rate deviates from an average flow rate by no more than about 10% of the average flow rate during the pump cycle. The pump 100*b* used to create the chart of FIG. 20 comprised two chambers, each having a displacement volume of about 25 milliliters. The chart illustrates the pump 100*b* as having operated at 200 millisecond per stroke (i.e., 400 millisecond per cycle or 150 cycles per minute). The pressure level in the pressure source 220 was established at 390 mmHg, the level of suction in the suction source was established at −125 mmHg, and the flow rate of blood effected by pump 100*b* was about 4 to 5 liters per minute. Connections lines 180*i* and 180*o* were comprised of plasticized PVC tubing with an inner diameter of 0.375 inches.

EXAMPLE 2

Figure 21:
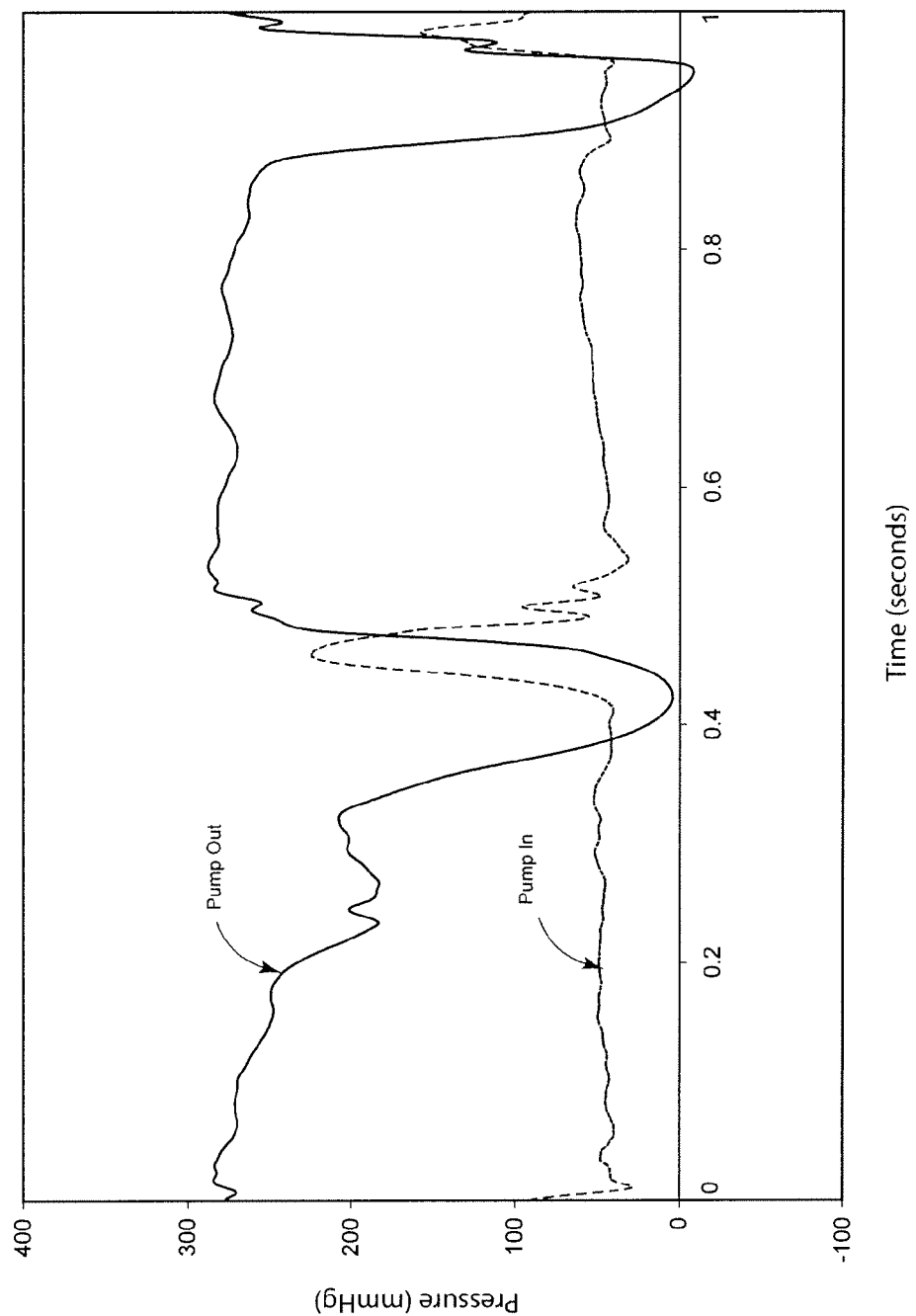
FIG. 21 is a chart showing an example of the pressure over time of blood entering and also of blood exiting an embodiment of a double diaphragm pump of the system depicted in FIG. 18 when the pump is configured for pulsatile outflow operation and relatively constant inflow operation.

FIG. 21 is a chart showing an example of pressure over time during a single pump cycle of an embodiment of a pump 100*g* used in a simulation of a heart assist system such as the system 750 of FIG. 18. The chart depicts the pressure over time during a single pump cycle of blood entering the pump 100*g* (illustrated by the curve "Pump In") and also depicts the pressure over time of blood exiting the pump 100*g* (illustrated by the curve "Pump Out"). The pump 100*g* was operated in a mode for relatively uniform flow entering an extracorporeal circuit and pulsatile outflow from the circuit.

Various operational parameters of the pump 100*g* of the present example or of other embodiments of the pump can be altered such that the inflow to the extracorporeal circuit is more uniform than that shown. For example, in some embodiments, the peak of the "Pump In" line at the time coordinate of about 0.45 seconds is smaller (e.g., has a maximum valve of between about 20 and about 80 mmHg) and/or may be relatively more constricted. Similarly, the pulsatile characteristics of the outflow from the extracorporeal circuit may be modified, as briefly discussed below.

The pump 100*g* used to create the chart of FIG. 21 comprised two chambers with each chamber having a displacement volume of about 25 milliliters. The chart illustrates the pump 100*g* as having operated at 500 millisecond per stroke (i.e., 1 second per cycle or 60 cycles per minute). The pressure level in the pressure source 220 was established at 300 mmHg and the level of suction in the suction source was established at 0 mmHg. The flowrate of blood effected by pump 100*g* was around 3 liters per minute. Shorter more pronounced pulse widths can be generated by extending the cycle time or increasing the pressure level in the pressure source 220. The pump was located about 30 inches below the fluid source 238 creating a positive pressure head of about 50 mmHg. Connections lines 180*i* and 180*o* were comprised of plasticized PVC tubing with an inner diameter of 0.375 inches. The outlet line 180*o* inner diameter was further reduced to 0.25 inches inner diameter for simulating a percutaneous access and arterial connection 754. The blood flowing through the connection lines caused pressure drops to and from the pump and the blood was delivered to the blood return 239 at less than 100 mmHg. The blood pump 100*g* of the illustrated example can create high pressures in the blood to overcome line losses, and as a result, a much smaller lumen can be used to access the vasculature of a patient P.

EXAMPLE 3A

Figure 22A:
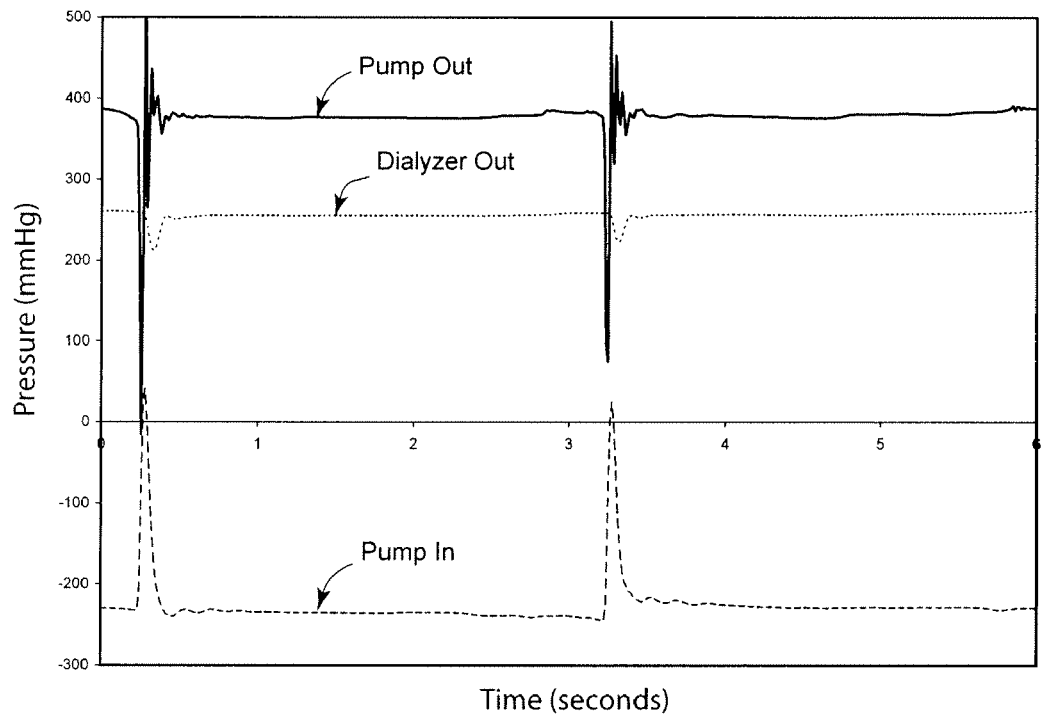
FIG. 22A is a chart showing an example of the pressure over time of blood entering and also of blood exiting an embodiment of a double diaphragm pump of the system depicted in FIG. 19, as well as the pressure over time of blood exiting the dialyzer, when the pump is configured for use in a hemodialysis procedure and controlled for relatively constant inflow operation and relatively constant outflow operation.

FIG. 22A is a chart showing an example of pressure over time during a single pump cycle of an embodiment of a pump 100h used in a simulation of a hemodialysis system such as the system 800 of FIG. 19. The chart depicts the pressure over time during a single pump cycle of blood entering the pump 100h (illustrated by the curve "Pump In"), the pressure over time of blood exiting the pump 100h (illustrated by the curve "Pump Out"), and also depicts the pressure over time of blood exiting the dialyzer 810 (illustrated by the curve "Dialyzer Out"). The pump 100h was operated in a mode for relatively uniform flow entering the circuit and relatively uniform flow exiting the extracorporeal circuit.

The chart illustrates the pump 100h as having operated at 3 seconds per stroke (i.e., 6 seconds per cycle or 10 cycles per minute). The pressure level in the pressure source 220 was established below about 390 mmHg, which caused the dialyzer out pressure to remain below about 250 mmHg, and the level of suction in the suction source was established above about 250 mmHg. The pump 100h used to create the chart of FIG. 22A comprised two chambers with each chamber having a displacement volume of about 25 milliliters. The flowrate of blood effected by pump 100h was about 250 to about 350 milliliters per minute. Connection lines 180i and 180o were comprised of plasticized PVC tubing with an inner diameter of 0.25 inches and connected to a commonly used disposable hemodialysis circuit with 16 gauge hemodialysis needles as the connections to fluid source 238 and fluid return 239. Most of the flow-driven pressure losses in the hemodialysis circuit 800 occurred through the needles and the dialyzer 810.

EXAMPLE 3B

Figure 22B:
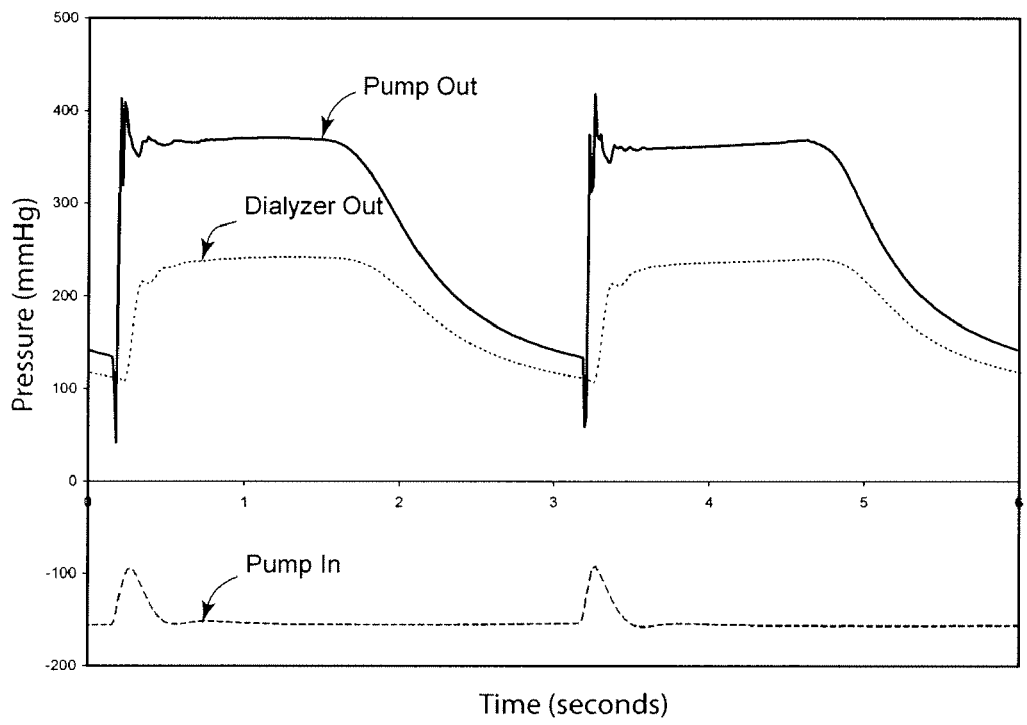
FIG. 22B is a chart showing an example of the pressure over time of blood entering and also of blood exiting the double diaphragm pump in the system depicted in FIG. 19, as well as the pressure over time of blood exiting the dialyzer, when the pump is configured for use in a hemodialysis procedure and controlled for relatively constant inflow operation and pulsatile outflow operation.

FIG. 22B is a chart showing an example of pressure over time during a single pump cycle of an embodiment of a pump 100h used in a simulation of a hemodialysis system such as the system 800 of FIG. 19. The chart depicts the pressure over time during a single pump cycle of blood entering the pump 100h (illustrated by the curve "Pump In"), the pressure over time of blood exiting the pump 100h (illustrated by the curve "Pump Out"), and also depicts the pressure over time of blood exiting the dialyzer 810 (illustrated by the curve "Dialyzer Out"). The pump 100h was operated in a mode for relatively uniform flow entering the circuit and pulsatile flow exiting the extracorporeal circuit.

The pump 100h is illustrated as having operated at 3 seconds per stroke (i.e., 6 seconds per cycle or 10 cycles per minute). Shorter, more pronounced pulse widths can be generated by extending the cycle time or increasing the pressure level in the pressure source 220. The pressure level in the pressure source 220 was established below about 360 mmHg, which caused the dialyzer out pressure to remain below about 250 mmHg, and the level of suction in the suction source was established above about −160 mmHg. The pump 100h used to create the chart of FIG. 22B comprised two chambers with each chamber having a displacement volume of about 25 milliliters. The flowrate of blood effected by pump 100g was about 200 to about 300 millileters per minute. Connections lines 180i and 180o were comprised of plasticized PVC tubing with an inner diameter of 0.25 inches and connected to a commonly used disposable hemodialysis circuit with 16 gauge hemodialysis needles as the connections to fluid source 238 and fluid return 239. Most of the hemodialysis circuit blood flow pressure losses occured through the needles and the dialyzer 810. A more pronounced pulsation can be achieved at a given flowrate with a combination of longer cycle times, larger bore needles, and lower flow resistance of the dialyzer.

Various features and structures discussed herein, and equivalents thereof, can provide specific functionalities. By way of illustration, in some embodiments, the first and second pump chambers 103a, b are examples of first and second means for selectively drawing process fluid from a process fluid source (e.g., the fluid source 238) and selectively expelling process fluid to a process fluid delivery destination (e.g., the process fluid delivery destination 239); the first and second inlet valves 101i, 102i are examples of first and second means for selectively permitting process fluid to flow to the first and second means for selectively drawing process fluid from a process fluid source and selectively expelling process fluid to a process fluid delivery destination, respectively; and the first and second outlet valves 101o, 102o are examples of first and second means for selectively permitting process fluid to flow from the first and second means for selectively drawing process fluid from a process fluid source and selectively expelling process fluid to a process fluid delivery destination, respectively.

As used in this specification, including the claims, the term "and/or" is a conjunction that is either inclusive or exclusive. Accordingly, the term "and/or" either signifies the presence of two or more things in a group or signifies that one selection may be made from a group of alternatives.

Without further elaboration, it is believed that one skilled in the art can use the preceding description to utilize the claimed inventions to their fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles discussed. In other words, various modifications and improvements of the embodiments specifically disclosed in the description above are within the scope of the appended claims. For example, any suitable combination of features of the various embodiments described is contemplated. Note that elements recited in means-plus-function format are intended to be construed in accordance with 35 U.S.C. §112 ¶6. The scope of the invention is therefore defined by the following claims.

What is claimed is:

1. A hemodialysis system for removing blood from a patient and returning blood to the patient, the system comprising:
　a single blood pump that comprises:
　　a first pump chamber and a second pump chamber;
　　a first inlet valve configured to control the flow of blood to the first pump chamber;
　　a second inlet valve configured to control the flow of blood to the second pump chamber;
　　a first outlet valve configured to control the flow of blood from the first pump chamber; and
　　a second outlet valve configured to control the flow of blood from the second pump chamber;
　a dialyzer in fluid communication with the blood pump;
　one or more pressure sensors configured to obtain information regarding blood pressure within the system; and
　a control base coupled with the pump, the control base comprising a controllable pneumatic regulator that is configured to control a pressure level of motive fluid that is delivered to the pump, the control base configured to selectively provide fluid communication between a first source of motive fluid at a first pressure level and the pump, the control base configured to alternate between a first state and a second state at a cycle rate, the control base configured to provide fluid communication between the first source of motive fluid and the first pump chamber of the pump in the first state and configured to provide fluid communication between the first source of motive fluid and the second pump chamber of the pump in the second state, wherein the control base is configured to receive information regarding blood pressure within the system from the one or more pressure sensors, and wherein the control base is configured to utilize the information to selectively control a setting of the pneumatic regulator so as to control the pressure level of motive fluid that is delivered to the pump to effect a substantially constant flow of blood uptake from the patient.

2. The system of claim 1, wherein the control base is configured to provide fluid communication between a second source of motive fluid at a second pressure level and the second pump chamber of the pump when in the first state and between the second source of motive fluid and the first pump chamber of the pump when in the second state.

3. The system of claim 2, wherein the control base is configured to utilize the information regarding blood pressure within the system to selectively control one or more of the second pressure level and the cycle rate to effect a substantially constant flow of blood uptake from the patient.

4. The system of claim 1, wherein the control base is configured to utilize the information regarding blood pressure within the system to selectively control one or more of the pressure level of motive fluid that is delivered to the pump and the cycle rate to effect a pulsatile flow of blood to the dialyzer.

5. The system of claim 1, wherein the control base is configured to utilize the information regarding blood pressure within the system to selectively control one or more of the pressure level of motive fluid that is delivered to the pump and the cycle rate to effect an effectively constant flow of blood return to the patient.

6. The system of claim 1, wherein the control base is configured to actuate the first and the second pump chambers such that the first pump chamber fills with blood as the second pump chamber expels blood.

7. The system of claim 1, wherein the first pump chamber comprises a first diaphragm actuation region configured to move within the first pump chamber between end-of-stroke positions and the second pump chamber comprises a second diaphragm actuation region configured to move within the second pump chamber between end-of-stroke positions, and wherein the control base selectively controls one or more of the pressure level of motive fluid that is delivered to the pump and the cycle rate to prevent the first diaphragm actuation region from reaching an end-of-stroke position as the first pump chamber fills with blood and to prevent the second diaphragm actuation region from reaching an end-of-stroke position as the second pump chamber fills with blood.

8. The blood pumping system of claim 1, wherein the pump and the control base are configured to couple with each other in releasable engagement such that the pump can be removed from the control base and replaced with another pump of like construction.

9. The blood pumping system of claim 1, wherein one of the pump and the control base comprises a hook and the other of the pump and the control base comprises a latch, the hook and latch configured to cooperate to selectively connect the pump with the control base.

10. The blood pumping system of claim 1, wherein one or more of the first pump chamber, the first inlet valve, and the first outlet valve comprises a diaphragm actuation region that defines a dome height when in a natural state.

* * * * *

(12) EX PARTE REEXAMINATION CERTIFICATE (10520th)
United States Patent
Orr

(10) Number: US 8,038,640 C1
(45) Certificate Issued: Mar. 4, 2015

(54) DOUBLE DIAPHRAGM PUMP AND RELATED SYSTEMS AND METHODS

(75) Inventor: Troy J. Orr, Draper, UT (US)

(73) Assignee: Fresenius Medical Care Holdings, Inc., Waltham, MA (US)

Reexamination Request:
No. 90/013,241, May 19, 2014

Reexamination Certificate for:
Patent No.: 8,038,640
Issued: Oct. 18, 2011
Appl. No.: 11/945,200
Filed: Nov. 26, 2007

(51) Int. Cl.
*A61M 37/00* (2006.01)
(52) U.S. Cl.
USPC ................................. 604/6.11; 417/477.2

(58) Field of Classification Search
None
See application file for complete search history.

(56) References Cited

To view the complete listing of prior art documents cited during the proceeding for Reexamination Control Number 90/013,241, please refer to the USPTO's public Patent Application Information Retrieval (PAIR) system under the Display References tab.

*Primary Examiner* — Jeffrey R Jastrzab

(57) ABSTRACT

In some arrangements, a pump for moving a fluid has one or more pump chambers and one or more flow control valves with diaphragm actuation regions. Motive fluid can activate the diaphragm actuation regions, and a pattern of fluid flow can be controlled by varying the pressure levels of the motive fluid.

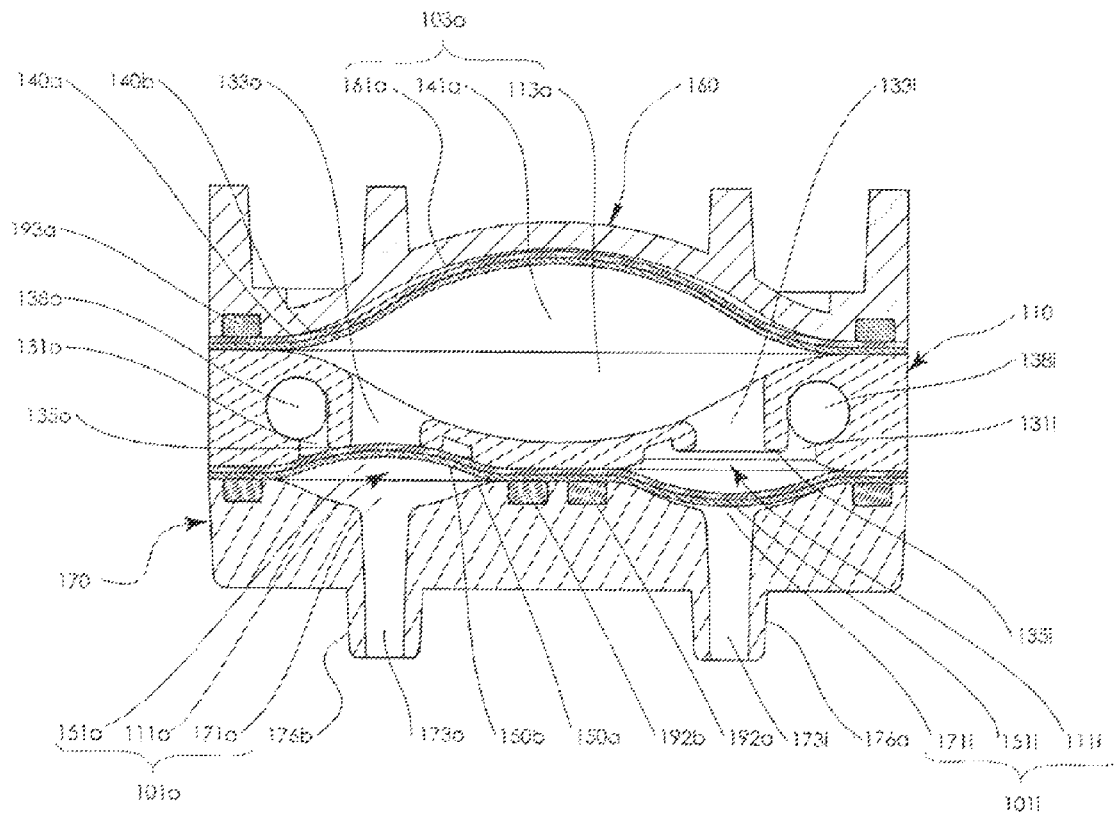

US 8,038,640 C1

EX PARTE
REEXAMINATION CERTIFICATE
ISSUED UNDER 35 U.S.C. 307

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 7 is confirmed.

Claim 1 is cancelled.

Claims 2, 4-6 and 8-10 are determined to be patentable as amended.

Claim 3, dependent on an amended claim, is determined to be patentable.

New claims 11-62 are added and determined to be patentable.

2. The system of claim [1] 7, wherein the control base is configured to provide fluid communication between a second source of motive fluid at a second pressure level and the second pump chamber of the pump when in the first state and between the second source of motive fluid and the first pump chamber of the pump when in the second state.

4. The system of claim [1] 7, wherein the control base is configured to utilize the information regarding blood pressure within the system to selectively control one or more of the pressure level of motive fluid that is delivered to the pump and the cycle rate to effect a pulsatile flow of blood to the dialyzer.

5. The system of claim [1] 7, wherein the control base is configured to utilize the information regarding blood pressure within the system to selectively control one or more of the pressure level of motive fluid that is delivered to the pump and the cycle rate to effect an effectively constant flow of blood return to the patient.

6. The system of claim [1] 7, wherein the control base is configured to actuate the first and the second pump chambers such that the first pump chamber fills with blood as the second pump chamber expels blood.

8. The system of claim [1] 7, wherein the pump and the control base are configured to couple with each other in releasable engagement such that the pump can be removed from the control base and replaced with another pump of like construction.

9. The system of claim [1] 7, wherein one of the pump and the control base comprises a hook and the other of the pump and the control base comprises a latch, the hook and latch configured to cooperate to selectively connect the pump with the control base.

10. The system of claim [1] 7, wherein one or more of the first pump chamber, the first inlet valve, and the first outlet valve comprises a diaphragm actuation region that defines a dome height when in a natural state.

11. *The system of claim 7, wherein the control base is configured to control the pneumatic regulator to control the pressure level of motive fluid in the first source of motive fluid based on the information regarding blood pressure within the system from the one or more pressure sensors.*

12. *The system of claim 11, wherein the control base is configured to control the pneumatic regulator to vary the pressure level of motive fluid in the first source of motive fluid among a plurality of pressure levels ranging between and including a first pressure level and a second pressure level, wherein at least one of the plurality of pressure levels is greater than the first pressure level and less than the second pressure level.*

13. *The system of claim 2, wherein the control base is configured to control the pneumatic regulator to control the pressure level of motive fluid in the second source of motive fluid based on the information regarding blood pressure within the system from the one or more pressure sensors.*

14. *The system of claim 13, wherein the control base is configured to control the pneumatic regulator to vary the pressure level of motive fluid in the second source of motive fluid among a plurality of pressure levels ranging between and including a first pressure level and a second pressure level, wherein at least one of the plurality of pressure levels is greater than the first pressure level and less than the second pressure level.*

15. *The system of claim 13, wherein the second source of motive fluid is a vacuum source, and wherein the control base is configured to vary the pressure level of motive fluid provided by the vacuum source between a first vacuum level value and a second vacuum level value.*

16. *The system of claim 13, wherein the control base is configured to alternately vary the pressure level of the motive fluid between (i) a positive pressure level at any of a plurality of values between a first positive pressure level value and a second positive pressure level value, and (ii) a vacuum level at any of a plurality of values between a first vacuum level value and a second vacuum level value.*

17. *The system of claim 7, wherein the control base is configured to vary the pressure level of motive fluid provided by the first source of motive fluid between a first positive pressure level value and a second positive pressure level value.*

18. *A hemodialysis system for removing blood from a patient and returning blood to the patient, the system comprising:*
   *a single blood pump that comprises:*
      *a first pump chamber and a second pump chamber;*
      *a first inlet valve configured to control the flow of blood to the first pump chamber;*
      *a second inlet valve configured to control the flow of blood to the second pump chamber;*
      *a first outlet valve configured to control the flow of blood from the first pump chamber; and*
      *a second outlet valve configured to control the flow of blood from the second pump chamber;*
   *a dialyzer in fluid communication with the blood pump;*
   *one or more pressure sensors configured to obtain information regarding blood pressure within the system; and*
   *a control base coupled with the pump, the control base comprising a controllable pneumatic regulator configured to control a pressure level of motive fluid that is delivered to the pump, the control base configured to selectively provide fluid communication between a first source of motive fluid at a first pressure level and the pump, the control base configured to alternate between a first state and a second state at a cycle rate, the control base configured to provide fluid communication between the first source of motive fluid and the first pump chamber of the pump in the first state and configured to provide fluid communication between the first source of motive fluid and the second pump chamber of the pump in the second state,* wherein the control base is configured to receive information regarding blood pressure within the system from the one or more pressure sensors, and wherein the control base is configured to utilize the information to selectively control a setting of the pneumatic regulator so as to control the pressure level of motive fluid that is delivered to the pump to effect a substantially constant flow of blood uptake from the patient by switching from a fill stroke to a dispense stroke in the first pump chamber before the first pump chamber has completely filled with blood.

19. The system of claim 18, wherein the control base is configured to effect a substantially constant flow of blood uptake from the patient by switching from a fill stroke to a dispense stroke in the first pump chamber before the first pump chamber has completely filled with blood when transitioning from the first state to the second state.

20. The system of claim 19, wherein the control base is further configured to effect a substantially constant flow of blood uptake from the patient by retaining the first pump chamber in an end-of-dispense stroke position for a period of time before transitioning from the second state to the first state.

21. The system of claim 18, wherein the control base is configured to effect a substantially constant flow of blood uptake from the patient by preventing the second pump chamber from reaching a fill end-of-stroke condition of the second pump chamber prior to transitioning from the second state to the first state.

22. A hemodialysis system for removing blood from a patient and returning blood to the patient, the system comprising:
   a single blood pump that comprises:
      a first pump chamber and a second pump chamber;
      a first inlet valve configured to control the flow of blood to the first pump chamber;
      a second inlet valve configured to control the flow of blood to the second pump chamber;
      a first outlet valve configured to control the flow of blood from the first pump chamber; and
      a second outlet valve configured to control the flow of blood from the second pump chamber;
   a dialyzer in fluid communication with the blood pump;
   one or more pressure sensors configured to obtain information regarding blood pressure within the system; and
   a control base coupled with the pump, the control base comprising a controllable pneumatic regulator configured to control a pressure level of motive fluid that is delivered to the pump, the control base configured to selectively provide fluid communication between a first source of motive fluid at a first pressure level and the pump, the control base configured to alternate between a first state and a second state at a cycle rate, the control base configured to provide fluid communication between the first source of motive fluid and the first pump chamber of the pump in the first state and configured to provide fluid communication between the first source of motive fluid and the second pump chamber of the pump in the second state,
   wherein the control base is configured to receive information regarding blood pressure within the system from the one or more pressure sensors, and
   wherein the control base is configured to utilize the information to selectively control a setting of the pneumatic regulator so as to control the pressure level of motive fluid that is delivered to the pump to effect a substantially constant flow of blood uptake from the patient, wherein the first pump chamber comprises a first diaphragm actuation region configured to move within the first pump chamber between a discharge end-of-stroke position and a fill end-of-stroke position, and wherein the control base prevents the first diaphragm actuation region from reaching the fill end-of-stroke position by selectively controlling (i) one or more of the pressure levels of motive fluid that is delivered to the pump, and (ii) the cycle rate.

23. A hemodialysis system for removing blood from a patient and returning blood to the patient, the system comprising:
   a single blood pump that comprises:
      a first pump chamber and a second pump chamber;
      a first inlet valve configured to control the flow of blood to the first pump chamber;
      a second inlet valve configured to control the flow of blood to the second pump chamber;
      a first outlet valve configured to control the flow of blood from the first pump chamber; and
      a second outlet valve configured to control the flow of blood from the second pump chamber;
   a dialyzer in fluid communication with the blood pump;
   one or more pressure sensors configured to obtain information regarding blood pressure within the system; and
   a control base coupled with the pump, the control base comprising a controllable pneumatic regulator configured to control a pressure level of motive fluid that is delivered to the pump, the control base configured to selectively provide fluid communication between a first source of motive fluid at a first pressure level and the pump, the control base configured to alternate between a first state and a second state at a cycle rate, the control base configured to provide fluid communication between the first source of motive fluid and the first pump chamber of the pump in the first state and configured to provide fluid communication between the first source of motive fluid and the second pump chamber of the pump in the second state,
   wherein the control base is configured to receive information regarding blood pressure within the system from the one or more pressure sensors, and
   wherein the control base is configured to utilize the information to selectively control a setting of the pneumatic regulator so as to control the pressure level of motive fluid that is delivered to the pump to be unique to the pump relative to other pumps in the hemodialysis system to effect a substantially constant flow of blood uptake from the patient.

24. A hemodialysis system for removing blood from a patient and returning blood to the patient, the system comprising:
   a single blood pump that comprises:
      a first pump chamber and a second pump chamber;
      a first inlet valve configured to control the flow of blood to the first pump chamber;
      a second inlet valve configured to control the flow of blood to the second pump chamber;
      a first outlet valve configured to control the flow of blood from the first pump chamber; and
      a second outlet valve configured to control the flow of blood from the second pump chamber;
   a dialyzer in fluid communication with the blood pump;
   one or more pressure sensors configured to obtain information regarding blood pressure within the system; and
   a control base coupled with the pump, the control base comprising:

a controllable pneumatic regulator, and
a motive fluid control valve that is connected to each of the first inlet valve, the second inlet valve, the first outlet valve and the second outlet valve,
wherein the control base is configured to cause the controllable pneumatic regulator to operate the motive fluid control valve to control a pressure level of motive fluid that is delivered to the pump, the control base configured to operate the motive fluid control valve to selectively provide fluid communication between a first source of motive fluid at a first pressure level and the pump, the control base configured to operate the motive fluid control valve to alternate between a first state and a second state at a cycle rate, the control base configured to operate the motive fluid control valve to provide fluid communication between the first source of motive fluid and the first pump chamber of the pump in the first state and configured to operate the motive fluid control valve to provide fluid communication between the first source of motive fluid and the second pump chamber of the pump in the second state,
wherein the control base is configured to receive information regarding blood pressure within the system from the one or more pressure sensors, and
wherein the control base is configured to utilize the information to selectively control a setting of the pneumatic regulator to control the pressure level of motive fluid that is delivered to the pump to effect a substantially constant flow of blood uptake from the patient.

25. The system of claim 24, wherein the control base is configured to provide fluid communication between a second source of motive fluid at a second pressure level and the second pump chamber of the pump when in the first state and between the second source of motive fluid and the first pump chamber of the pump when in the second state.

26. The system of claim 25, wherein the control base is configured to utilize the information regarding blood pressure within the system to selectively control one or more of the second pressure level and the cycle rate to effect a substantially constant flow of blood uptake from the patient.

27. The system of claim 24, wherein the control base is configured to utilize the information regarding blood pressure within the system to selectively control one or more of the pressure level of motive fluid that is delivered to the pump and the cycle rate to effect a pulsatile flow of blood to the dialyzer.

28. The system of claim 24, wherein the control base is configured to utilize the information regarding blood pressure within the system to selectively control one or more of the pressure level of motive fluid that is delivered to the pump and the cycle rate to effect an effectively constant flow of blood return to the patient.

29. The system of claim 24, wherein the control base is configured to actuate the first and the second pump chambers such that the first pump chamber fills with blood as the second pump chamber expels blood.

30. The system of claim 24, wherein the first pump chamber comprises a first diaphragm actuation region configured to move within the first pump chamber between end-of-stroke positions and the second pump chamber comprises a second diaphragm actuation region configured to move within the second pump chamber between end-of-stroke positions, and
wherein the control base selectively controls the pressure level of motive fluid that is delivered to the pump and the cycle rate to prevent the first diaphragm actuation region from reaching an end-of-stroke position as the first pump chamber fills with blood and to prevent the second diaphragm actuation region from reaching an end-of-stroke position as the second pump chamber fills with blood.

31. The system of claim 24, wherein the pump and the control base are configured to couple with each other in releasable engagement such that the pump can be removed from the control base and replaced with another pump of like construction.

32. The system of claim 24, wherein one of the pump and the control base comprises a hook and the other of the pump and the control base comprises a latch, the hook and latch configured to cooperate to selectively connect the pump with the control base.

33. The system of claim 24, wherein one or more of the first pump chamber, the first inlet valve, and the first outlet valve comprises a diaphragm actuation region that defines a dome height when in a natural state.

34. The system of claim 24, wherein the single blood pump comprises a pair of first diaphragms and a pair of second diaphragms positioned in the first pump chamber and the second pump chamber, wherein the control base is configured to operate the motive fluid control valve to control a pressure level of motive fluid that is delivered to the pump to deflect the pair of first diaphragms and the pair of second diaphragms.

35. The system of claim 34, wherein the pair of first diaphragms are positioned over each other in the first pump chamber and the second pump chamber.

36. The system of claim 34, wherein the pair of second diaphragms are positioned over each other in the first pump chamber and the second pump chamber.

37. The system of claim 24, wherein the motive fluid control valve comprises one or more air valves.

38. The system of claim 37, wherein the motive fluid control valve comprises one or more pneumatic control and conditioning devices.

39. The system of claim 24, wherein the motive fluid control valve is a single motive fluid control valve connected to the single blood pump.

40. The system of claim 24, wherein the motive fluid control valve is configured to operate in a plurality of positions that correspond to a respective plurality of states of the motive fluid control valve.

41. The system of claim 40, wherein the plurality of states comprises a resting state in which the motive fluid control valve prevents fluid communication between the blood pump and the first source of motive fluid.

42. The system of claim 41, wherein the motive fluid control valve is configured to pass through the resting state when alternating between the first state and the second state at the cycle rate.

43. The system of claim 41, wherein the motive fluid control valve is configured to alternate between the first state and the second state at the cycle rate without passing through the resting state.

44. The system of claim 25, wherein the motive fluid control valve comprises a first supply port and a second supply port, and wherein, in the first state, the motive fluid control valve provides fluid communication between the first source of motive fluid and the first supply port and provides fluid communication between the second source of motive fluid and the second supply port.

45. The system of claim 44, wherein, in the second state, the motive fluid control valve provides fluid communication between the first source of motive fluid and the second supply port and provides fluid communication between the second source of motive fluid and the first supply port.

46. A hemodialysis system for removing blood from a patient and returning blood to the patient, the system comprising:

a single blood pump that comprises:
  a first pump chamber and a second pump chamber;
  first diaphragm layers and second diaphragm layers positioned in the first pump chamber and the second pump chamber;
  a first inlet valve configured to control the flow of blood to the first pump chamber;
  a second inlet valve configured to control the flow of blood to the second pump chamber;
  a first outlet valve configured to control the flow of blood from the first pump chamber; and
  a second outlet valve configured to control the flow of blood from the second pump chamber;
a dialyzer in fluid communication with the blood pump;
one or more pressure sensors configured to obtain information regarding blood pressure within the system; and
a control base coupled with the pump, the control base comprising a controllable pneumatic regulator that is configured to control a pressure level of motive fluid that is delivered to the pump to deflect the first diaphragm layers and the second diaphragm layers, the control base configured to selectively provide fluid communication between a first source of motive fluid at a first pressure level and the pump, the control base configured to alternate between a first state and a second state at a cycle rate, the control base configured to provide fluid communication between the first source of motive fluid and the first pump chamber of the pump in the first state and configured to provide fluid communication between the first source of motive fluid and the second pump chamber of the pump in the second state,
wherein the control base is configured to receive information regarding blood pressure within the system from the one or more pressure sensors, and
wherein the control base is configured to utilize the information to selectively control a setting of the pneumatic regulator so as to control the pressure level of motive fluid that is delivered to the pump to effect a substantially constant flow of blood uptake from the patient.

47. The system of claim 46, wherein the first diaphragm layers comprise a pair of first diaphragms and the second diaphragm layers comprise a pair of second diaphragms.

48. The system of claim 47, wherein the control base comprises a motive fluid control valve that is connected to the controllable pneumatic regulator and to each of the first inlet valve, the second inlet valve, the first outlet valve and the second outlet valve, wherein the pneumatic regulator is configured to operate the motive fluid control valve to control a pressure level of motive fluid that is delivered to the pump to deflect the first diaphragm layer and the second diaphragm layer.

49. The system of claim 47, wherein the pair of first diaphragms and the pair of second diaphragms extend to a perimeter of the single blood pump.

50. The system of claim 47, wherein each of the pair of first diaphragms positioned in the first pump chamber and the second pump chamber is a portion of the same diaphragm.

51. The system of claim 47, wherein each of the pair of second diaphragms positioned in the first pump chamber and the second pump chamber is a portion of the same diaphragm.

52. The system of claim 47, wherein each of the pair of first diaphragms positioned in the first pump chamber is separate from each of the pair of first diaphragms positioned in the second pump chamber.

53. The system of claim 47, wherein each of the pair of second diaphragms positioned in the first pump chamber is separate from each of the pair of second diaphragms positioned in the second pump chamber.

54. The system of claim 47, wherein each of the pair of first diaphragms comprises a pair of pre-formed actuation regions having shapes that correspond to the shapes of the first pump chamber and the second pump chamber, respectively.

55. The system of claim 54, wherein each pre-formed actuation region is configured to move between a natural shape and an inversion of the natural shape.

56. The system of claim 47, wherein each of the pair of second diaphragms comprises a pair of pre-formed actuation regions.

57. The system of claim 47, wherein a ratio of a radius of bending curvature of a pre-formed actuation region and a thickness of a diaphragm is in a range between 5:1 and 100:1.

58. The system of claim 47, wherein each of the pair of first diaphragms and the pair of second diaphragms has a thickness in a range between 0.001 inches and 0.060 inches.

59. The system of claim 46, wherein the single blood pump comprises a pump body that separates the first diaphragm layers from the second diaphragm layers.

60. The system of claim 59, wherein the single blood pump comprises a passage that passes through the pump body and that provides a fluid communication between the first diaphragm layers and the second diaphragm layers.

61. The system of claim 60, wherein the control base is configured to operate the pneumatic regulator to pass the motive fluid under pressure through the passage to deflect the first diaphragm layers and the second diaphragm layers simultaneously.

62. A hemodialysis system for removing blood from a patient and returning blood to the patient, the system comprising:
  a single blood pump that comprises:
    a first pump chamber and a second pump chamber;
    a first inlet valve configured to control the flow of blood to the first pump chamber;
    a second inlet valve configured to control the flow of blood to the second pump chamber;
    a first outlet valve configured to control the flow of blood from the first pump chamber; and
    a second outlet valve configured to control the flow of blood from the second pump chamber;
  a dialyzer in fluid communication with the blood pump;
  one or more pressure sensors configured to obtain information regarding blood pressure within the system; and
  a control base coupled with the pump, the control base comprising a controllable pneumatic regulator configured to control a pressure level of motive fluid that is delivered to the pump, the control base configured to selectively provide fluid communication between a first source of motive fluid at a first pressure level and the pump, the control base configured to alternate between a first state and a second state at a cycle rate, the control base configured to provide fluid communication between the first source of motive fluid and the first pump chamber of the pump in the first state and configured to provide fluid communication between the first source of motive fluid and the second pump chamber of the pump in the second state,
  wherein the control base is configured to receive information regarding blood pressure within the system from the one or more pressure sensors, and
  wherein the control base is configured to utilize the information to selectively control a setting of the pneumatic regulator so as to control the pressure level of motive

*fluid that is delivered to the pump to effect a substantially constant flow of blood uptake from the patient,*

*wherein, utilizing the information regarding the blood pressure within the system received from the one or more pressure sensors, the control base controls the pressure level of motive fluid delivered to the pump by controlling two independent factors: (i) the cycle rate of alternating between the first state and the second state, and (ii) the pressure level of motive fluid delivered from the motive fluid pressure source.*

\* \* \* \* \*